US012772998B2

(12) United States Patent
Markosyan et al.

(10) Patent No.: US 12,772,998 B2
(45) **Date of Patent: *Oct. 27, 2026**

(54) MOGROSIDES AND USE THEREOF

(71) Applicant: PURECIRCLE USA INC., Westchester, IL (US)

(72) Inventors: Avetik Markosyan, Kuala Lumpur (MY); Siew Yin Chow, Selangor (MY); Saravanan Ramandach, Negeri Sembilan (MY)

(73) Assignee: PureCircle USA Inc., Westchester, IL (US)

( * ) Notice: Subject to any disclaimer, the term of this patent is extended or adjusted under 35 U.S.C. 154(b) by 1017 days.

This patent is subject to a terminal disclaimer.

(21) Appl. No.: 17/987,071

(22) Filed: Nov. 15, 2022

(65) Prior Publication Data

US 2023/0127534 A1 Apr. 27, 2023

Related U.S. Application Data

(63) Continuation of application No. 16/348,444, filed as application No. PCT/US2017/060604 on Nov. 8, 2017, now Pat. No. 11,547,128.

(60) Provisional application No. 62/419,238, filed on Nov. 8, 2016.

(51) Int. Cl.

| | |
|---|---|
| ***A23L 2/60*** | (2006.01) |
| ***A23L 27/30*** | (2016.01) |
| ***A24B 13/00*** | (2006.01) |
| ***A61K 8/63*** | (2006.01) |
| ***A61K 8/97*** | (2017.01) |
| ***A61K 8/9789*** | (2017.01) |
| ***A61K 8/9794*** | (2017.01) |
| ***A61Q 19/00*** | (2006.01) |
| ***C07J 17/00*** | (2006.01) |
| ***G01N 30/02*** | (2006.01) |
| *A61G 19/00* | (2006.01) |

(52) U.S. Cl.

CPC ................. *A23L 2/60* (2013.01); *A23L 27/36* (2016.08); *A61K 8/63* (2013.01); *A61K 8/97* (2013.01); *C07J 17/005* (2013.01); *A23L 27/34* (2016.08); *A23V 2002/00* (2013.01); *A23V 2250/24* (2013.01); *A23V 2250/254* (2013.01); *A23V 2300/14* (2013.01); *A24B 13/00* (2013.01); *A61G 19/00* (2013.01); *A61K 8/9789* (2017.08); *A61K 8/9794* (2017.08); *G01N 2030/027* (2013.01)

(58) Field of Classification Search

CPC .. A23L 2/60; A23L 2250/25; A23L 2250/254; A23L 27/36

See application file for complete search history.

(56) References Cited

U.S. PATENT DOCUMENTS

| | | | | |
|---|---|---|---|---|
| 6,124,442 | A | 9/2000 | Zhou et al. | |
| 6,228,996 | B1 | 5/2001 | Zhou | |
| 9,101,162 | B2 | 8/2015 | Markosyan | |
| 11,547,128 | B2 * | 1/2023 | Markosyan | A23L 27/36 |
| 2007/0116819 | A1 | 5/2007 | Prakash et al. | |
| 2008/0108710 | A1 | 5/2008 | Prakash et al. | |
| 2009/0196966 | A1 | 8/2009 | West et al. | |
| 2010/0267847 | A1 | 10/2010 | Yoshinaka et al. | |

FOREIGN PATENT DOCUMENTS

| | | | |
|---|---|---|---|
| CN | 101029071 | A | 9/2007 |
| CN | 101050230 | A | 10/2007 |
| CN | 101407535 | A | 4/2009 |
| CN | 104926907 | A | 9/2015 |
| JP | 2001211854 | A | 8/2011 |
| WO | 9418855 | A1 | 9/1994 |
| WO | 2007062087 | A2 | 5/2007 |
| WO | 2008030121 | A1 | 3/2008 |
| WO | 2008149253 | A2 | 12/2008 |
| WO | 2009023975 | A2 | 2/2009 |
| WO | 2009063921 | A1 | 5/2009 |
| WO | 2016038617 | A1 | 3/2016 |
| WO | 2017075257 | A2 | 5/2017 |

OTHER PUBLICATIONS

European Search Report of patent application No. EP11179246.1 completed on Oct. 27, 2011 and mailed Nov. 20, 2011 (6 pages).
Communication pursuant to Article 94(3) EPC of European patent application No. EP11179246.1 mailed Oct. 17, 2012 (4 pages).
Natural High Potency Sweeteners by Kim et al., "Handbook of Sweeteners" by Marie et al. (Eds.), Springer Science & Business Media (New York), pp. 116-185, copyright 1991.
Isolation of the sweet components from Siraitia grosvenorli by Xia et al., Food Chem. 107, 1022-28 (2008).
Extended European Search Report of patent application No. EP13160563.6 completed on Jun. 19, 2013 and mailed on Jun. 28, 2013 (5 pages).
Extended European Search Report of patent application No. EP17870309.6 completed on Jul. 7, 2020 (31 pages).

(Continued)

*Primary Examiner* — Theodore R. Howell

(57) ABSTRACT

The present invention provides a process for preparation of compositions comprising mogrosides from fruit of *Siraitia grosvenorii*. The compositions have superior organoleptic properties compared to known mogroside compositions and are useful in wider range of consumables including foods and beverages.

7 Claims, 68 Drawing Sheets

(56) References Cited

OTHER PUBLICATIONS

Venkata Sai Prakash Chaturvedula et al: "Cucurbitane Glycosides from Siraitia grosvenorii", Journal of Carbohydrate Chemistry, vol. 30, No. 1, Jan. 1, 2011 (Jan. 1, 2011), pp. 16-26.
Hongyang Zhang et al: "Identification of flavonol and triterpene glycosides in Luo-Han-Guo extract using ultra-high performance liquid chromatography/quadrupole time-of-flight mass spectrometry", Journal of Food Composition and Analysis, vol. 25, No. 2, Mar. 1, 2012 (Mar. 1, 2012), pp. 142-148.
Fu Li et al: Cucurbitane glycosides from the fruit of Siraitia grosvenori and their effects on glucose uptake in human HepG2 cells in vi tro11, Food Chemistry, vol. 228, Feb. 10, 2017 (Feb. 10, 2017), pp. 567-573.

* cited by examiner

TO FIG. 29B

FROM FIG. 29A

FIG. 30

| Position | $\delta_C$ [ppm] | $\delta_H$ [ppm] | J [Hz]/ (INT) | HMBC (H ->C) |
|---|---|---|---|---|
| **Aglycon moiety** | | | | |
| 1 | 21.5 *t* | 1.16 *m*<br>1.47 *m* | | |
| 2 | 28.1 *t* | 1.70 *m*<br>1.88 *m* | | |
| 3 | 86.7 *d* | 3.35 *m* | | 1' |
| 4 | 41.4 *s* | - | | |
| 5 | 140.8 *s* | - | | |
| 6 | 118.6 *d* | 5.51 *m* | | |
| 7 | 2.39 *t* | 1.86 *m*<br>2.28 *m* | | |
| 8 | 44.5 *d* | 1.85 *m* | | |
| 9 | 49.9 *s* | - | | |
| 10 | 35.6 *d* | 2.34 *m* | | |
| 11 | 214.8 *s* | - | | |
| 12 | 48.8 *t* | 2.20 *d*<br>3.00 *d* | 13.5 Hz | |
| 13 | 44.6 *s* | - | | |
| 14 | 35.0 *s* | - | | |
| 15 | 28.4 *t* | 1.24 *m*<br>1.35 *m* | | |
| 16 | 28.7 *t* | 1.46 *m*<br>2.03 *m* | | |
| 17 | 50.2 *d* | 1.70 *m* | | |
| 18 | 16.3 *q* | 0.66 *s* | (3H) | 12, 13, 14, 17 |
| 19 | 19.1 *q* | 0.96 *s* | (3H) | 8, 9, 10, 11 |
| 20 | 36.3 *d* | 1.32 *m* | | |
| 21 | 18.3 *q* | 0.85 *d* | 6.1 (3H) | 17, 20, 22 |
| 22 | 32.6 *t* | 1.30 *m*<br>1.54 *m* | | |
| 23 | 33.0 *t* | 1.38 *m*<br>1.45 *m* | | |
| 24 | 92.7 *d* | 3.32 *m* | | 1'v |
| 25 | 72.9 s | - | | |
| 26 | 23.2 *q* | 1.05 *s* | (3H) | 24, 25, 27 |
| 27 | 25.7 *q* | 1.02 *s* | (3H) | 24, 25, 26 |
| 28 | 27.5 *q* | 0.97 *s* | (3H) | 3, 4, 5, 29 |
| 29 | 25.0 *q* | 1.13 *s* | (3H) | 3, 4, 5, 28 |
| 30 | 18.1 *q* | 1.02 *s* | (3H) | 8, 13, 14, 15 |

FIG. 31

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| 1ⁱ | 103.5 *d* | 4.20 *d* | 8.4 | 3 |
| 2ⁱ | 74.2 *d* | 3.12 *t* | 8.4 | |
| 3ⁱ | 77.0 *d* | 3.19 *t* | 8.4 | |
| 4ⁱ | 71.0 *d* | 3.12 *t* | 8.4 | |
| 5ⁱ | 76.1 *d* | 3.31 *m* | | |
| 6ⁱ | 68.7 *t* | 3.69 *m*<br>3.97 *m* | | |
| *β*-D-Glucopyranoside | | | | |
| 1ⁱⁱ | 103.8 *d* | 4.28 *d* | 8.4 | 6ⁱⁱ |
| 2ⁱⁱ | 74.2 *d* | 3.09 *t* | 8.4 | |
| 3ⁱⁱ | 77.2 *d* | 3.16 *t* | 8.4 | |
| 4ⁱⁱ | 71.1 *d* | 3.16 *t* | 8.4 | |
| 5ⁱⁱ | 76.2 *d* | 3.21 *m* | | |
| 6ⁱⁱ | 61.6 *t* | 3.56 *m*<br>3.76 *m* | | |
| *β*-D-Glucopyranoside | | | | |
| 1ⁱⁱⁱ | 103.8 *d* | 4.32 *d* | 8.4 | 6ⁱ |
| 2ⁱⁱⁱ | 74.2 *d* | 3.11 *t* | 8.4 | |
| 3ⁱⁱⁱ | 76.7 *d* | 3.14 *t* | 8.4 | |
| 4ⁱⁱⁱ | 70.9 *d* | 3.17 *t* | 8.4 | |
| 5ⁱⁱⁱ | 76.1 *d* | 3.35 *m* | | |
| 6ⁱⁱⁱ | 69.2 *t* | 3.66 *m*<br>4.05 *m* | | |
| *β*-D-Glucopyranoside | | | | |
| 1ⁱᵛ | 103.5 *d* | 4.35 *d* | 8.4 | 24 |
| 2ⁱᵛ | 79.6 *d* | 3.54 *t* | 8.4 | |
| 3ⁱᵛ | 77.8 *d* | 3.51 *t* | 8.4 | |
| 4ⁱᵛ | 70.4 *d* | 3.23 *t* | 8.4 | |
| 5ⁱᵛ | 76.7 *d* | 3.27 *m* | | |
| 6ⁱᵛ | 69.7 *t* | 3.42 *m*<br>4.18 *m* | | |
| *β*-D-Glucopyranoside | | | | |
| 1ᵛ | 103.4 *d* | 4.71 *d* | 8.4 | 2ⁱᵛ |
| 2ᵛ | 74.7 *d* | 3.18 *t* | 8.4 | |
| 3ᵛ | 76.9 *d* | 3.24 *t* | 8.4 | |
| 4ᵛ | 70.7 *d* | 3.19 *t* | 8.4 | |
| 5ᵛ | 76.0 *d* | 3.27 *m* | | |
| 6ᵛ | 62.0 *t* | 3.53 *m*<br>3.77 *m* | | |
| *β*-D-Glucopyranoside | | | | |
| 1ᵛⁱ | 105.4 *d* | 4.18 *d* | 8.4 | 6ⁱᵛ |
| 2ᵛⁱ | 74.6 *d* | 3.07 *t* | 8.4 | |
| 3ᵛⁱ | 77.3 *d* | 3.11 *t* | 8.4 | |
| 4ᵛⁱ | 71.1 *d* | 3.09 *t* | 8.4 | |
| 5ᵛⁱ | 77.0 *d* | 3.22 *m* | | |
| 6ᵛⁱ | 61.7 *t* | 3.55 *m*<br>3.77 *m* | | |

TO FIG. 33B

FROM FIG. 33A

FIG. 34

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 21.3 *t* | 1.16 *m*<br>1.46 *m* | | |
| 2 | 27.9 *t* | 1.69 *m*<br>1.88 *m* | | |
| 3 | 86.8 *d* | 3.36 *m* | | 1′ |
| 4 | 41.3 *s* | - | | |
| 5 | 140.8 *s* | - | | |
| 6 | 118.7 *d* | 5.52 *m* | | |
| 7 | 24.0 *t* | 1.87 *m*<br>2.27 *m* | | |
| 8 | 44.3 *d* | 1.85 *m* | | |
| 9 | 49.9 *s* | - | | |
| 10 | 35.8 *d* | 2.34 *m* | | |
| 11 | 214.8 *s* | - | | |
| 12 | 48.6 *t* | 2.29 *d*<br>3.01 *d* | 13.5 Hz | |
| 13 | 44.7 *s* | - | | |
| 14 | 34.9 *s* | - | | |
| 15 | 28.2 *t* | 1.24 *m*<br>1.33 *m* | | |
| 16 | 28.6 *t* | 1.45 *m*<br>2.04 *m* | | |
| 17 | 50.0 *d* | 1.69 *m* | | |
| 18 | 16.2 *q* | 0.66 *s* | (3H) | 12, 13, 14, 17 |
| 19 | 19.2 *q* | 0.96 *s* | (3H) | 8, 9, 10, 11 |
| 20 | 36.3 *d* | 1.32 *m* | | |
| 21 | 18.3 *q* | 0.84 *d* | 6.1 (3H) | 17, 20, 22 |
| 22 | 32.4 *t* | 1.30 *m*<br>1.52 *m* | | |
| 23 | 33.1 *t* | 1.38 *m*<br>1.45 *m* | | |
| 24 | 92.7 *d* | 3.31 *m* | | 1^IV |
| 25 | 72.9 *s* | - | | |
| 26 | 23.2 *q* | 1.05 *s* | (3H) | 24, 25, 27 |
| 27 | 25.8 *q* | 1.02 *s* | (3H) | 24, 25, 26 |
| 28 | 27.5 *q* | 0.97 *s* | (3H) | 3, 4, 5, 29 |
| 29 | 24.9 *q* | 1.13 *s* | (3H) | 3, 4, 5, 28 |
| 30 | 18.1 *q* | 1.02 *s* | (3H) | 8, 13, 14, 15 |

FIG. 35

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| 1' | 105.5 *d* | 4.19 *d* | 8.4 | 3 |
| 2' | 74.2 *d* | 3.08 *t* | 8.4 | |
| 3' | 77.0 *d* | 3.19 *t* | 8.4 | |
| 4' | 70.6 *d* | 3.17 *t* | 8.4 | |
| 5' | 76.0 *d* | 3.31 *m* | | |
| 6' | 68.7 *t* | 3.69 *m*<br>3.97 *m* | | |
| α-D-Glucopyranoside | | | | |
| 1'' | 98.9 *d* | 4.74 *d* | 3.4 | 4'' |
| 2'' | 73.0 *d* | 3.25 *dd* | 3.4, 8.4 | |
| 3'' | 77.3 *d* | 3.22 *t* | 8.4 | |
| 4'' | 70.4 *d* | 3.20 *t* | 8.4 | |
| 5'' | 75.4 *d* | 3.37 *m* | | |
| 6'' | 65.9 *t* | 3.63 *m*<br>3.85 *m* | | |
| *β*-D-Glucopyranoside | | | | |
| 1''' | 104.1 *d* | 4.31 *d* | 8.4 | 6' |
| 2''' | 74.1 *d* | 3.10 *t* | 8.4 | |
| 3''' | 76.7 *d* | 3.25 *t* | 8.4 | |
| 4''' | 74.1 *d* | 3.53 *t* | 8.4 | |
| 5''' | 76.8 *d* | 3.30 *m* | | |
| 6''' | 61.3 *t* | 3.59 *m*<br>3.70 *m* | | |
| *β*-D-Glucopyranoside | | | | |
| 1$^{iv}$ | 103.5 *d* | 4.34 *d* | 8.4 | 24 |
| 2$^{iv}$ | 79.7 *d* | 3.53 *t* | 8.4 | |
| 3$^{iv}$ | 77.8 *d* | 3.50 *t* | 8.4 | |
| 4$^{iv}$ | 70.2 *d* | 3.30 *t* | 8.4 | |
| 5$^{iv}$ | 75.5 *d* | 3.44 *m* | | |
| 6$^{iv}$ | 69.7 *t* | 3.45 *m*<br>4.18 *m* | | |
| *β*-D-Glucopyranoside | | | | |
| 1$^{v}$ | 103.4 *d* | 4.70 *d* | 8.4 | 2$^{iv}$ |
| 2$^{v}$ | 74.2 *d* | 3.14 *t* | 8.4 | |
| 3$^{v}$ | 77.4 *d* | 3.25 *t* | 8.4 | |
| 4$^{v}$ | 71.0 *d* | 3.14 *t* | 8.4 | |
| 5$^{v}$ | 77.4 *d* | 3.27 *m* | | |
| 6$^{v}$ | 61.9 *t* | 3.54 *m*<br>3.77 *m* | | |
| *β*-D-Glucopyranoside | | | | |
| 1$^{vi}$ | 104.1 *d* | 4.23 *d* | 8.4 | 6$^{iv}$ |
| 2$^{vi}$ | 73.6 *d* | 3.12 *t* | 8.4 | |
| 3$^{vi}$ | 77.6 *d* | 3.17 *t* | 8.4 | |
| 4$^{vi}$ | 71.2 *d* | 3.11 *t* | 8.4 | |
| 5$^{vi}$ | 76.7 *d* | 3.32 *m* | | |
| 6$^{vi}$ | 62.0 *t* | 3.54 *m*<br>3.73 *m* | | |

TO FIG. 37B

FROM FIG. 37A

FIG. 38

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 21.6 *t* | 1.14 *m*<br>1.45 *m* | | |
| 2 | 27.8 *t* | 1.67 *m*<br>1.85 *m* | | |
| 3 | 86.6 *d* | 3.39 *m* | | 1ʹ |
| 4 | 41.4 *s* | - | | |
| 5 | 140.7 *s* | - | | |
| 6 | 118.8 *d* | 5.51 *m* | | |
| 7 | 23.7 *t* | 1.85 *m*<br>2.32 *m* | | |
| 8 | 44.2 *d* | 1.85 *m* | | |
| 9 | 35.0 *s* | - | | |
| 10 | 35.0 *d* | 2.35 *m* | | |
| 11 | 214.8 *s* | - | | |
| 12 | 48.7 *t* | 2.30 *d*<br>3.01 *d* | 13.6<br>13.6 | |
| 13 | 49.5 *s* | - | | |
| 14 | 49.3 *s* | - | | |
| 15 | 28.1 *t* | 1.23 *m*<br>1.33 *m* | | |
| 16 | 28.5 *t* | 1.22 *m*<br>2.04 *m* | | |
| 17 | 49.9 *d* | 1.66 *m* | | |
| 18 | 16.0 *q* | 0.66 *s* | (3H) | 12, 13, 14, 17 |
| 19 | 19.4 *q* | 1.00 *s* | (3H) | 8, 9, 10, 11 |
| 20 | 36.1 *d* | 1.31 *m* | | |
| 21 | 18.1 *q* | 0.84 *d* | 6.4 (3H) | 17, 20, 22 |
| 22 | 33.1 *t* | 1.29 *m*<br>1.48 *m* | | |
| 23 | 33.0 *t* | 1.40 *m*<br>1.45 *m* | | |
| 24 | 92.2 *d* | 3.30 *m* | | 1ʹᵛ |
| 25 | 72.9 *s* | - | | |
| 26 | 23.0 *q* | 1.05 *s* | (3H) | 24, 25, 27 |
| 27 | 25.9 *q* | 1.02 *s* | (3H) | 24, 25, 26 |
| 28 | 27.7 *q* | 0.96 *s* | (3H) | 3, 4, 5, 29 |
| 29 | 25.2 *q* | 1.16 *s* | (3H) | 3, 4, 5, 28 |
| 30 | 18.4 *q* | 1.02 *s* | (3H) | 8, 13, 14, 15 |

FIG. 39

| Position | δC [ppm] | δH [ppm] | J [Hz]/ (INT) | HMBC (H ->C) |
|---|---|---|---|---|
| **Sugar moiety** | | | | |
| *β*-D-Glucopyranoside | | | | |
| 1ⁱ | 103.7 *d* | 4.31 *d* | 8.4 | 3 |
| 2ⁱ | 79.5 *d* | 3.51 *t* | 8.4 | |
| 3ⁱ | 77.8 *d* | 3.48 *t* | 8.4 | |
| 4ⁱ | 70.7 *d* | 3.23 *t* | 8.4 | |
| 5ⁱ | 76.1 *d* | 3.34 *m* | | |
| 6ⁱ | 68.9 *t* | 3.68 *m*<br>3.97 *m* | | |
| *β*-D-Glucopyranoside | | | | |
| 1ⁱⁱ | 103.2 *d* | 4.53 *d* | 8.4 | 2ⁱ |
| 2ⁱⁱ | 75.2 *d* | 3.14 *t* | 8.4 | |
| 3ⁱⁱ | 77.0 *d* | 3.25 *t* | 8.4 | |
| 4ⁱⁱ | 70.7 *d* | 3.18 *t* | 8.4 | |
| 5ⁱⁱ | 76.8 *d* | 3.10 *m* | | |
| 6ⁱⁱ | 62.6 *t* | 3.56 *m*<br>3.78 *m* | | |
| *β*-D-Glucopyranoside | | | | |
| 1ⁱⁱⁱ | 104.3 *d* | 4.31 *d* | 8.4 | 6ⁱ |
| 2ⁱⁱⁱ | 75.0 *d* | 3.07 *t* | 8.4 | |
| 3ⁱⁱⁱ | 77.0 *d* | 3.25 *t* | 8.4 | |
| 4ⁱⁱⁱ | 70.8 *d* | 3.15 *t* | 8.4 | |
| 5ⁱⁱⁱ | 77.0 *d* | 3.14 *m* | | |
| 6ⁱⁱⁱ | 62.0 *t* | 3.56 *m*<br>3.77 *m* | | |
| *β*-D-Glucopyranoside | | | | |
| 1ⁱᵛ | 103.4 *d* | 4.34 *d* | 8.4 | 24 |
| 2ⁱᵛ | 80.0 *d* | 3.54 *t* | 8.4 | |
| 3ⁱᵛ | 77.6 *d* | 3.52 *t* | 8.4 | |
| 4ⁱᵛ | 70.7 *d* | 3.23 *t* | 8.4 | |
| 5ⁱᵛ | 76.7 *d* | 3.40 *m* | | |
| 6ⁱᵛ | 69.1 *t* | 3.53 *m*<br>4.14 *m* | | |
| *β*-D-Glucopyranoside | | | | |
| 1ᵛ | 103.3 *d* | 4.71 *d* | 8.4 | 2ⁱᵛ |
| 2ᵛ | 73.6 *d* | 3.19 *t* | 8.4 | |
| 3ᵛ | 76.9 *d* | 3.17 *t* | 8.4 | |
| 4ᵛ | 70.8 *d* | 3.15 *t* | 8.4 | |
| 5ᵛ | 76.8 *d* | 3.10 *m* | | |
| 6ᵛ | 61.6 *t* | 3.58 *m*<br>3.75 *m* | | |
| *β*-D-Glucopyranoside | | | | |
| 1ᵛⁱ | 103.4 *t* | 4.19 *d* | 8.4 | 6ⁱᵛ |
| 2ᵛⁱ | 74.8 *d* | 3.10 *t* | 8.4 | |
| 3ᵛⁱ | 77.0 *d* | 3.25 *t* | 8.4 | |
| 4ᵛⁱ | 70.9 *d* | 3.11 *t* | 8.4 | |
| 5ᵛⁱ | 77.0 *d* | 3.14 *m* | | |
| 6ᵛⁱ | 62.2 *t* | 3.58 *m*<br>3.74 *m* | | |

TO FIG. 41B

FROM FIG. 41A

FIG. 42

| Position | $\delta_C$ [ppm] | $\delta_H$ [ppm] | J [Hz]/ (INT) | HMBC (H ->C) |
|---|---|---|---|---|
| Aglycon moiety | | | | |
| 1 | 26.0 *t* | 1.37 *m*<br>2.14 *m* | | |
| 2 | 28.7 *t* | 1.80 *m*<br>1.84 *m* | | |
| 3 | 87.2 *d* | 3.35 *m* | | 1' |
| 4 | 41.7 *s* | - | | |
| 5 | 143.8 *s* | - | | |
| 6 | 118.2 *d* | 5.39 *m* | | |
| 7 | 23.9 *t* | 1.70 *m*<br>2.28 *m* | | |
| 8 | 43.8 *d* | 1.57 *m* | | |
| 9 | 39.4 *s* | - | | |
| 10 | 35.8 *d* | 2.41 *m* | | |
| 11 | 78.4 *d* | 3.73 *m* | | |
| 12 | 40.7 *t* | 1.71 *m*<br>1.77 *m* | | |
| 13 | 47.6 *s* | - | | |
| 14 | 49.4 *s* | - | | |
| 15 | 33.8 *t* | 1.13 *m*<br>1.42 *m* | | |
| 16 | 28.1 *t* | 1.22 *m*<br>1.93 *m* | | |
| 17 | 51.0 *d* | 1.52 *m* | | |
| 18 | 15.6 *q* | 0.82 *s* | (3H) | 12, 13, 14, 17 |
| 19 | 25.3 *q* | 1.01 *s* | (3H) | 8, 9, 10, 11 |
| 20 | 36.5 *d* | 1.35 *m* | | |
| 21 | 18.4 *q* | 0.88 *d* | 6.1 (3H) | 17, 20, 22 |
| 22 | 30.0 *t* | 1.39 *m*<br>1.44 *m* | | |
| 23 | 33.2 *t* | 1.38 *m*<br>1.45 *m* | | |
| 24 | 92.1 *d* | 3.30 *m* | | 1^IV |
| 25 | 72.8 *s* | - | | |
| 26 | 22.9 *q* | 1.05 *s* | (3H) | 24, 25, 27 |
| 27 | 26.0 *q* | 1.02 *s* | (3H) | 24, 25, 26 |
| 28 | 27.1 *q* | 0.99 *s* | (3H) | 3, 4, 5, 29 |
| 29 | 25.4 *q* | 1.09 *s* | (3H) | 3, 4, 5, 28 |
| 30 | 19.0 *q* | 0.79 *s* | (3H) | 8, 13, 14, 15 |

FIG. 43

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| 1ⁱ | 105.2 *d* | 4.19 *d* | 8.4 | 3 |
| 2ⁱ | 74.2 *d* | 3.10 *t* | 8.4 | |
| 3ⁱ | 77.1 *d* | 3.20 *t* | 8.4 | |
| 4ⁱ | 74.8 *d* | 3.16 *t* | 8.4 | |
| 5ⁱ | 76.2 *d* | 3.33 *m* | | |
| 6ⁱ | 69.3 *t* | 3.71 *m*<br>3.96 *m* | | |
| *α*-D-Glucopyranoside | | | | |
| 1ⁱⁱ | 98.9 *d* | 4.75 *d* | 3.4 | 4ⁱⁱⁱ |
| 2ⁱⁱ | 72.8 *d* | 3.27 *dd* | 3.4, 8.4 | |
| 3ⁱⁱ | 76.9 *d* | 3.23 *t* | 8.4 | |
| 4ⁱⁱ | 70.4 *d* | 3.19 *t* | 8.4 | |
| 5ⁱⁱ | 76.1 *d* | 3.35 *m* | | |
| 6ⁱⁱ | 65.8 *t* | 3.63 *m*<br>3.86 *m* | | |
| *β*-D-Glucopyranoside | | | | |
| 1ⁱⁱⁱ | 104.1 *d* | 4.33 *d* | 8.4 | 6ⁱ |
| 2ⁱⁱⁱ | 74.1 *d* | 3.10 *t* | 8.4 | |
| 3ⁱⁱⁱ | 77.0 *d* | 3.26 *t* | 8.4 | |
| 4ⁱⁱⁱ | 74.3 *d* | 3.54 *t* | 8.4 | |
| 5ⁱⁱⁱ | 76.7 *d* | 3.29 *m* | | |
| 6ⁱⁱⁱ | 62.2 *t* | 3.59 *m*<br>3.71 *m* | | |
| *β*-D-Glucopyranoside | | | | |
| 1ⁱᵛ | 103.4 *d* | 4.34 *d* | 8.4 | 24 |
| 2ⁱᵛ | 80.5 *d* | 3.53 *t* | 8.4 | |
| 3ⁱᵛ | 77.8 *d* | 3.49 *t* | 8.4 | |
| 4ⁱᵛ | 70.6 *d* | 3.29 *t* | 8.4 | |
| 5ⁱᵛ | 75.6 *d* | 3.43 *m* | | |
| 6ⁱᵛ | 69.8 *t* | 3.53 *m*<br>4.19 *m* | | |
| *β*-D-Glucopyranoside | | | | |
| 1ᵛ | 103.5 *d* | 4.68 *d* | 8.4 | 2ⁱᵛ |
| 2ᵛ | 73.9 *d* | 3.18 *t* | 8.4 | |
| 3ᵛ | 77.5 *d* | 3.23 *t* | 8.4 | |
| 4ᵛ | 70.7 *d* | 3.16 *t* | 8.4 | |
| 5ᵛ | 77.5 *d* | 3.25 *m* | | |
| 6ᵛ | 61.7 *t* | 3.56 *m*<br>3.79 *m* | | |
| *β*-D-Glucopyranoside | | | | |
| 1ᵛⁱ | 104.2 *d* | 4.24 *d* | 8.4 | 6ⁱᵛ |
| 2ᵛⁱ | 73.7 *d* | 3.11 *t* | 8.4 | |
| 3ᵛⁱ | 77.5 *d* | 3.20 *t* | 8.4 | |
| 4ᵛⁱ | 71.1 *d* | 3.11 *t* | 8.4 | |
| 5ᵛⁱ | 76.6 *d* | 3.33 *m* | | |
| 6ᵛⁱ | 61.9 *t* | 3.56 *m*<br>3.74 *m* | | |

TO FIG. 45B

FROM FIG. 45A

FIG. 46

| Position | $\delta_C$ [ppm] | $\delta_H$ [ppm] | J [Hz]/ (INT) | HMBC (H ->C) |
|---|---|---|---|---|
| **Aglycon moiety** | | | | |
| 1 | 26.0 *t* | 1.37 *m*<br>2.14 *m* | | |
| 2 | 28.7 *t* | 1.80 *m*<br>1.84 *m* | | |
| 3 | 87.2 *d* | 3.38 *m* | | $1^{I}$ |
| 4 | 41.7 *s* | - | | |
| 5 | 143.8 *s* | - | | |
| 6 | 118.5 *d* | 5.40 *m* | | |
| 7 | 23.9 *t* | 1.70 *m*<br>2.29 *m* | | |
| 8 | 43.2 *d* | 1.57 *m* | | |
| 9 | 39.4 *s* | - | | |
| 10 | 36.0 *d* | 2.43 *m* | | |
| 11 | 78.4 *d* | 3.76 *m* | | |
| 12 | 40.7 *t* | 1.71 *m*<br>1.77 *m* | | |
| 13 | 47.6 *s* | - | | |
| 14 | 49.4 *s* | - | | |
| 15 | 33.8 *t* | 1.13 *m*<br>1.42 *m* | | |
| 16 | 28.1 *t* | 1.22 *m*<br>1.93 *m* | | |
| 17 | 50.7 *d* | 1.53 *m* | | |
| 18 | 15.6 *q* | 0.82 *s* | (3H) | 12, 13, 14, 17 |
| 19 | 25.3 *q* | 1.01 *s* | (3H) | 8, 9, 10 11 |
| 20 | 36.3 *d* | 1.37 *m* | | |
| 21 | 18.4 *q* | 0.88 *d* | 6.1 (3H) | 17, 20, 22 |
| 22 | 30.0 *t* | 1.39 *m*<br>1.44 *m* | | |
| 23 | 33.2 *t* | 1.38 *m*<br>1.45 *m* | | |
| 24 | 92.2 *d* | 3.30 *m* | | $1^{IV}$ |
| 25 | 72.8 *s* | - | | |
| 26 | 22.9 *q* | 1.05 *s* | (3H) | 24, 25, 27 |
| 27 | 26.0 *q* | 1.02 *s* | (3H) | 24, 25, 26 |
| 28 | 27.1 *q* | 0.99 *s* | (3H) | 3, 4, 5, 29 |
| 29 | 25.4 *q* | 1.09 *s* | (3H) | 3, 4, 5, 28 |
| 30 | 19.0 *q* | 0.79 *s* | (3H) | 8, 13, 14, 15 |

FIG. 47

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| 1' | 103.5 *d* | 4.19 *d* | 8.4 | 3 |
| 2' | 74.2 *d* | 3.11 *t* | 8.4 | |
| 3' | 77.1 *d* | 3.27 *t* | 8.4 | |
| 4' | 74.9 *d* | 3.55 *t* | 8.4 | |
| 5' | 76.4 *d* | 3.33 *m* | | |
| 6' | 68.9 *t* | 3.75 *m*<br>3.97 *m* | | |
| *β*-D-Glucopyranoside | | | | |
| 1'' | 103.5 *d* | 4.23 *d* | 8.4 | 4' |
| 2'' | 75.2 *d* | 3.14 *t* | 8.4 | |
| 3'' | 77.0 *d* | 3.25 *t* | 8.4 | |
| 4'' | 70.7 *d* | 3.18 *t* | 8.4 | |
| 5'' | 76.8 *d* | 3.10 *m* | | |
| 6'' | 62.0 *t* | 3.70 *m*<br>3.82 *m* | | |
| *β*-D-Glucopyranoside | | | | |
| 1''' | 103.3 *d* | 4.35 *d* | 8.4 | 6' |
| 2''' | 75.0 *d* | 3.07 *t* | 8.4 | |
| 3''' | 77.0 *d* | 3.25 *t* | 8.4 | |
| 4''' | 70.8 *d* | 3.15 *t* | 8.4 | |
| 5''' | 77.0 *d* | 3.14 *m* | | |
| 6''' | 61.6 *t* | 3.57 *m*<br>3.77 *m* | | |
| *β*-D-Glucopyranoside | | | | |
| $1^{iv}$ | 103.3 *d* | 4.34 *d* | 8.4 | 24 |
| $2^{iv}$ | 80.5 *d* | 3.51 *t* | 8.4 | |
| $3^{iv}$ | 77.6 *d* | 3.52 *t* | 8.4 | |
| $4^{iv}$ | 70.7 *d* | 3.23 *t* | 8.4 | |
| $5^{iv}$ | 76.7 *d* | 3.40 *m* | | |
| $6^{iv}$ | 68.9 *t* | 3.54 *m*<br>4.15 *m* | | |
| *β*-D-Glucopyranoside | | | | |
| $1^{v}$ | 103.4 *d* | 4.69 *d* | 8.4 | $2^{iv}$ |
| $2^{v}$ | 73.6 *d* | 3.19 *t* | 8.4 | |
| $3^{v}$ | 76.9 *d* | 3.17 *t* | 8.4 | |
| $4^{v}$ | 70.8 *d* | 3.15 *t* | 8.4 | |
| $5^{v}$ | 76.8 *d* | 3.10 *m* | | |
| $6^{v}$ | 61.6 *t* | 3.58 *m*<br>3.77 *m* | | |
| *β*-D-Glucopyranoside | | | | |
| $1^{vi}$ | 105.3 *d* | 4.19 *d* | 8.4 | $6^{iv}$ |
| $2^{vi}$ | 74.8 *d* | 3.10 *t* | 8.4 | |
| $3^{vi}$ | 77.0 *d* | 3.25 *t* | 8.4 | |
| $4^{vi}$ | 70.9 *d* | 3.11 *t* | 8.4 | |
| $5^{vi}$ | 77.0 *d* | 3.14 *m* | | |
| $6^{vi}$ | 61.8 *t* | 3.58 *m*<br>3.74 *m* | | |

TO FIG. 49B

FROM FIG. 49A

FIG. 50

| Position | $\delta_C$ [ppm] | $\delta_H$ [ppm] | J [Hz]/ (INT) | HMBC (H ->C) |
|---|---|---|---|---|
| **Aglycon moiety** | | | | |
| 1 | 26.0 *t* | 1.37 *m*<br>2.14 *m* | | |
| 2 | 28.7 *t* | 1.80 *m*<br>1.84 *m* | | |
| 3 | 87.2 *d* | 3.35 *m* | | 1' |
| 4 | 41.7 *s* | - | | |
| 5 | 143.8 *s* | - | | |
| 6 | 118.2 *d* | 5.39 *m* | | |
| 7 | 23.9 *t* | 1.70 *m*<br>2.28 *m* | | |
| 8 | 43.8 *d* | 1.57 *m* | | |
| 9 | 39.4 *s* | - | | |
| 10 | 35.8 *d* | 2.41 *m* | | |
| 11 | 78.4 *d* | 3.73 *m* | | |
| 12 | 40.7 *t* | 1.71 *m*<br>1.77 *m* | | |
| 13 | 47.6 *s* | - | | |
| 14 | 49.4 *s* | - | | |
| 15 | 33.8 *t* | 1.13 *m*<br>1.42 *m* | | |
| 16 | 28.1 *t* | 1.22 *m*<br>1.93 *m* | | |
| 17 | 51.0 *d* | 1.52 *m* | | |
| 18 | 15.6 *q* | 0.82 *s* | (3H) | 12, 13, 14, 17 |
| 19 | 25.3 *q* | 1.01 *s* | (3H) | 8, 9, 10, 11 |
| 20 | 36.5 *d* | 1.35 *m* | | |
| 21 | 18.4 *q* | 0.88 *d* | 6.1 (3H) | 17, 20, 22 |
| 22 | 30.0 *t* | 1.39 *m*<br>1.44 *m* | | |
| 23 | 33.2 *t* | 1.38 *m*<br>1.45 *m* | | |
| 24 | 92.1 *d* | 3.30 *m* | | 1$^{IV}$ |
| 25 | 72.8 *s* | - | | |
| 26 | 22.9 *q* | 1.05 *s* | (3H) | 24, 25, 27 |
| 27 | 26.0 *q* | 1.02 *s* | (3H) | 24, 25, 26 |
| 28 | 27.1 *q* | 0.99 *s* | (3H) | 3, 4, 5, 29 |
| 29 | 25.4 *q* | 1.09 *s* | (3H) | 3, 4, 5, 28 |
| 30 | 19.0 *q* | 0.79 *s* | (3H) | 8, 13, 14, 15 |

FIG. 51

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| $1^{I}$ | 103.6 *d* | 4.32 *d* | 8.4 | 3 |
| $2^{I}$ | 79.6 *d* | 3.51 *t* | 8.4 | |
| $3^{I}$ | 77.8 *d* | 3.49 *t* | 8.4 | |
| $4^{I}$ | 70.7 *d* | 3.23 *t* | 8.4 | |
| $5^{I}$ | 76.1 *d* | 3.34 *m* | | |
| $6^{I}$ | 68.9 *t* | 3.70 *m*<br>3.97 *m* | | |
| *β*-D-Glucopyranoside | | | | |
| $1^{II}$ | 103.0 *d* | 4.56 *d* | 8.4 | $2^{I}$ |
| $2^{II}$ | 75.2 *d* | 3.14 *t* | 8.4 | |
| $3^{II}$ | 77.0 *d* | 3.25 *t* | 8.4 | |
| $4^{II}$ | 70.7 *d* | 3.18 *t* | 8.4 | |
| $5^{II}$ | 76.8 *d* | 3.10 *m* | | |
| $6^{II}$ | 61.8 *t* | 3.56 *m*<br>3.78 *m* | | |
| *β*-D-Glucopyranoside | | | | |
| $1^{III}$ | 103.9 *d* | 4.32 *d* | 8.4 | $6^{I}$ |
| $2^{III}$ | 75.0 *d* | 3.07 *t* | 8.4 | |
| $3^{III}$ | 77.0 *d* | 3.25 *t* | 8.4 | |
| $4^{III}$ | 70.8 *d* | 3.15 *t* | 8.4 | |
| $5^{III}$ | 77.0 *d* | 3.14 *m* | | |
| $6^{III}$ | 61.8 *t* | 3.56 *m*<br>3.77 *m* | | |
| *β*-D-Glucopyranoside | | | | |
| $1^{IV}$ | 103.5 *d* | 4.34 *d* | 8.4 | 24 |
| $2^{IV}$ | 79.7 *d* | 3.54 *t* | 8.4 | |
| $3^{IV}$ | 77.6 *d* | 3.52 *t* | 8.4 | |
| $4^{IV}$ | 70.7 *d* | 3.23 *t* | 8.4 | |
| $5^{IV}$ | 76.7 *d* | 3.40 *m* | | |
| $6^{IV}$ | 69.1 *t* | 3.52 *m*<br>4.15 *m* | | |
| *β*-D-Glucopyranoside | | | | |
| $1^{V}$ | 103.4 *d* | 4.69 *d* | 8.4 | $2^{IV}$ |
| $2^{V}$ | 73.6 *d* | 3.19 *t* | 8.4 | |
| $3^{V}$ | 76.9 *d* | 3.17 *t* | 8.4 | |
| $4^{V}$ | 70.8 *d* | 3.15 *t* | 8.4 | |
| $5^{V}$ | 76.8 *d* | 3.10 *m* | | |
| $6^{V}$ | 61.6 *t* | 3.58 *m*<br>3.75 *m* | | |
| *β*-D-Glucopyranoside | | | | |
| $1^{VI}$ | 103.3 *d* | 4.19 *d* | 8.4 | $6^{IV}$ |
| $2^{VI}$ | 74.8 *d* | 3.10 *t* | 8.4 | |
| $3^{VI}$ | 77.0 *d* | 3.25 *t* | 8.4 | |
| $4^{VI}$ | 70.9 *d* | 3.11 *t* | 8.4 | |
| $5^{VI}$ | 77.0 *d* | 3.14 *m* | | |
| $6^{VI}$ | 61.8 *t* | 3.58 *m*<br>3.74 *m* | | |

TO FIG. 53B

FROM FIG. 53A

FIG. 54

| Position | $\delta_C$ [ppm] | $\delta_H$ [ppm] | J [Hz]/ (INT) | HMBC (H ->C) |
|---|---|---|---|---|
| **Aglycon moiety** | | | | |
| 1 | 21.8 *t* | 1.15 *m*<br>1.48 *m* | | |
| 2 | 28.2 *t* | 1.70 *m*<br>1.89 *m* | | |
| 3 | 86.6 *d* | 3.33 *m* | | $1^{I}$ |
| 4 | 41.2 *s* | - | | |
| 5 | 140.9 *s* | - | | |
| 6 | 118.7 *d* | 5.52 *m* | | |
| 7 | 23.7 *t* | 1.85 *m*<br>2.28 *m* | | |
| 8 | 44.4 *d* | 1.86 *m* | | |
| 9 | 50.0 *s* | - | | |
| 10 | 35.4 *d* | 2.33 *m* | | |
| 11 | 214.9 *d* | - | | |
| 12 | 48.9 *t* | 2.30 *m*<br>3.01 *m* | | |
| 13 | 44.6 *s* | - | | |
| 14 | 34.9 *s* | - | | |
| 15 | 28.5 *t* | 1.24 *m*<br>1.35 *m* | | |
| 16 | 28.6 *t* | 1.46 *m*<br>2.03 *m* | | |
| 17 | 50.1 *d* | 1.72 *m* | | |
| 18 | 16.3 *q* | 0.66 *s* | (3H) | 12, 13, 14, 17 |
| 19 | 19.0 *q* | 0.96 *s* | (3H) | 8, 9, 10, 11 |
| 20 | 36.4 *d* | 1.32 *m* | | |
| 21 | 18.1 *q* | 0.85 *d* | 6.1 (3H) | 17, 20, 22 |
| 22 | 32.8 *t* | 1.30 *m*<br>1.54 *m* | | |
| 23 | 33.2 *t* | 1.38 *m*<br>1.45 *m* | | |
| 24 | 92.5 *d* | 3.32 *m* | | $1^{IV}$ |
| 25 | 72.7 *s* | - | | |
| 26 | 23.0 *q* | 1.05 *s* | (3H) | 24, 25, 27 |
| 27 | 25.8 *q* | 1.02 *s* | (3H) | 24, 25, 26 |
| 28 | 27.4 *q* | 0.97 *s* | (3H) | 3, 4, 5, 29 |
| 29 | 24.9 *q* | 1.13 *s* | (3H) | 3, 4, 5, 28 |
| 30 | 18.0 *q* | 1.02 *s* | (3H) | 8, 13, 14, 15 |

FIG. 55

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| $1^{i}$ | 103.2 *d* | 4.19 *d* | 8.4 | 3 |
| $2^{i}$ | 74.2 *d* | 3.11 *t* | 8.4 | |
| $3^{i}$ | 76.9 *d* | 3.25 *t* | 8.4 | |
| $4^{i}$ | 74.2 *d* | 3.56 *t* | 8.4 | |
| $5^{i}$ | 76.0 *d* | 3.36 *m* | | |
| $6^{i}$ | 69.2 *t* | 3.69 *m*<br>3.97 *m* | | |
| *α*-D-Glucopyranoside | | | | |
| $1^{ii}$ | 99.0 *d* | 4.76 *d* | 3.4 | $4^{i}$ |
| $2^{ii}$ | 73.2 *d* | 3.27 *dd* | 3.4, 8.4 | |
| $3^{ii}$ | 76.5 *d* | 3.32 *t* | 8.4 | |
| $4^{ii}$ | 70.4 *d* | 3.27 *t* | 8.4 | |
| $5^{ii}$ | 75.3 *d* | 3.36 *m* | | |
| $6^{ii}$ | 65.8 *t* | 3.64 *m*<br>3.87 *m* | | |
| *β*-D-Glucopyranoside | | | | |
| $1^{iii}$ | 104.2 *d* | 4.33 *d* | 8.4 | $6^{i}$ |
| $2^{iii}$ | 74.8 *d* | 3.12 *t* | 8.4 | |
| $3^{iii}$ | 77.4 *d* | 3.19 *t* | 8.4 | |
| $4^{iii}$ | 70.5 *d* | 3.17 *t* | 8.4 | |
| $5^{iii}$ | 77.5 *d* | 3.24 *m* | | |
| $6^{iii}$ | 61.4 *t* | 3.55 *m*<br>3.75 *m* | | |
| *β*-D-Glucopyranoside | | | | |
| $1^{iv}$ | 103.5 *d* | 4.34 *d* | 8.4 | 24 |
| $2^{iv}$ | 79.6 *d* | 3.54 *t* | 8.4 | |
| $3^{iv}$ | 77.6 *d* | 3.50 *t* | 8.4 | |
| $4^{iv}$ | 70.3 *d* | 3.32 *t* | 8.4 | |
| $5^{iv}$ | 76.0 *d* | 3.34 *m* | | |
| $6^{iv}$ | 69.0 *t* | 3.52 *m*<br>4.14 *m* | | |
| *β*-D-Glucopyranoside | | | | |
| $1^{v}$ | 103.3 *d* | 4.71 *d* | 8.4 | $2^{iv}$ |
| $2^{v}$ | 74.8 *d* | 3.18 *t* | 8.4 | |
| $3^{v}$ | 77.0 *d* | 3.27 *t* | 8.4 | |
| $4^{v}$ | 70.4 *d* | 3.23 *t* | 8.4 | |
| $5^{v}$ | 77.2 *d* | 3.22 *m* | | |
| $6^{v}$ | 61.2 *d* | 3.59 *m*<br>3.71 *m* | | |
| *β*-D-Glucopyranoside | | | | |
| $1^{vi}$ | 105.4 *d* | 4.20 *d* | 8.4 | $6^{iv}$ |
| $2^{vi}$ | 74.6 *d* | 3.08 *t* | 8.4 | |
| $3^{vi}$ | 76.9 *d* | 3.17 *t* | 8.4 | |
| $4^{vi}$ | 70.8 *d* | 3.14 *t* | 8.4 | |
| $5^{vi}$ | 76.3 *d* | 3.23 *m* | | |
| $6^{vi}$ | 61.8 *t* | 3.55 *m*<br>3.76 *m* | | |

TO FIG. 57B

FROM FIG. 57A

FIG. 58

| Position | $\delta_C$ [ppm] | $\delta_H$ [ppm] | J [Hz]/ (INT) | HMBC (H ->C) |
|---|---|---|---|---|
| **Aglycon moiety** | | | | |
| 1 | 25.9 *t* | 1.38 *m*<br>2.13 *m* | | |
| 2 | 28.7 *t* | 1.80 *m*<br>1.84 *m* | | |
| 3 | 87.3 *d* | 3.37 *m* | | $1'$ |
| 4 | 41.8 *s* | - | | |
| 5 | 143.6 *s* | - | | |
| 6 | 118.4 *d* | 5.39 *m* | | |
| 7 | 23.9 *t* | 1.70 *m*<br>2.28 *m* | | |
| 8 | 43.7 *d* | 1.57 *m* | | |
| 9 | 39.4 *s* | - | | |
| 10 | 35.8 *d* | 2.40 *m* | | |
| 11 | 78.4 *d* | 3.76 *m* | | |
| 12 | 40.6 *t* | 1.71 *m*<br>1.77 *m* | | |
| 13 | 47.6 *s* | - | | |
| 14 | 49.1 *s* | - | | |
| 15 | 33.8 *t* | 1.12 *m*<br>1.42 *m* | | |
| 16 | 28.1 *t* | 1.22 *m*<br>1.93 *m* | | |
| 17 | 50.9 *d* | 1.52 *m* | | |
| 18 | 15.6 *q* | 0.82 *s* | (3H) | 12, 13, 14, 17 |
| 19 | 25.3 *q* | 1.01 *s* | (3H) | 8, 9, 10, 11 |
| 20 | 36.5 *d* | 1.35 *m* | | |
| 21 | 18.4 *q* | 0.88 *d* | 6.1 (3H) | 17, 20, 22 |
| 22 | 30.0 *t* | 1.39 *m*<br>1.44 *m* | | |
| 23 | 33.2 *t* | 1.38 *m*<br>1.45 *m* | | |
| 24 | 92.1 *d* | 3.30 *m* | | $1^{IV}$ |
| 25 | 72.8 *s* | - | | |
| 26 | 22.9 *q* | 1.05 *s* | (3H) | 24, 25, 27 |
| 27 | 26.0 *q* | 1.02 *s* | (3H) | 24, 25, 26 |
| 28 | 27.1 *q* | 0.99 *s* | (3H) | 3, 4, 5, 29 |
| 29 | 25.4 *q* | 1.09 *s* | (3H) | 3, 4, 5, 28 |
| 30 | 19.0 *q* | 0.79 *s* | (3H) | 8, 13, 14, 15 |

FIG. 59

| Position | $\delta_C$ [ppm] | $\delta_H$ [ppm] | J [Hz]/ (INT) | HMBC (H ->C) |
|---|---|---|---|---|
| **Sugar moiety** | | | | |
| *β*-D-Glucopyranoside | | | | |
| $1^{I}$ | 103.5 *d* | 4.19 *d* | 8.4 | 3 |
| $2^{I}$ | 74.2 *d* | 3.11 *t* | 8.4 | |
| $3^{I}$ | 77.1 *d* | 3.27 *t* | 8.4 | |
| $4^{I}$ | 74.8 *d* | 3.56 *t* | 8.4 | |
| $5^{I}$ | 76.4 *d* | 3.33 *m* | | |
| $6^{I}$ | 69.3 *t* | 3.71 *m*<br>3.96 *m* | | |
| *α*-D-Glucopyranoside | | | | |
| $1^{II}$ | 99.0 *d* | 4.76 *d* | 3.4 | $4^{I}$ |
| $2^{II}$ | 72.8 *d* | 3.27 *dd* | 3.4, 8.4 | |
| $3^{II}$ | 76.9 *d* | 3.31 *t* | 8.4 | |
| $4^{II}$ | 70.4 *d* | 3.31 *t* | 8.4 | |
| $5^{II}$ | 76.1 *d* | 3.35 *m* | | |
| $6^{II}$ | 65.8 *t* | 3.63 *m*<br>3.86 *m* | | |
| *β*-D-Glucopyranoside | | | | |
| $1^{III}$ | 105.3 *d* | 4.20 *d* | 8.4 | $6^{I}$ |
| $2^{III}$ | 74.1 *d* | 3.10 *t* | 8.4 | |
| $3^{III}$ | 77.4 *d* | 3.29 *t* | 8.4 | |
| $4^{III}$ | 70.7 *d* | 3.20 *t* | 8.4 | |
| $5^{III}$ | 76.7 *d* | 3.22 *m* | | |
| $6^{III}$ | 62.2 *t* | 3.56 *m*<br>3.77 *m* | | |
| *β*-D-Glucopyranoside | | | | |
| $1^{IV}$ | 103.4 *d* | 4.34 *d* | 8.4 | 24 |
| $2^{IV}$ | 80.5 *d* | 3.53 *t* | 8.4 | |
| $3^{IV}$ | 77.8 *d* | 3.49 *t* | 8.4 | |
| $4^{IV}$ | 70.6 *d* | 3.23 *t* | 8.4 | |
| $5^{IV}$ | 76.6 *d* | 3.41 *m* | | |
| $6^{IV}$ | 68.9 *t* | 3.53 *m*<br>4.15 *m* | | |
| *β*-D-Glucopyranoside | | | | |
| $1^{V}$ | 103.5 *d* | 4.68 *d* | 8.4 | $2^{IV}$ |
| $2^{V}$ | 73.9 *d* | 3.18 *t* | 8.4 | |
| $3^{V}$ | 77.5 *d* | 3.23 *t* | 8.4 | |
| $4^{V}$ | 70.7 *d* | 3.16 *t* | 8.4 | |
| $5^{V}$ | 77.5 *d* | 3.20 *m* | | |
| $6^{V}$ | 61.7 *t* | 3.62 *m*<br>3.69 *m* | | |
| *β*-D-Glucopyranoside | | | | |
| $1^{VI}$ | 104.2 *d* | 4.35 *d* | 8.4 | $6^{IV}$ |
| $2^{VI}$ | 73.7 *d* | 3.11 *t* | 8.4 | |
| $3^{VI}$ | 76.5 *d* | 3.23 *t* | 8.4 | |
| $4^{VI}$ | 71.1 *d* | 3.11 *t* | 8.4 | |
| $5^{VI}$ | 76.6 *d* | 3.17 *m* | | |
| $6^{VI}$ | 61.9 *t* | 3.56 *m*<br>3.74 *m* | | |

MOGROSIDES AND USE THEREOF

Field of the Invention

The invention relates to a process for purification of mogrosides from *Siraitia grosvenorii* fruit extract, and their applications in foods, beverage and other consumables.

Description of the Related Art

Luo han guo generally refers to a fruit of *Siraitia grosvenorii*, a member of the Cucurbitaceae family, which is a plant native to some regions of southern Asia and China. The sweet taste of luo han guo mainly comes from triterpene glycosides generally known as mogrosides or mogrol glycosides. Mogrosides comprise only about 1% of the luo han guo fruit. There are a number of mogrosides identified in luo han guo but generally mogroside V (CAS No: 88901-36-4) has the highest concentration compared to others (Table 1). Mogrol glycosides have the same core molecule—mogrol or oxo-mogrol and differ from each other by number and type of glycosidic residues bonded to mogrol or oxo-mogrol molecules.

TABLE 1

Mogrosides present in Luo han guo fruits

| Substance | Mol. Formula | Mol. Weight |
|---|---|---|
| Mogroside IIE | C42H12O14 | 801.01 |
| Mogroside III | C4sHs2O19 | 963.15 |
| Mogroside IV | Cs4H92O24 | 1125.29 |
| Mogroside V | C60H102O29 | 1287.43 |
| Mogroside VI | C66H112O34 | 1449.58 |
| 11-oxo-Mogroside V | C60H100O29 | 1285.42 |
| Siamenoside I | Cs4H92O24 | 1125.29 |
| Grosmomoside I | Cs4H92O24 | 1125.29 |

Various extraction techniques are used to isolate mogrosides from luo han guo fruits. As a result luo han guo powdered extracts are being prepared which usually contain 30-65% w/w of total mogrosides, and mogroside V content of those materials can vary as much as 18-55%. Such extracts generally cannot be widely used in foods and beverages as they possess undesirable organoleptic properties.

Hence there is a need for compositions comprising mogroside molecules with significantly improved organoleptic characteristics allowing their wider usage in foods, beverages and other consumables.

No techniques are currently available for purifying mogrosides. Therefore, there is a need for a process of for purification of novel high purity mogrosides from *Siraitia grosvenori* fruit extract.

BRIEF DESCRIPTION OF THE DRAWINGS

FIG. 30: NMR data of compound 8
FIG. 31: NMR data of compound 8 (continued)
FIG. 34: NMR data of compound 9
FIG. 35: NMR data of compound 9 (continued)
FIG. 38: NMR data of compound 10
FIG. 39: NMR data of compound 10 (continued)
FIG. 42: NMR data of compound 11
FIG. 43: NMR data of compound 11 (continued)
FIG. 46: NMR data of compound 12
FIG. 47: NMR data of compound 12 (continued)
FIG. 50: NMR data of compound 13
FIG. 51: NMR data of compound 13 (continued)
FIG. 54: NMR data of compound 14
FIG. 55: NMR data of compound 14 (continued)
FIG. 58: NMR data of compound 15
FIG. 59: NMR data of compound 15 (continued)

SUMMARY OF THE INVENTION

The invention relates to a process for preparation of compositions comprising mogrosides from *Siraitia grosvenori* fruit extract.

In one embodiment, the process for purification of mogrosides comprises methods described in U.S. Patent Application No. 61/379,729 (filed Sep. 3, 2010), U.S. patent application Ser. No. 13/219,721 (filed Aug. 29, 2011), now patented as U.S. Pat. No. 9,101,162, and U.S. patent application Ser. No. 14/792,594 (filed Jul. 6, 2015), which was published as US Patent Application Publication No. 2015/0305381, which are incorporated by reference herein in their entirety.

In yet another embodiment the process further comprises:

a. providing a mixture of mogrosides;

b. dissolving the mogrosides mixture in solvent to form an initial solution of mogrosides;

c. passing the initial solution through a chromatographic system, d. separating the fractions comprising mogroside compounds 1-15.

The present invention further provides compositions comprising mogroside compounds 1-15.

In one embodiment the compositions further comprise another high intensity sweetener selected from the group consisting of stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside 0, dulcoside A, dulcoside B, rubusoside, other steviol glycosides occurring in *Stevia rebaudiana* plant, glycosylated steviol glycosides, biosynthetic steviol glycosides, Luo Han Guo sweetener, siamenoside, mogroside IV, mogroside V, mogroside VI, other mogrosides occurring in *Siraitia grosvenorii* fruits, monatin and its salts (monatin SS, RR, RS, SR), glycyrrhizic acid and its salts, curculin, thaumatin, monellin, mabinlin, brazzein, hemandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and combinations thereof.

The present invention also provides consumables comprising mogroside compounds 1-15.

In one embodiment the consumable is selected from the group consisting of food, beverage, pharmaceutical composition, tobacco, nutraceutical, oral hygienic composition, or cosmetic.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention provides a process for purification of mogroside compounds 1-15 from *Siraitia grosvenorii* fruit.

Figure 1:
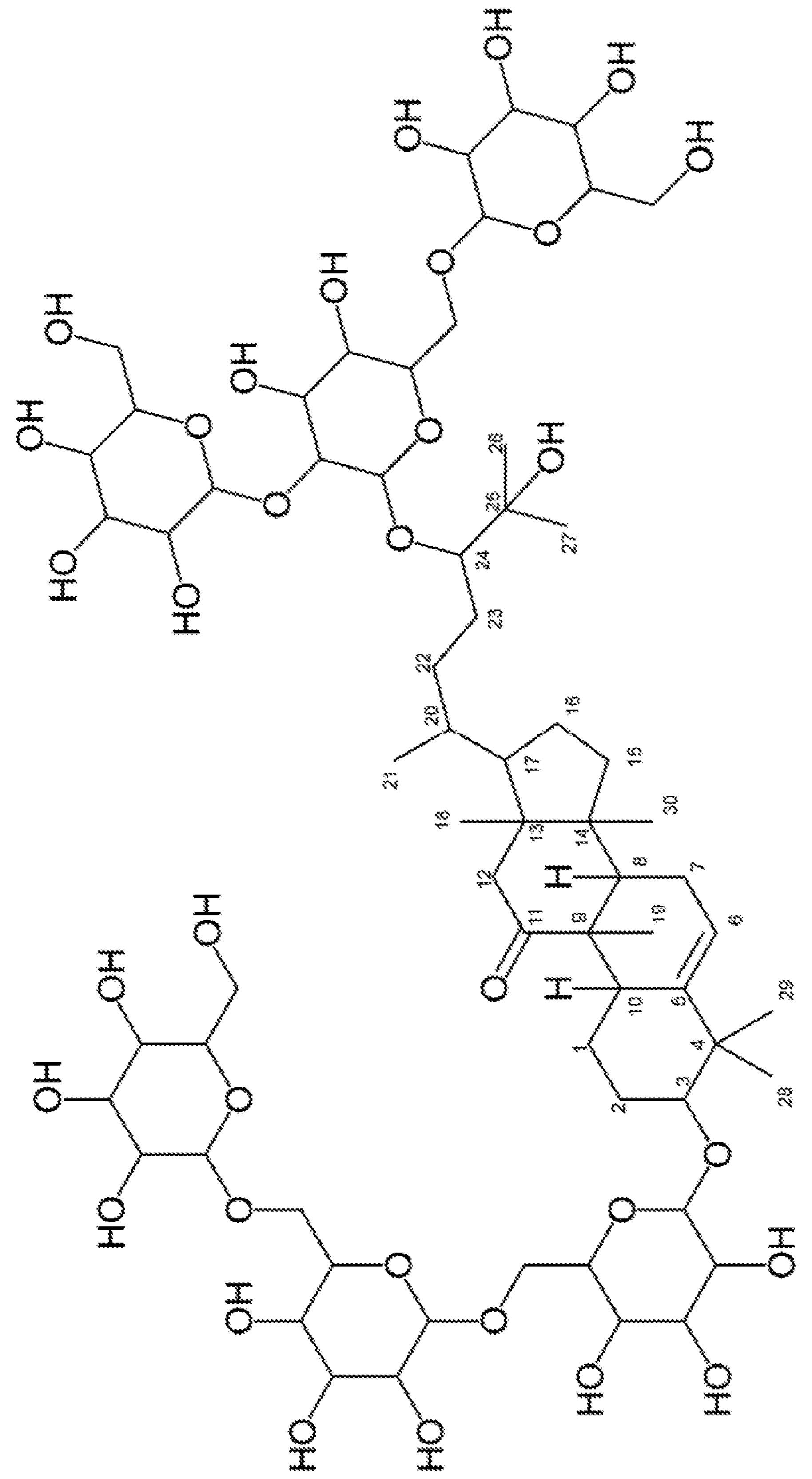
FIG. 1: Chemical structure of mogroside compound 1
Figure 2:
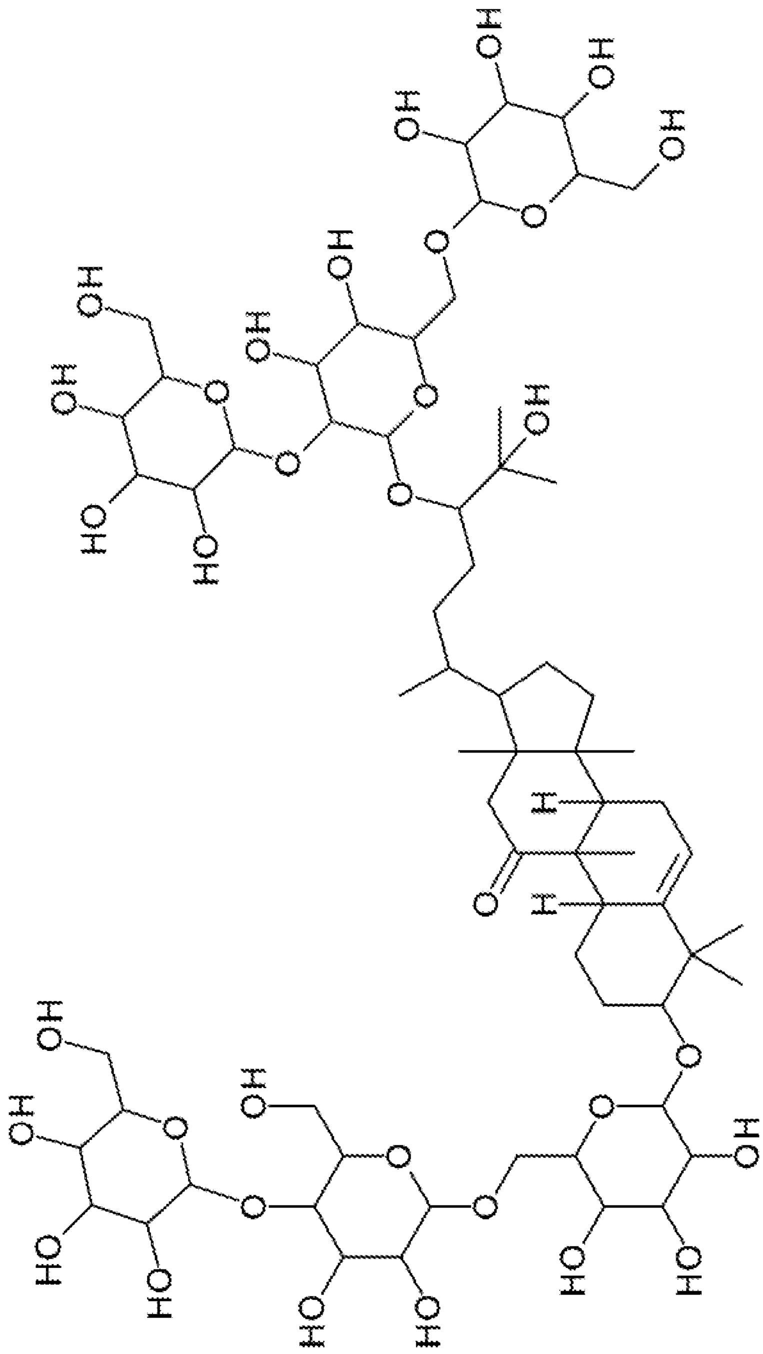
FIG. 2: Chemical structure of mogroside compound 2
Figure 3:
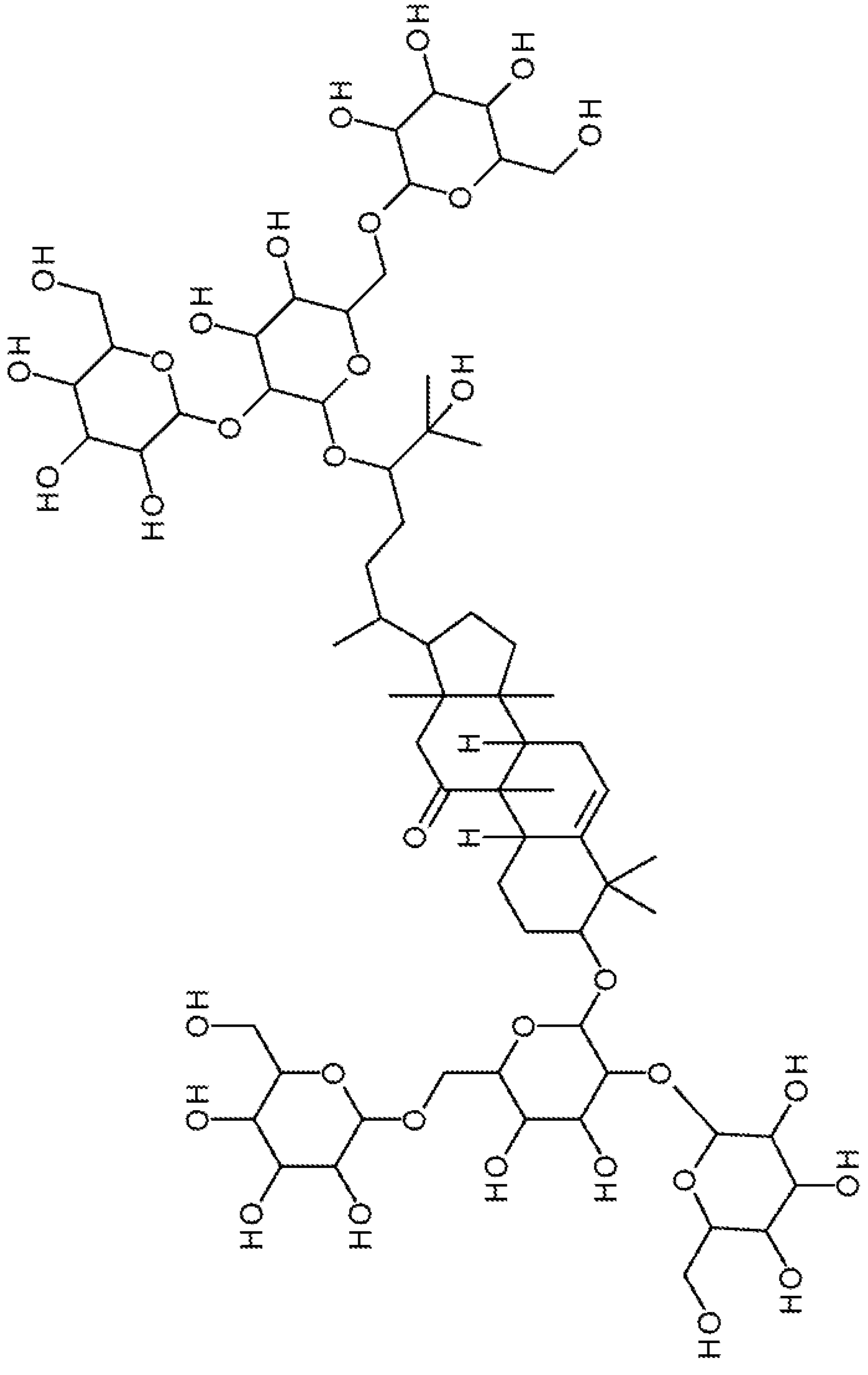
FIG. 3: Chemical structure of mogroside compound 3
Figure 4:
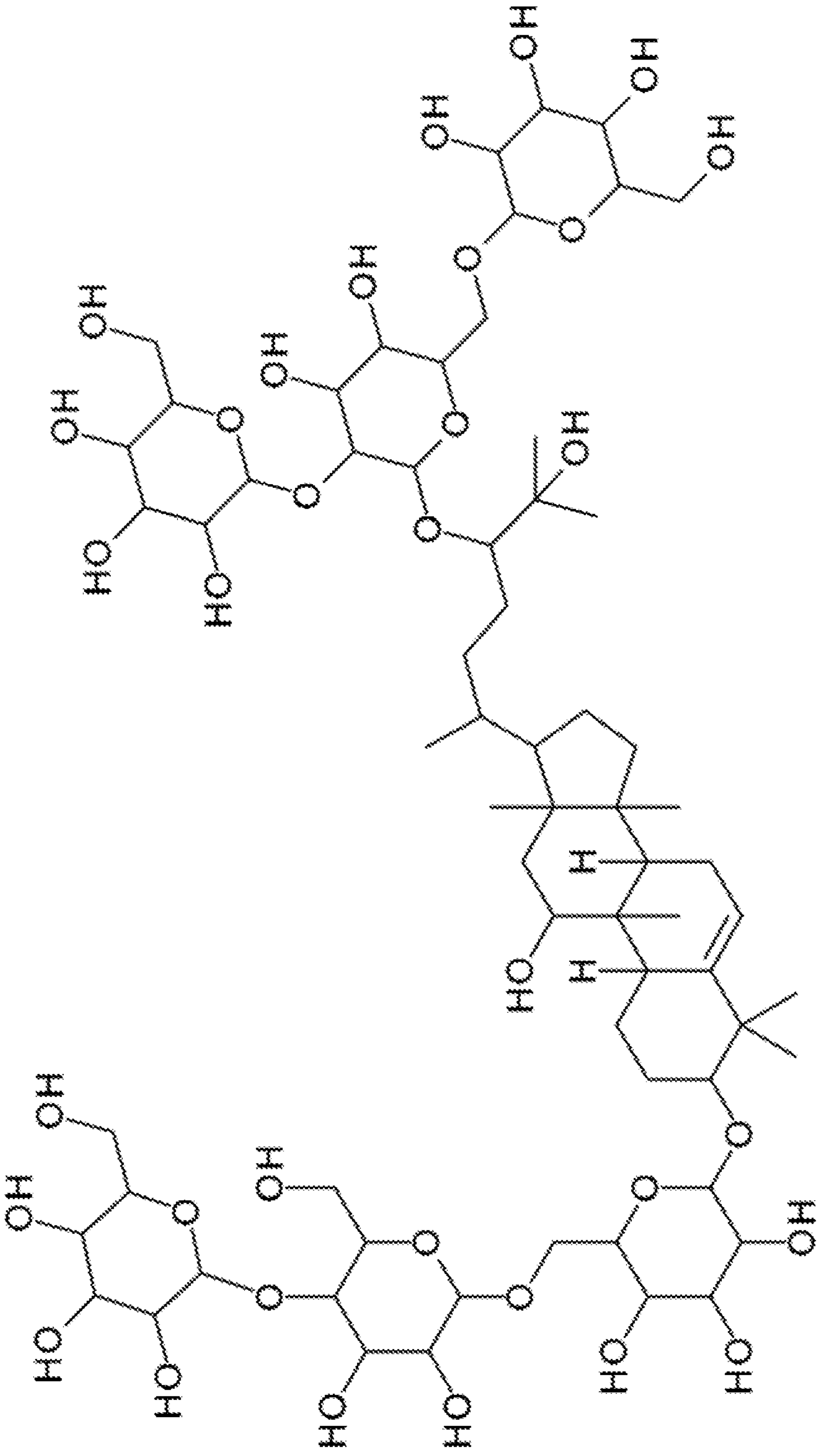
FIG. 4: Chemical structure of mogroside compound 4
Figure 5:
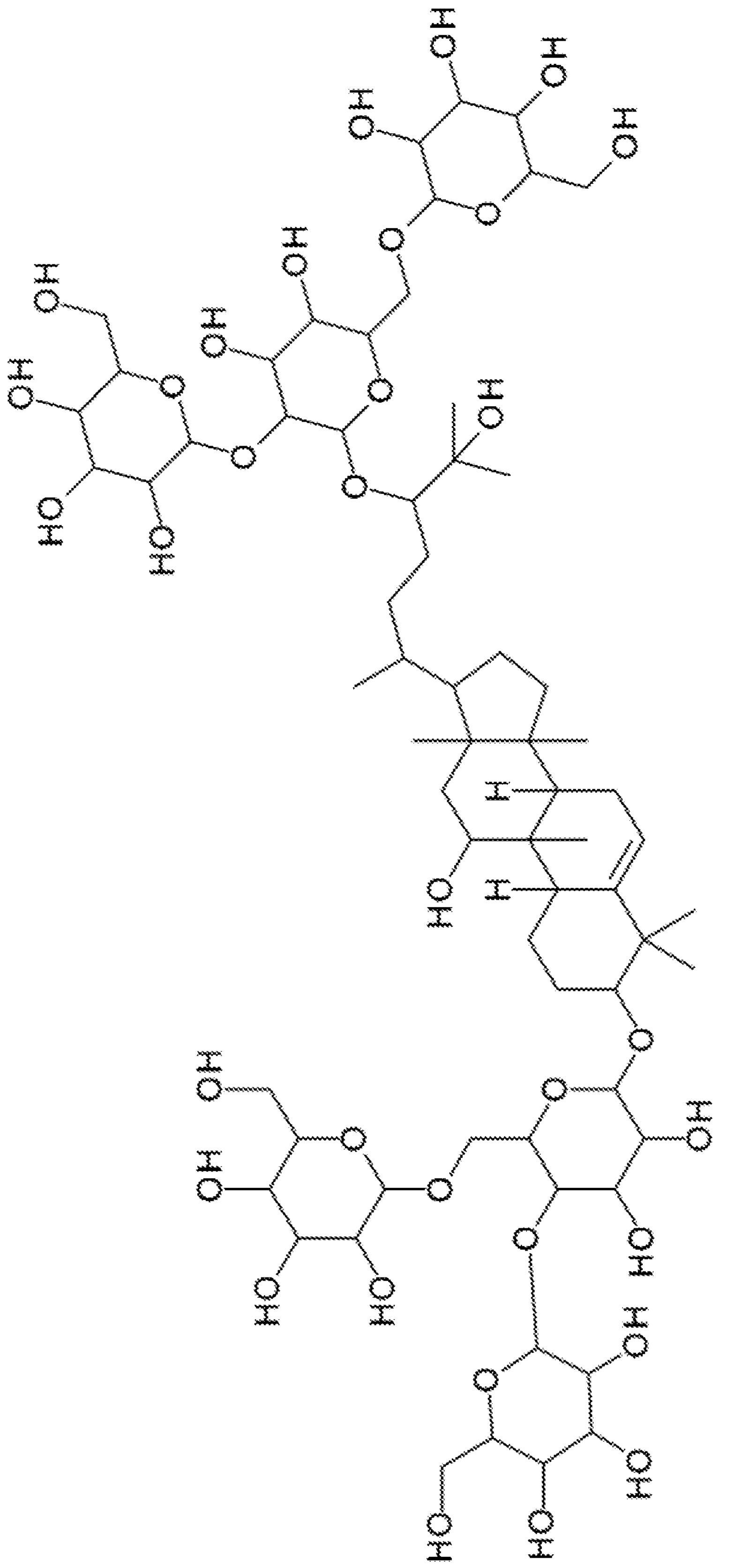
FIG. 5: Chemical structure of mogroside compound 5
Figure 6:
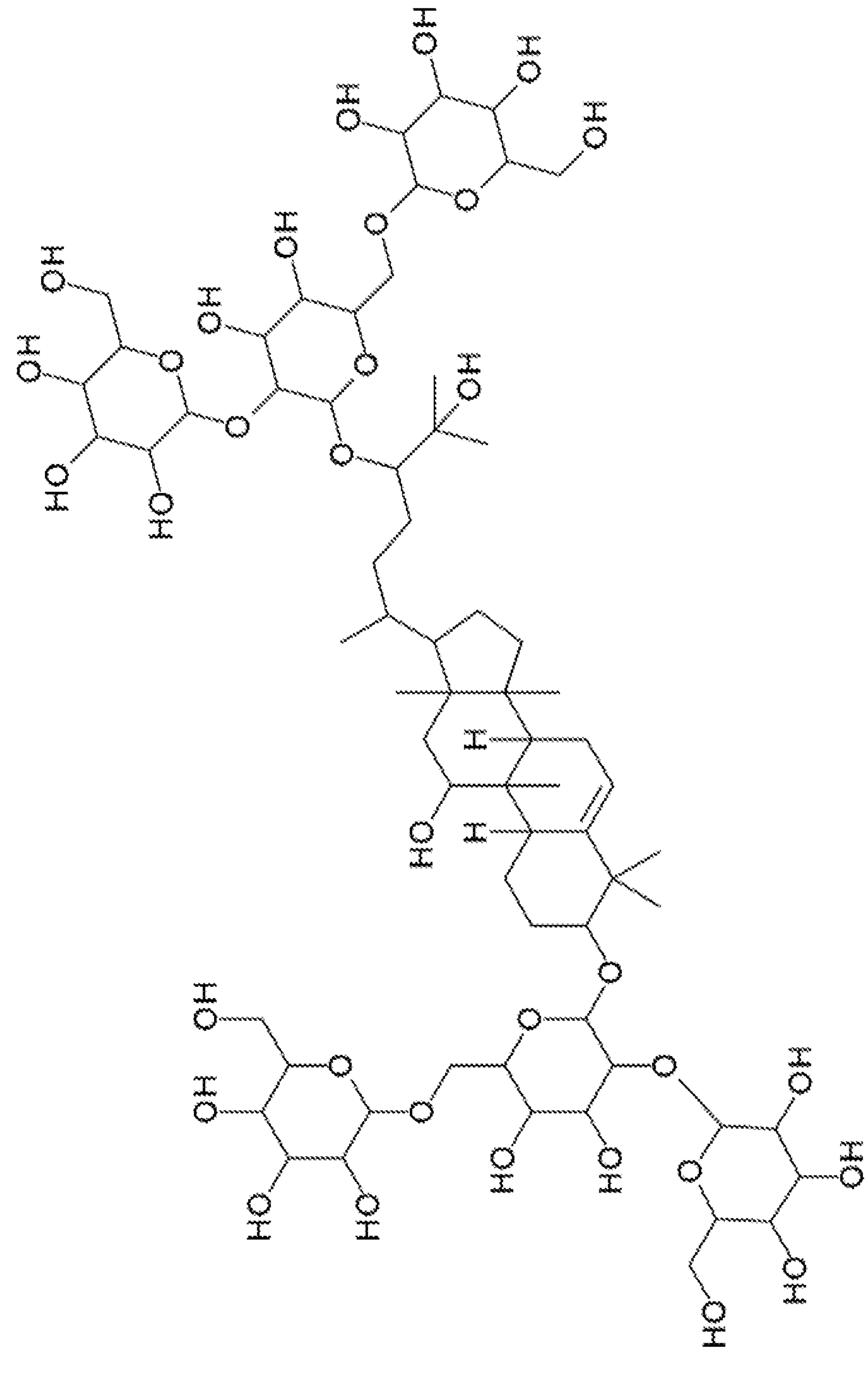
FIG. 6: Chemical structure of mogroside compound 6
Figure 7:
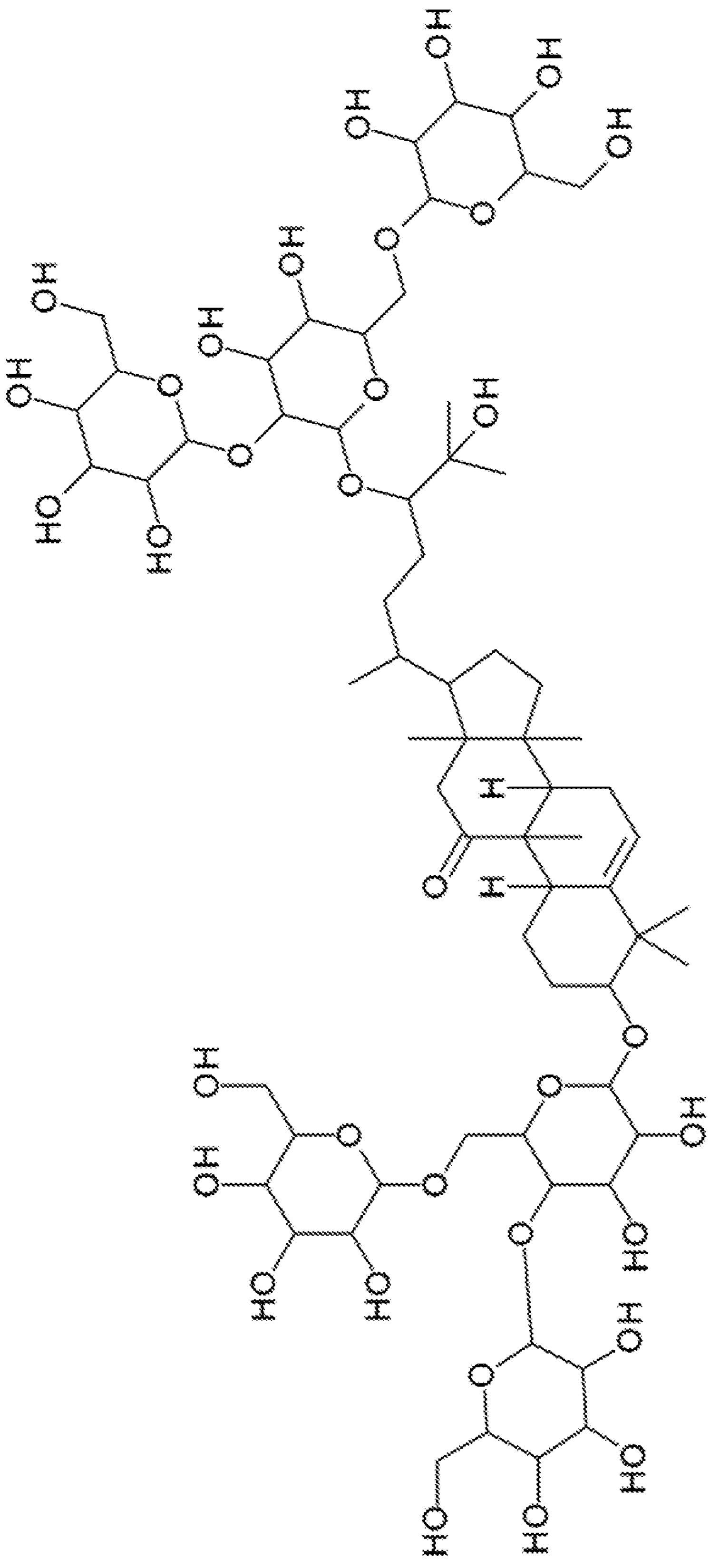
FIG. 7: Chemical structure of mogroside compound 7
Figure 8:
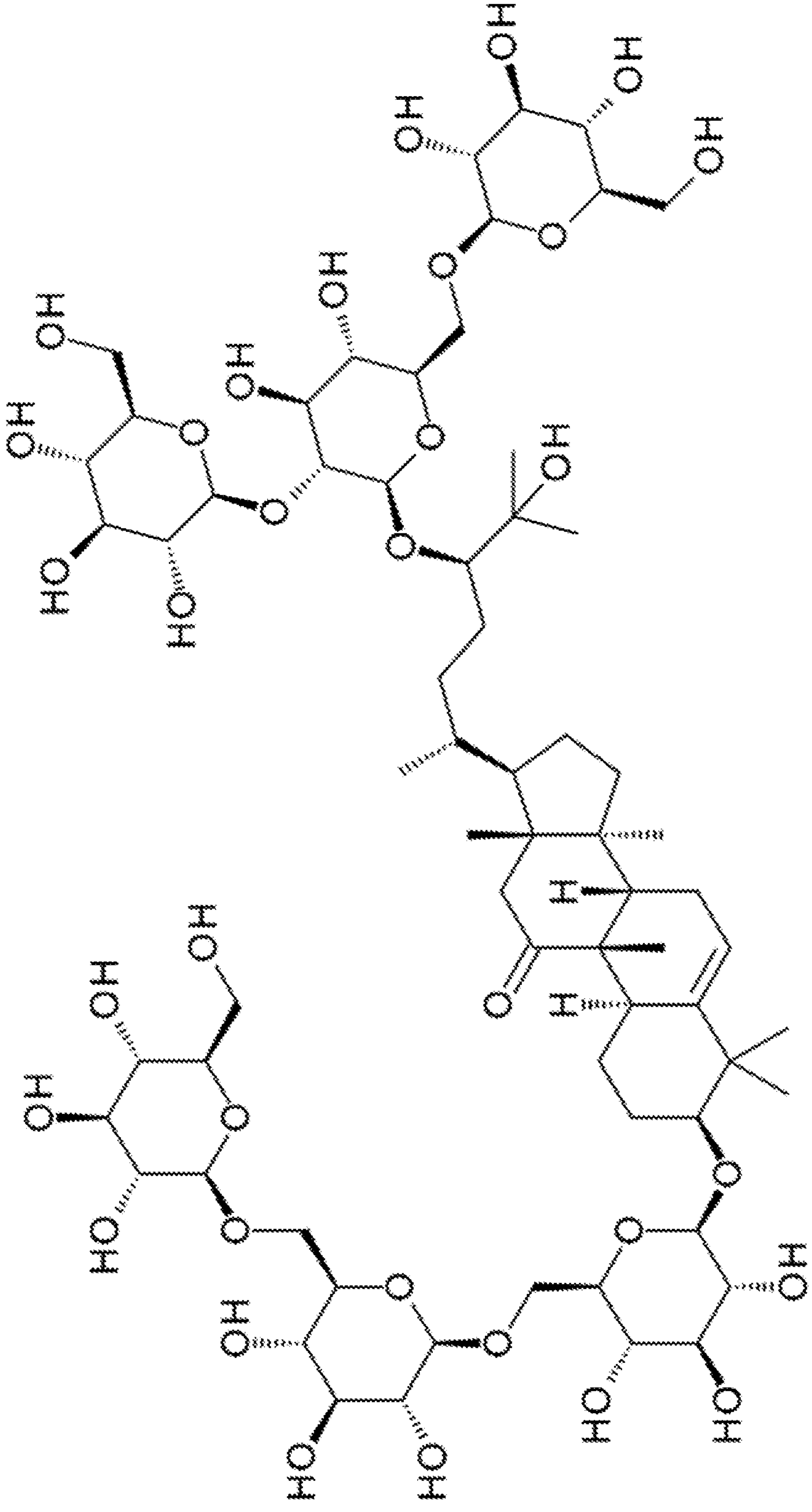
FIG. 8: Chemical structure of mogroside compound 8
Figure 9:
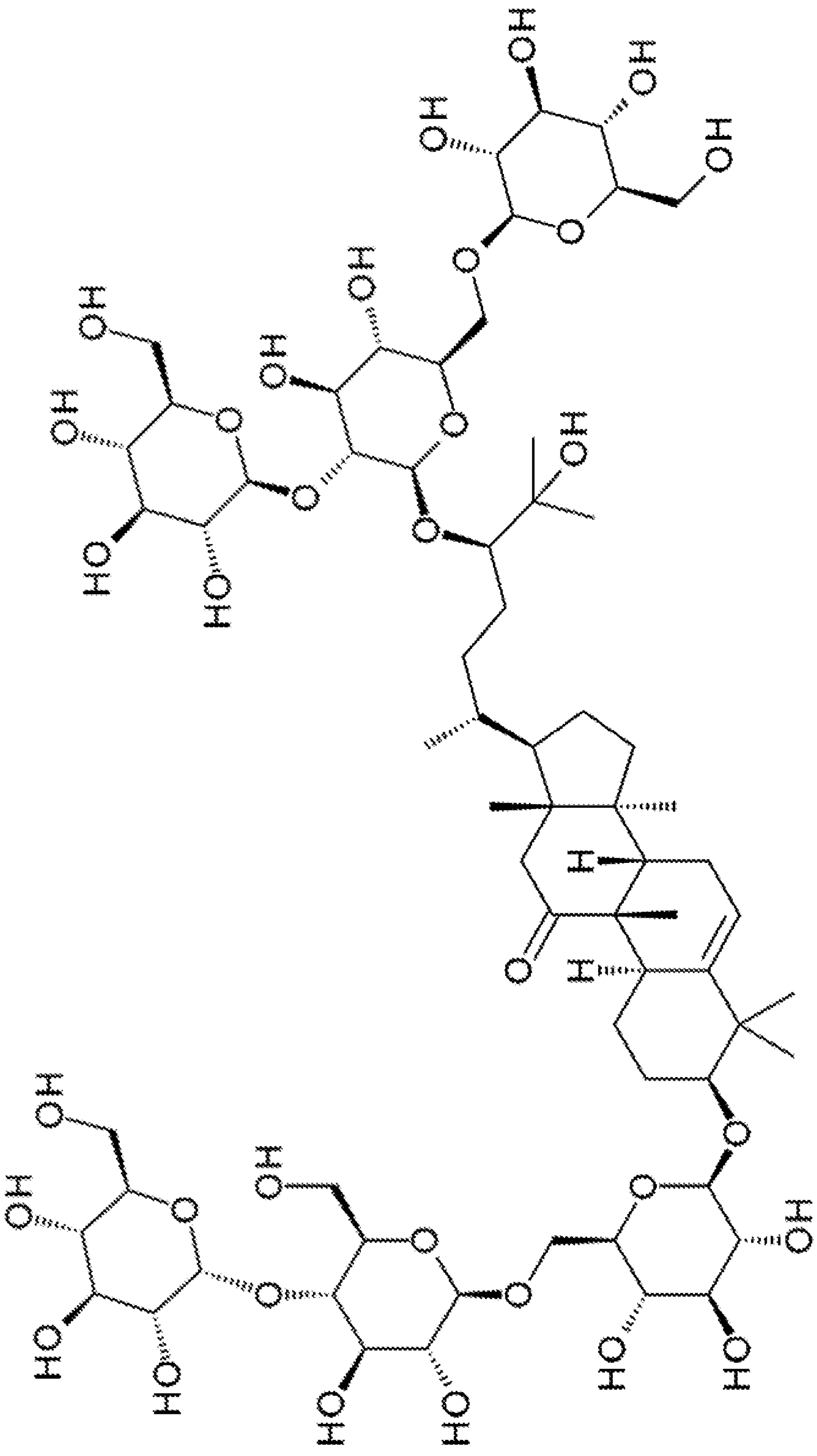
FIG. 9: Chemical structure of mogroside compound 9
Figure 10:
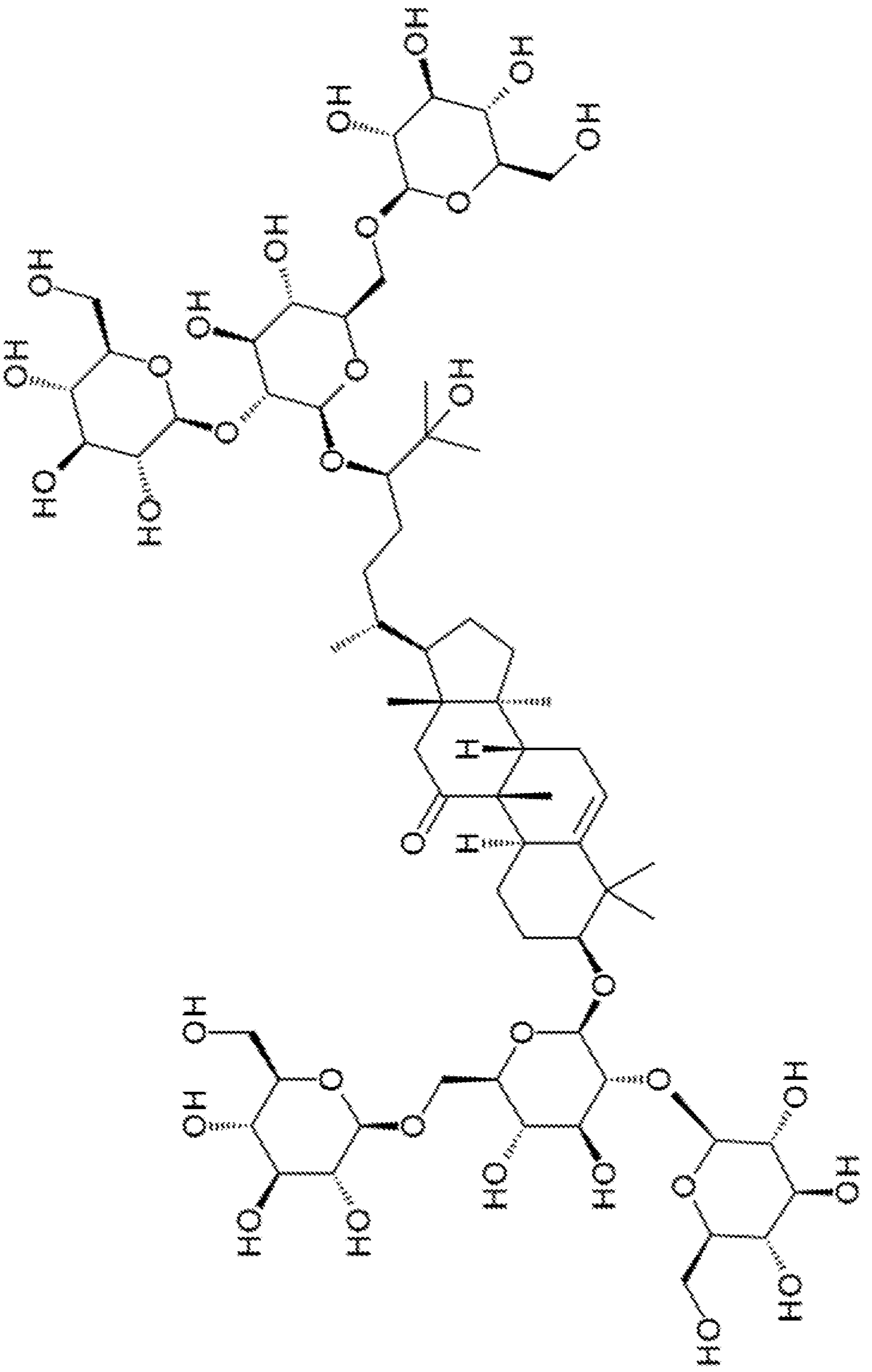
FIG. 10: Chemical structure of mogroside compound 10
Figure 11:
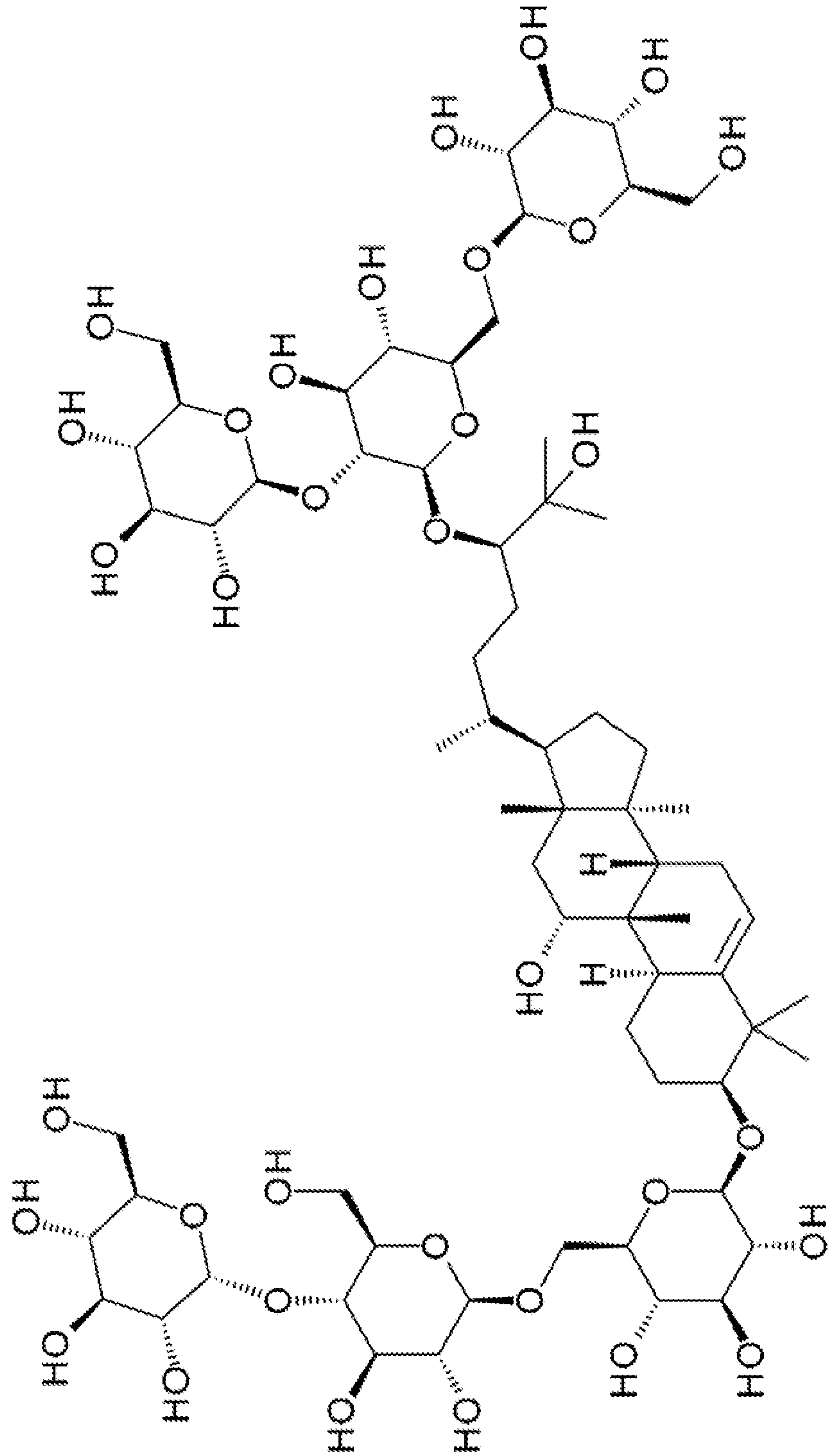
FIG. 11: Chemical structure of mogroside compound 11
Figure 12:
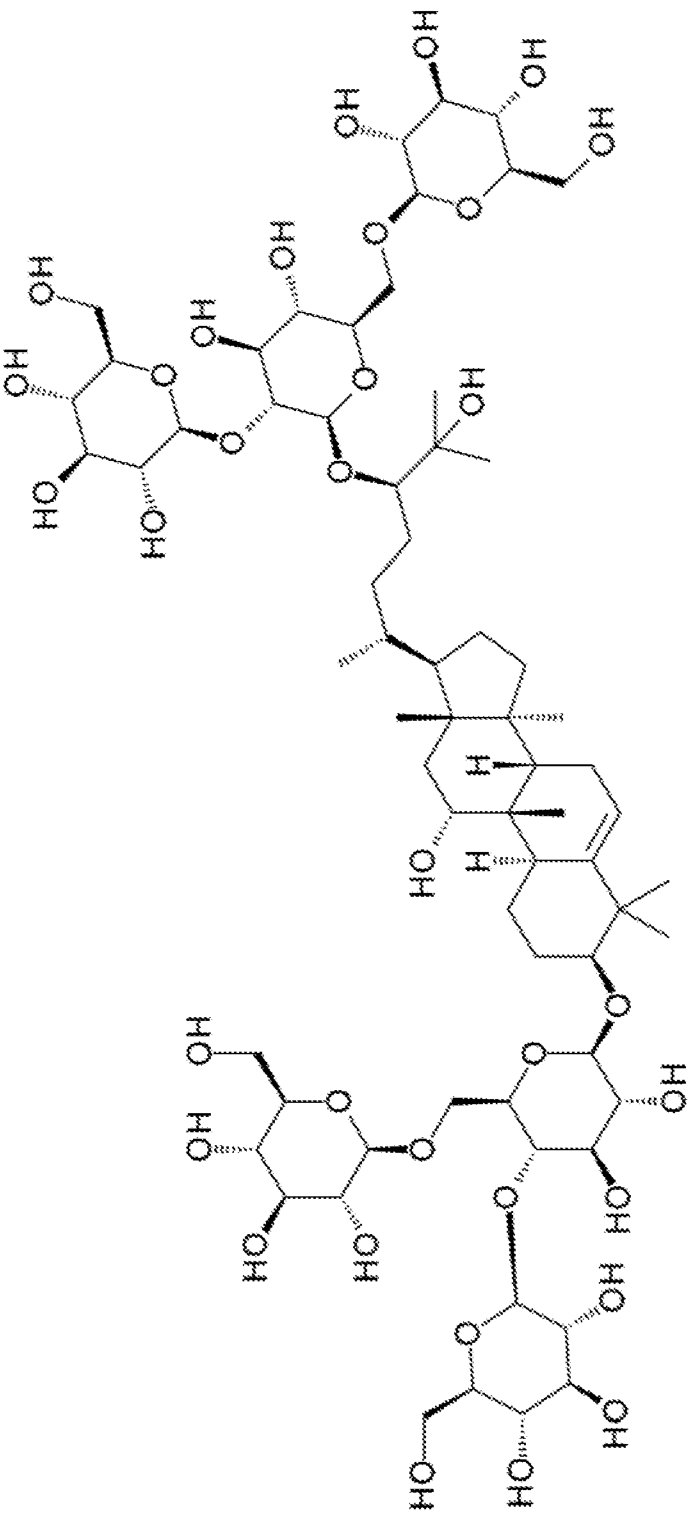
FIG. 12: Chemical structure of mogroside compound 12
Figure 13:
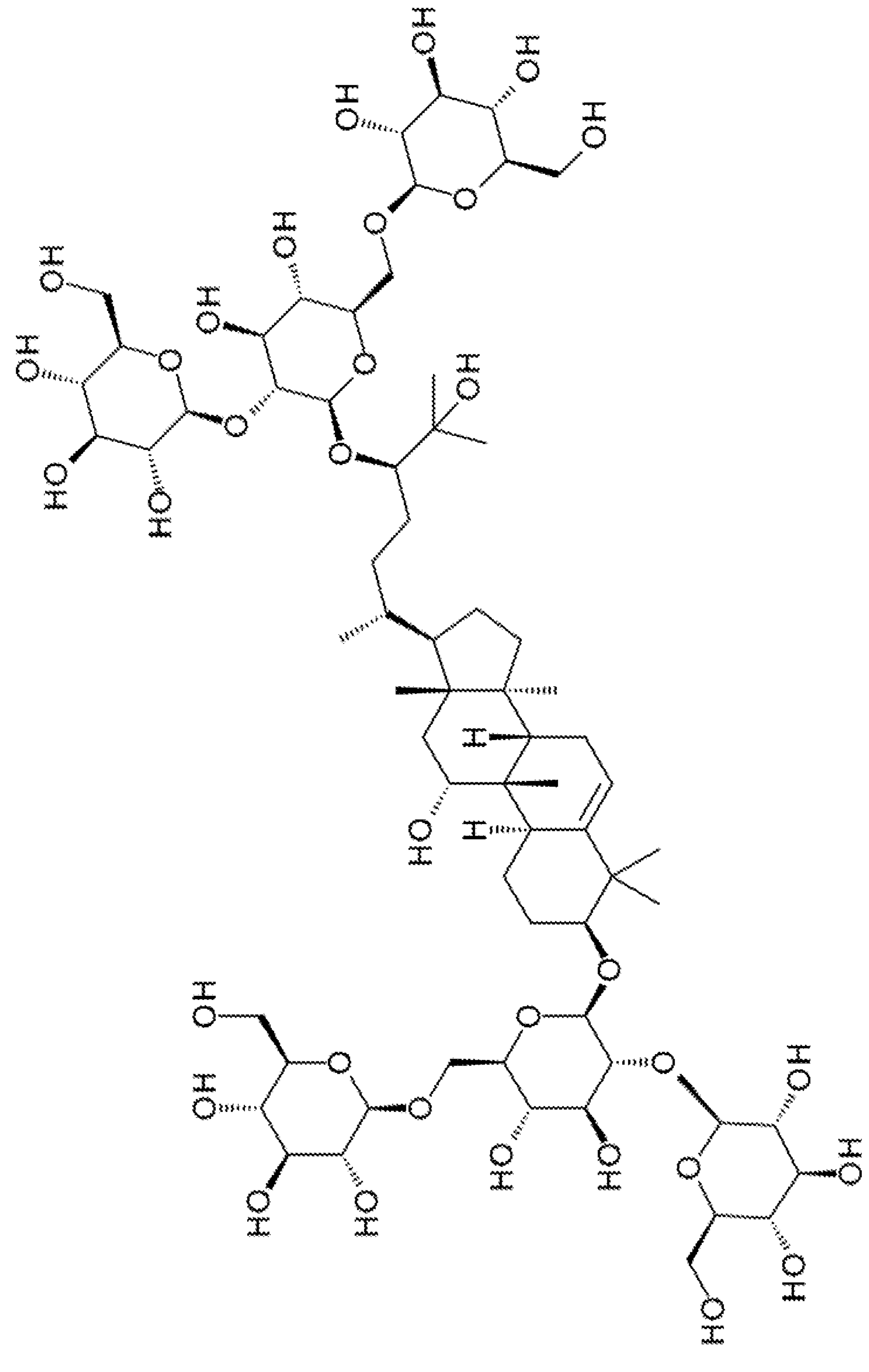
FIG. 13: Chemical structure of mogroside compound 13
Figure 14:
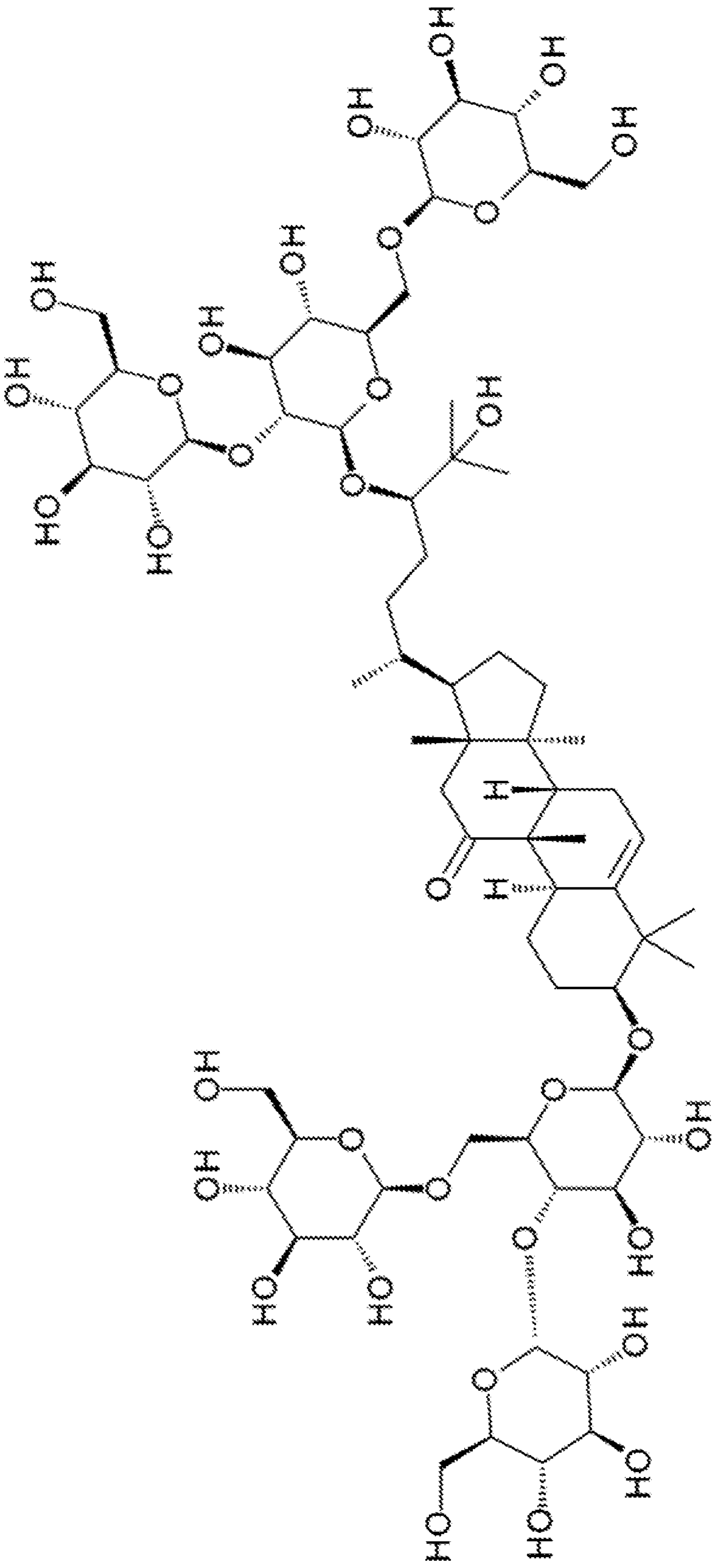
FIG. 14: Chemical structure of mogroside compound 14
Figure 15:
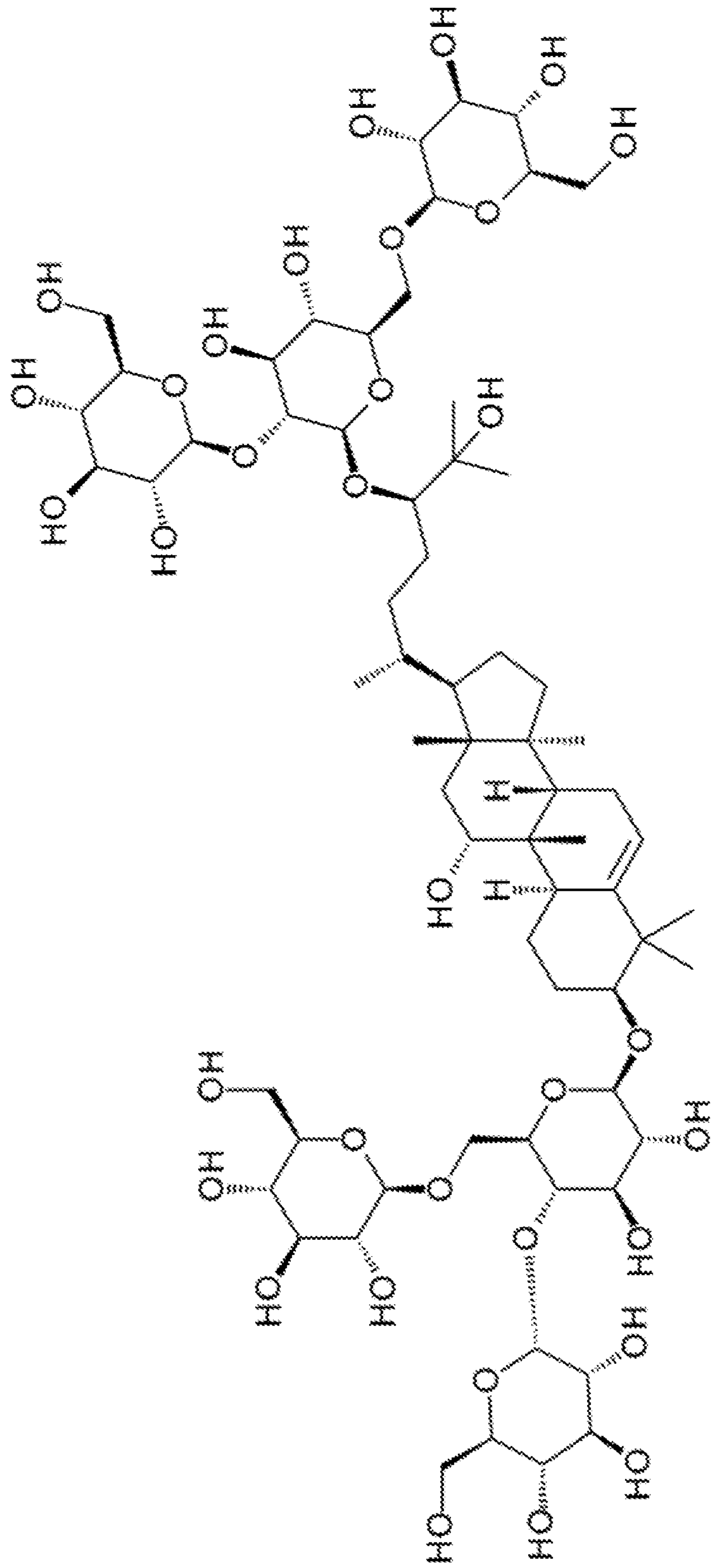
FIG. 15: Chemical structure of mogroside compound 15
Figure 16:
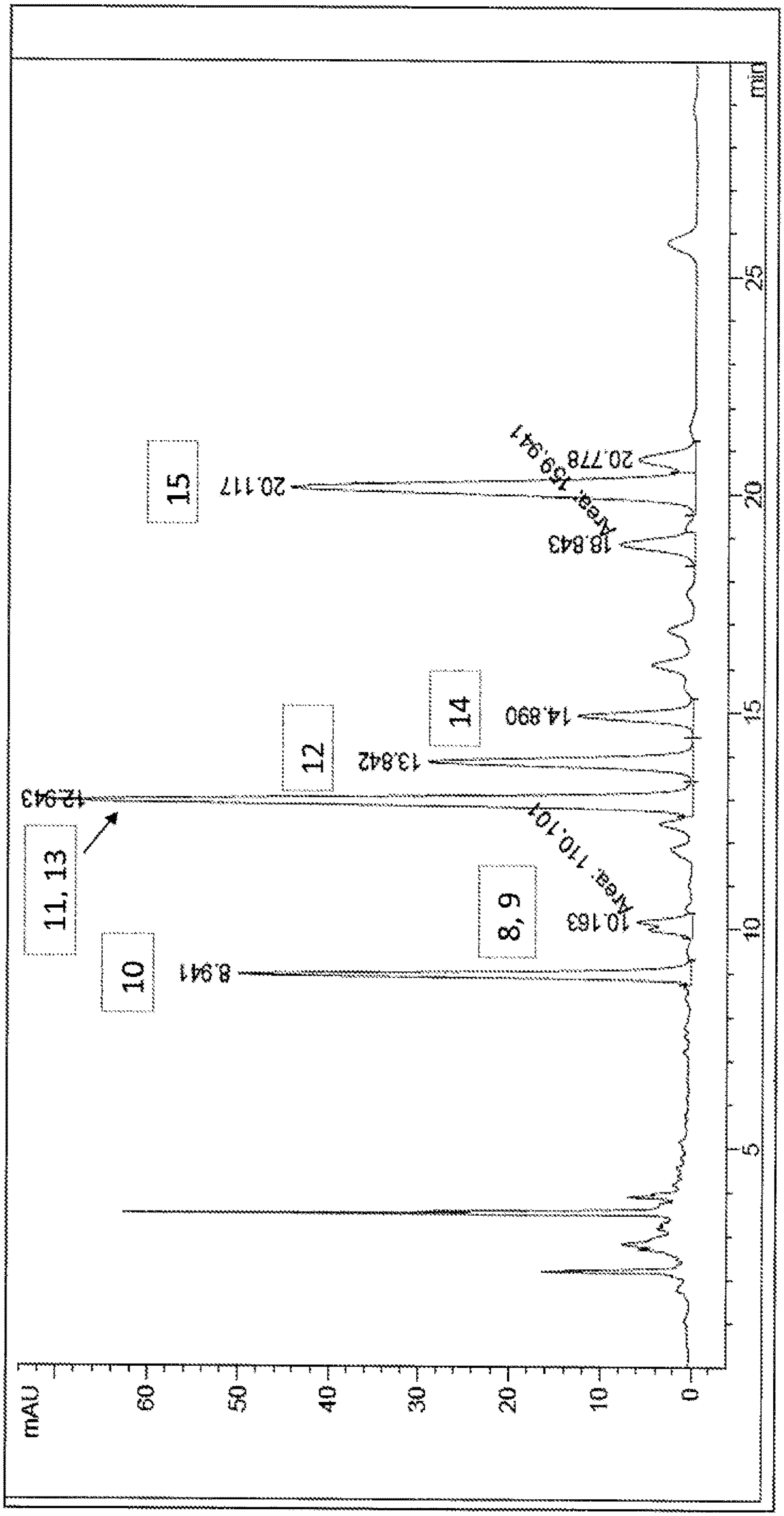
FIG. 16: Analytical-Preparative HPLC of mogroside mixtures
Figure 17:
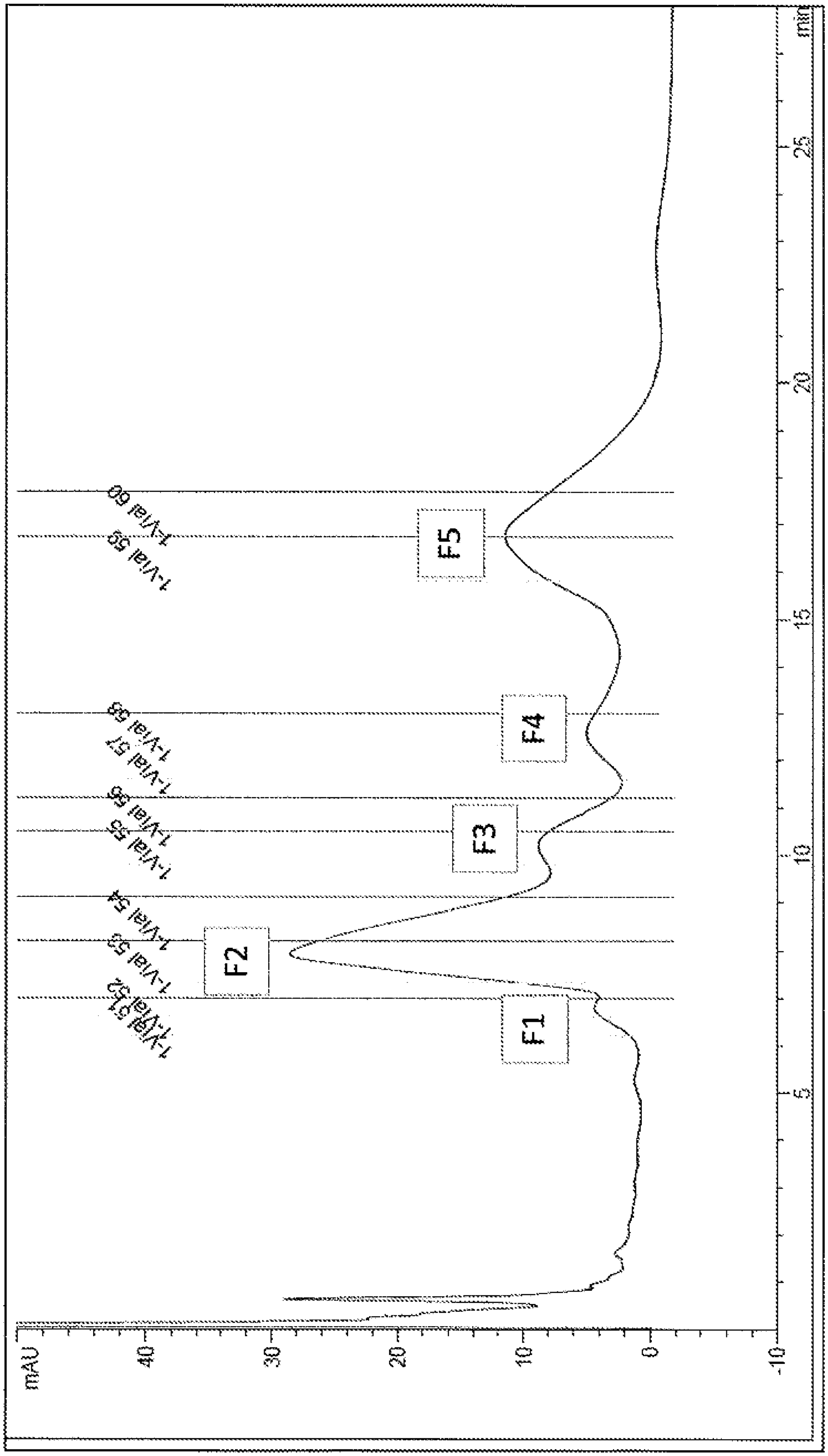
FIG. 17: Preparative HPLC of mogroside mixtures
Figure 18:
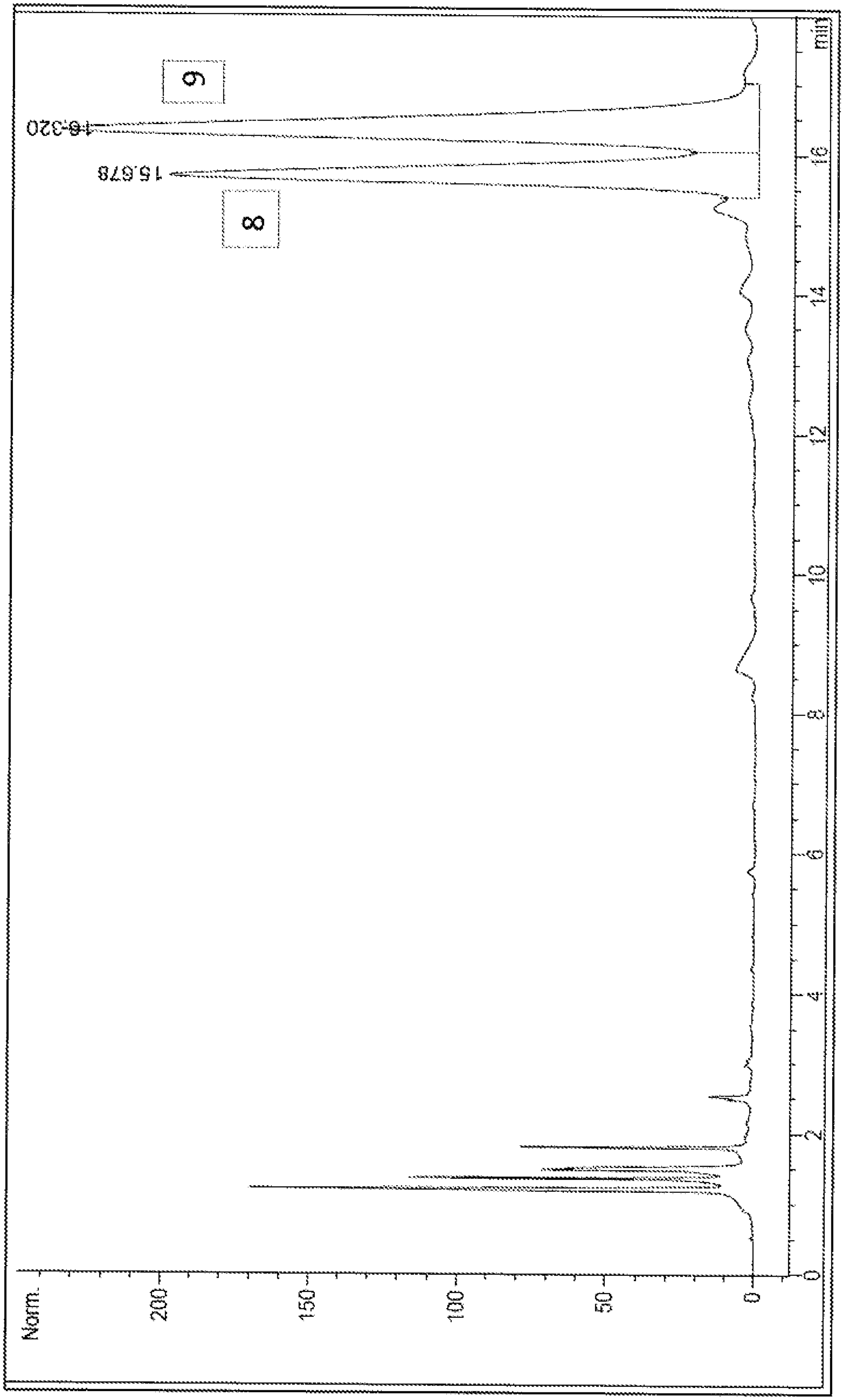
FIG. 18: Analytical-Preparative HPLC of Fraction 1 containing compounds 8 and 9
Figure 19:
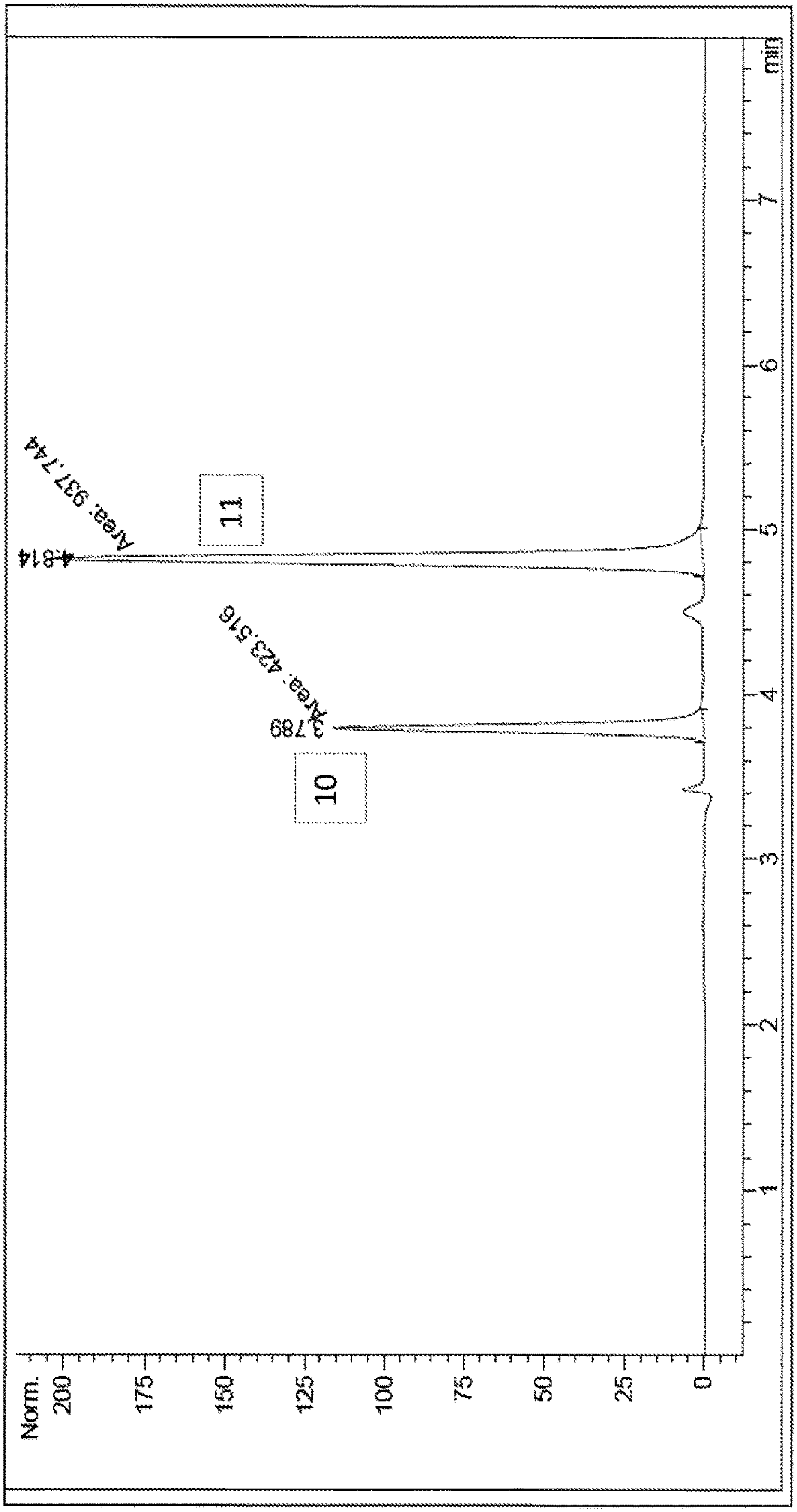
FIG. 19: Analytical-Preparative HPLC of Fraction 2 containing compounds 10 and 11
Figure 20:
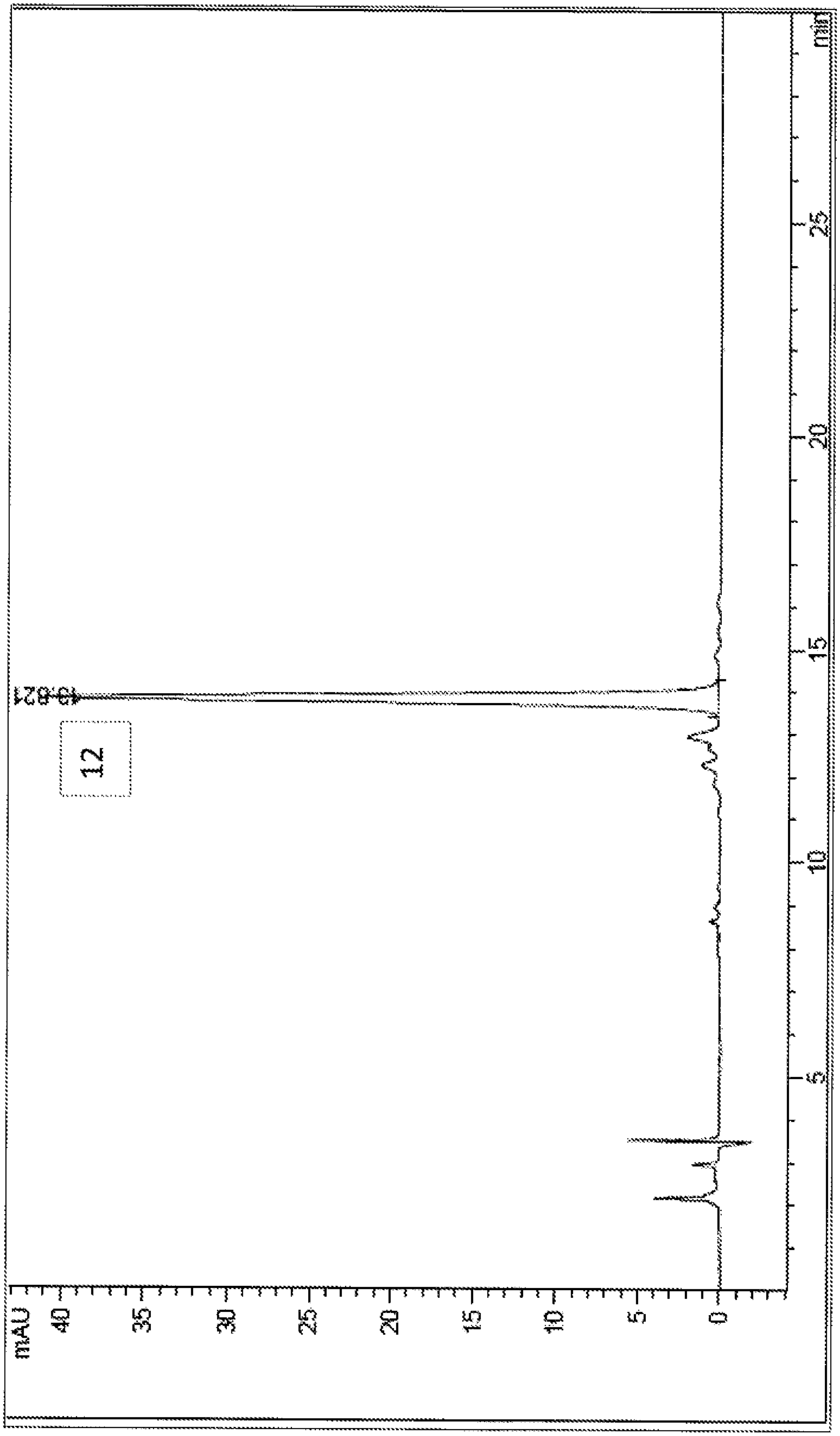
FIG. 20: Analytical-Preparative HPLC of Fraction 3 containing compound 12
Figure 21:
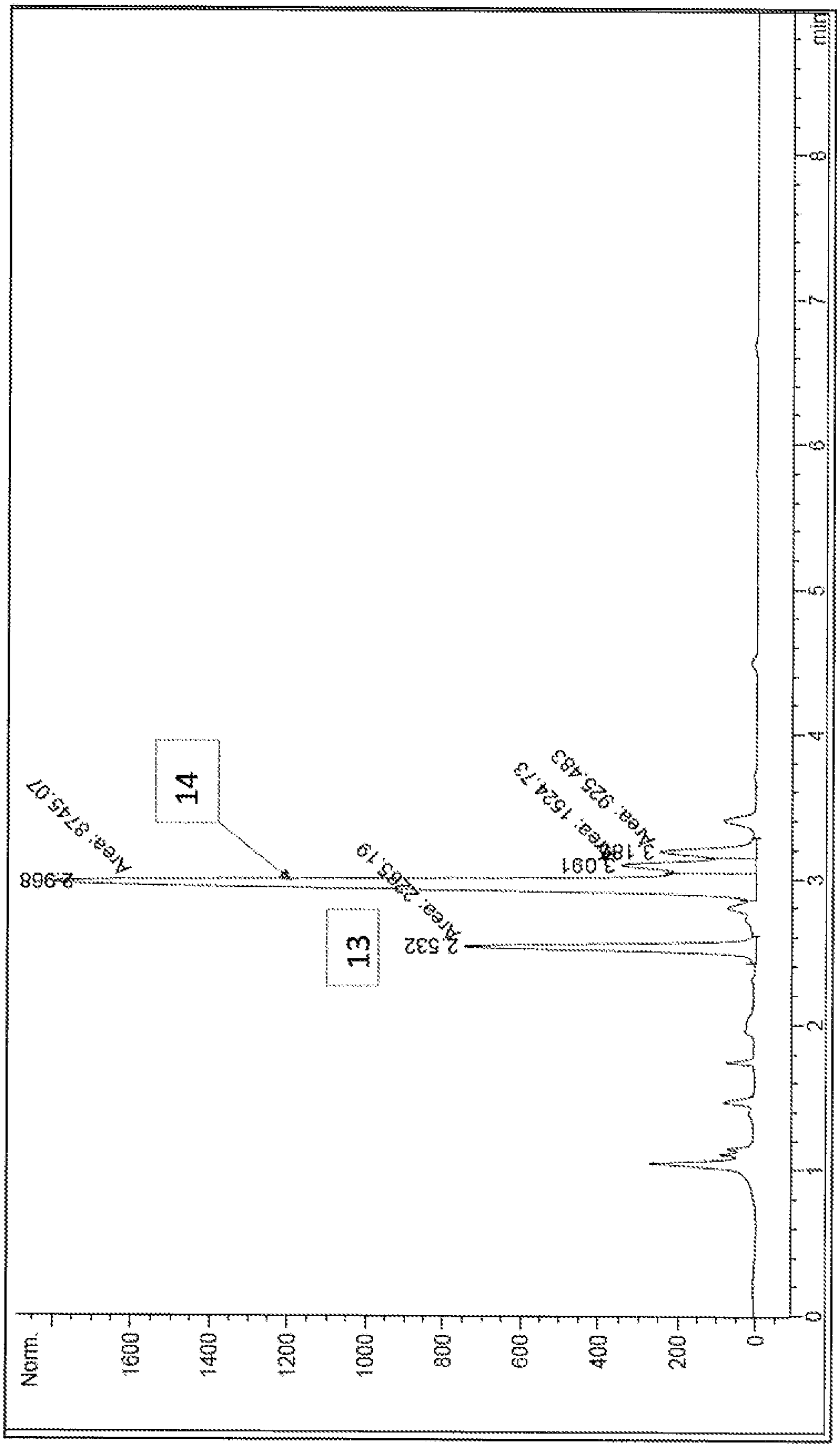
FIG. 21: Analytical-Preparative HPLC of Fraction 4 containing compounds 13, 14
Figure 22:
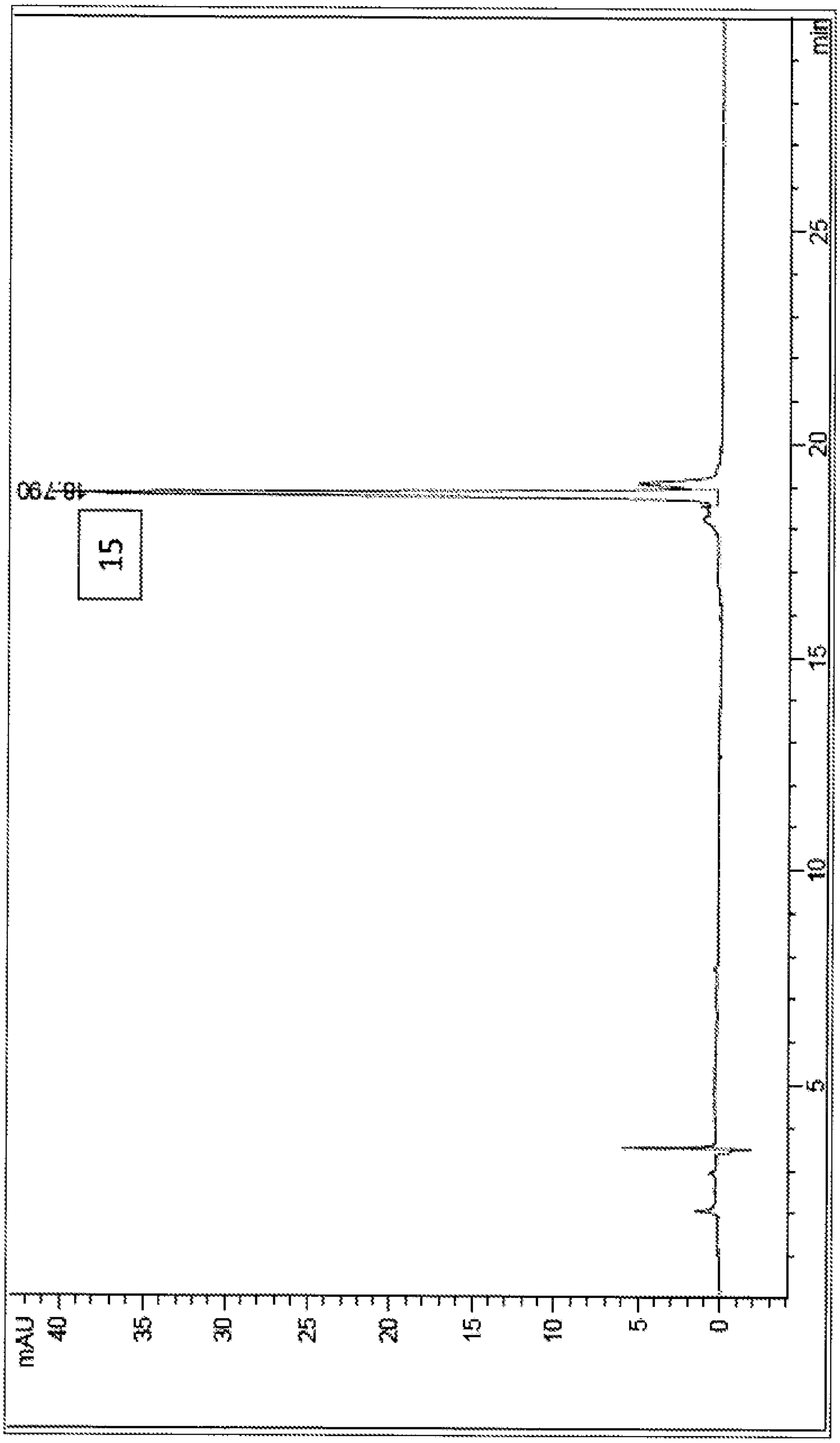
FIG. 22: Analytical-Preparative HPLC of Fraction 5 containing compound 15.
Figure 23:
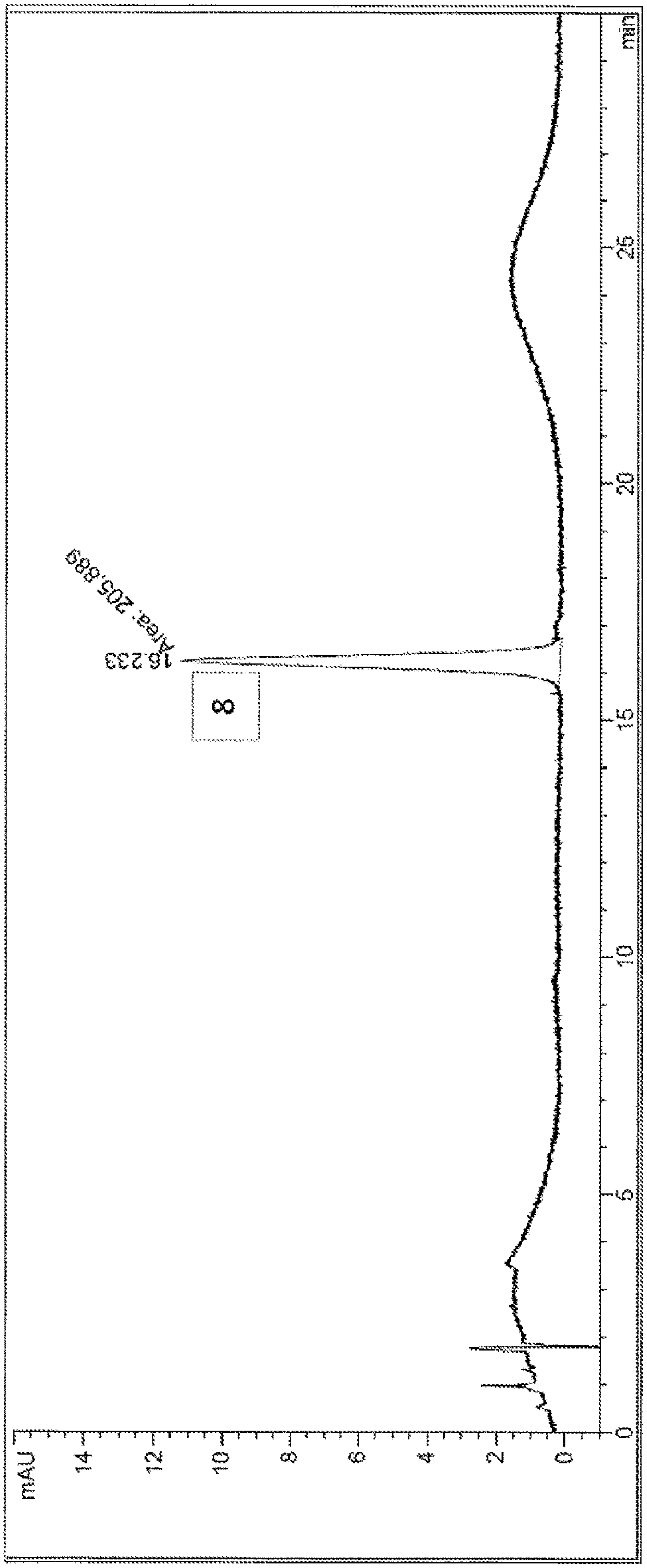
FIG. 23: Analytical-Preparative HPLC of compound 8
Figure 24:
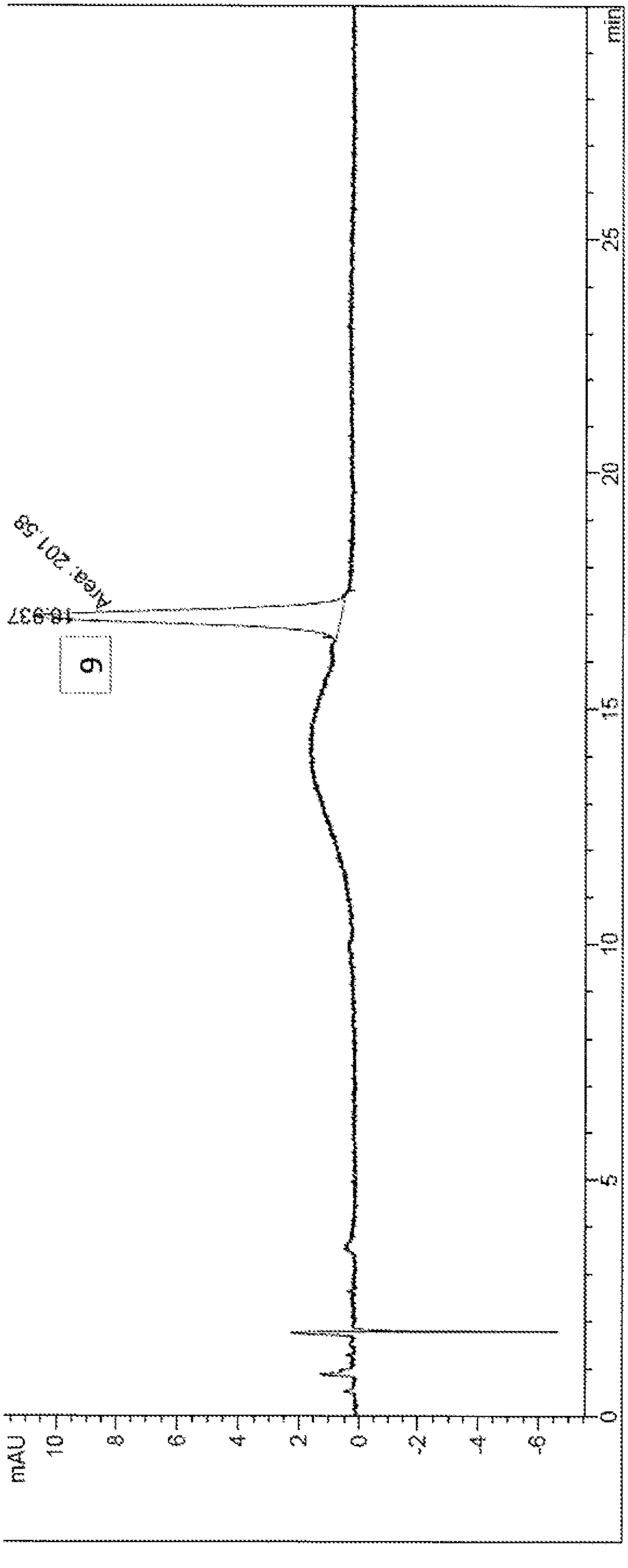
FIG. 24: Analytical-Preparative HPLC of compound 9
Figure 25:
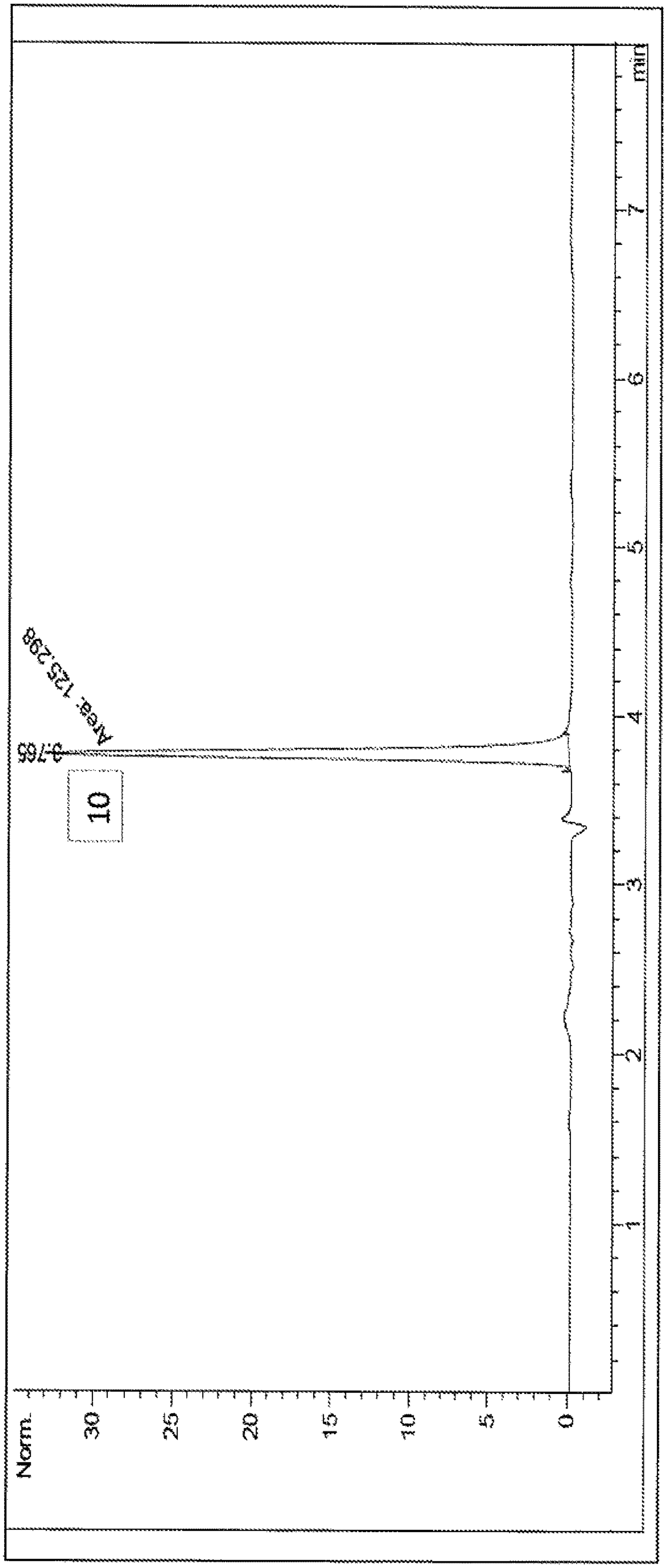
FIG. 25: Analytical-Preparative HPLC of compound 10
Figure 26:
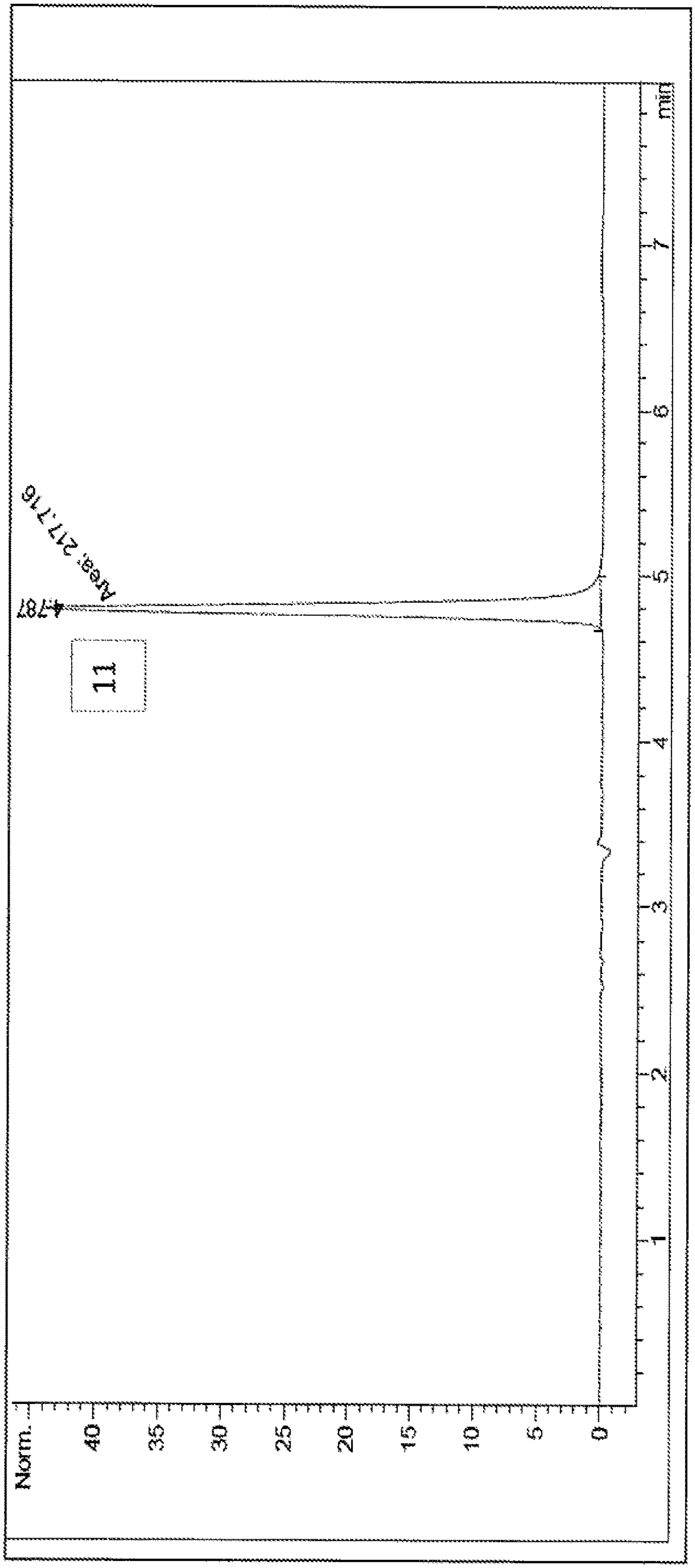
FIG. 26: Analytical-Preparative HPLC of compound 11
Figure 27:
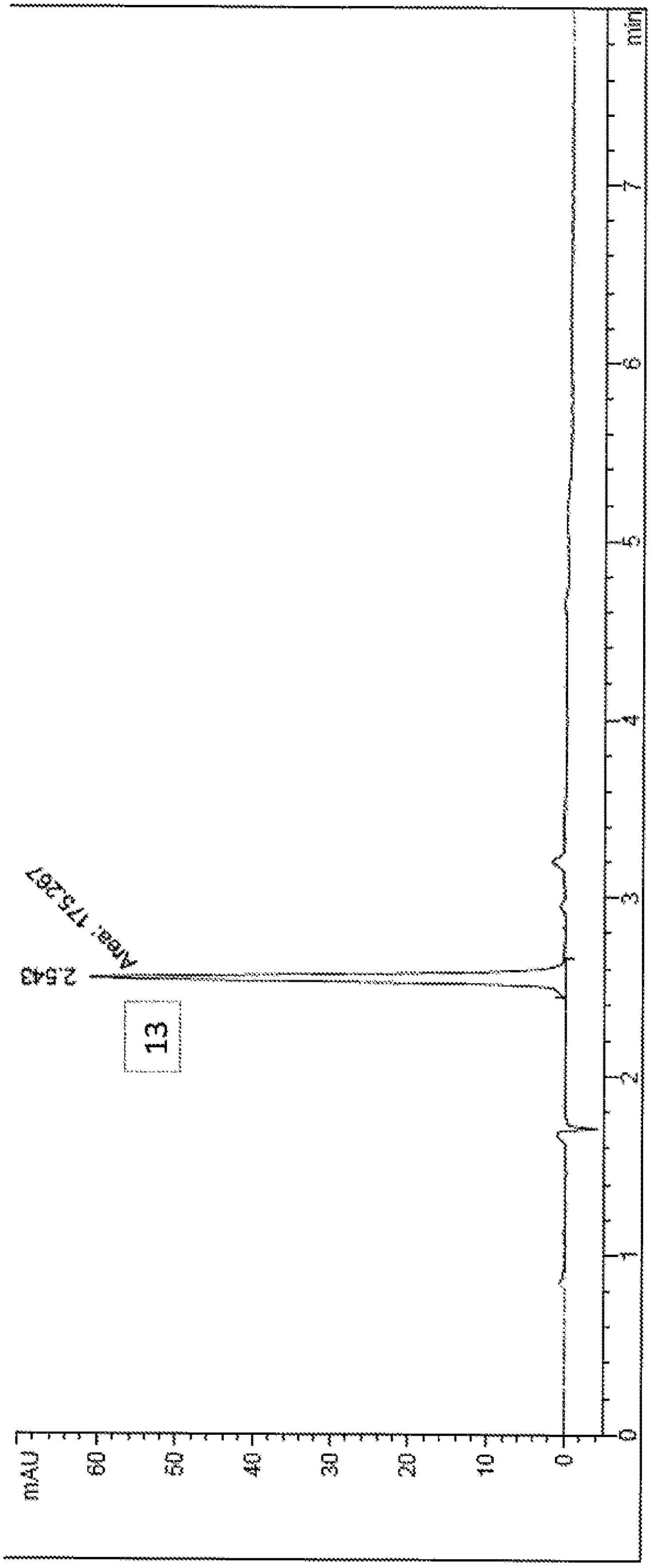
FIG. 27: Analytical-Preparative HPLC of compound 13
Figure 28:
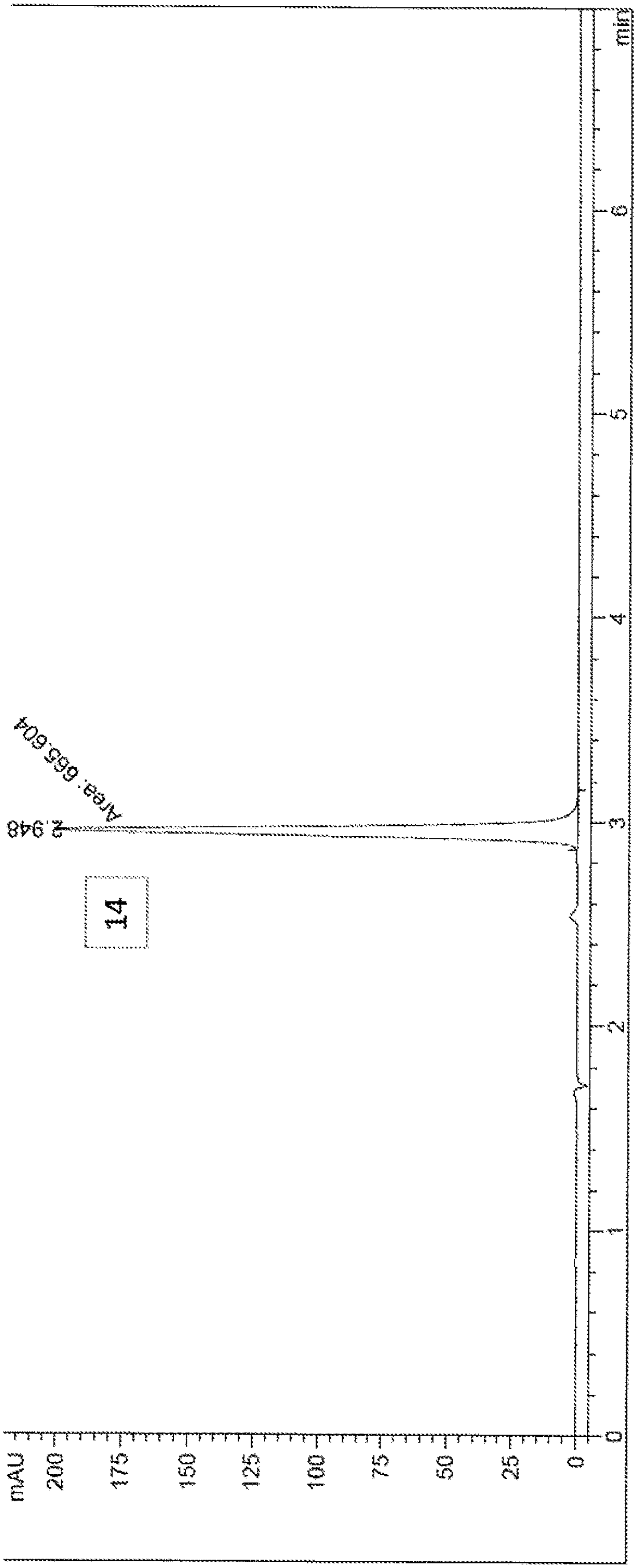
FIG. 28: Analytical-Preparative HPLC of compound 14
Figure 29A:
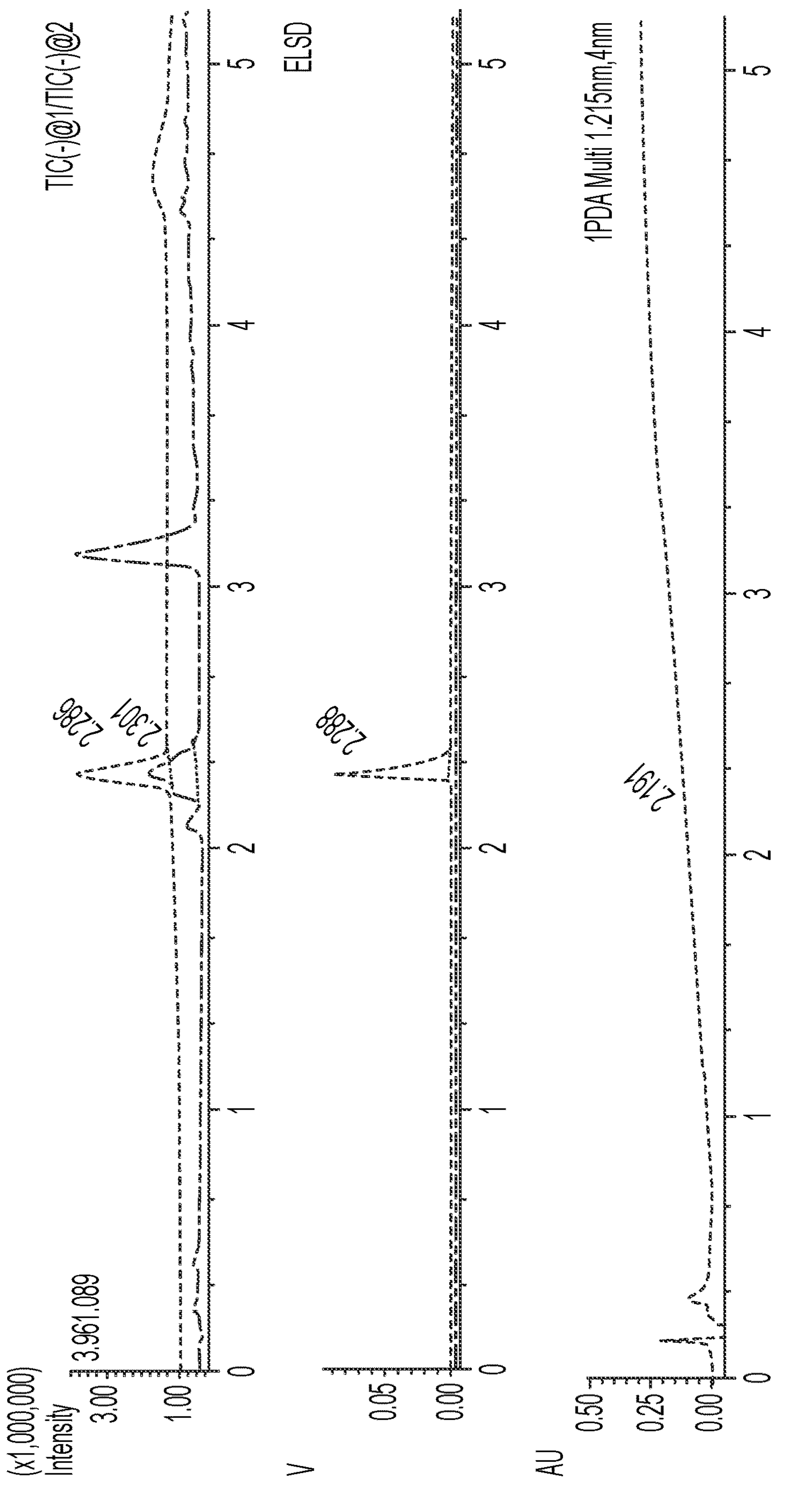
FIGS. 29A-29B: LCMS of compound 8
Figure 29B:
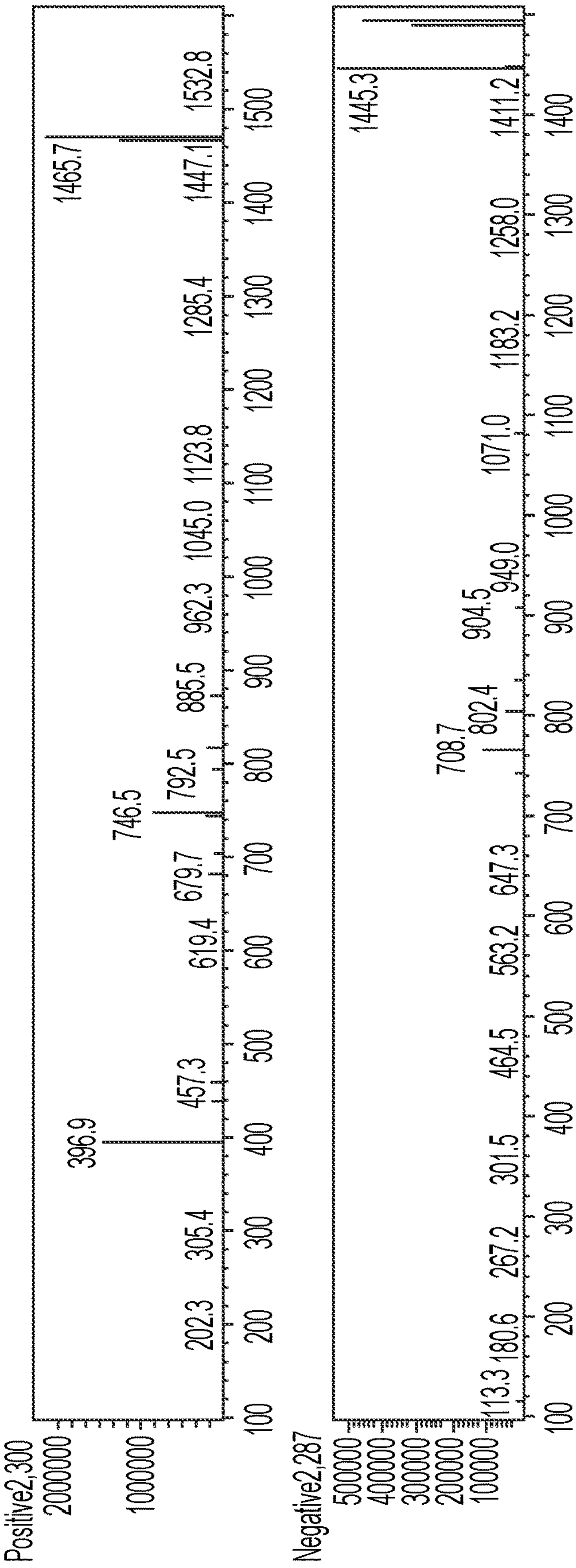
Figure 32:
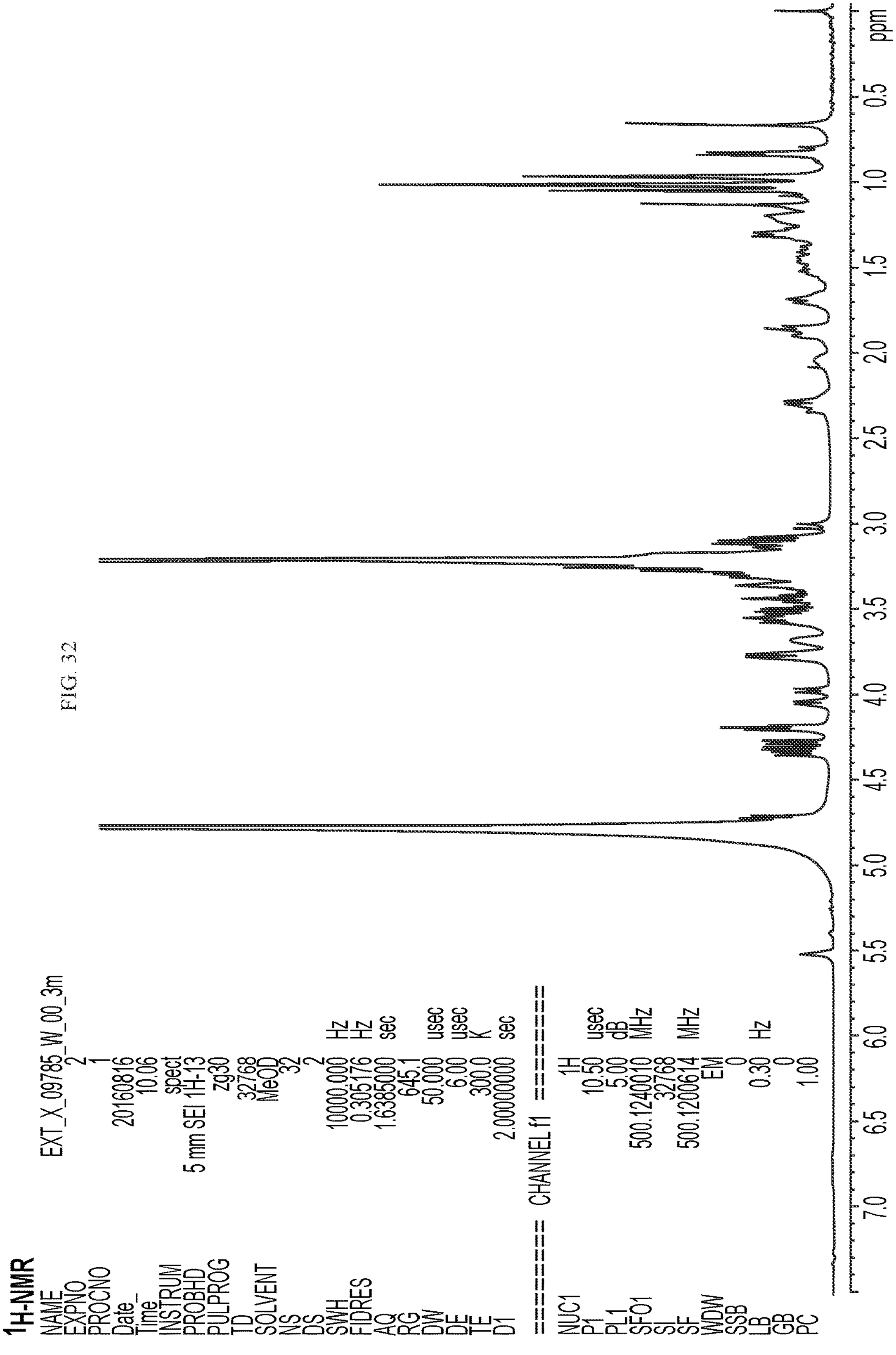
FIG. 32: 1H NMR spectrum of compound 8
Figure 33A:
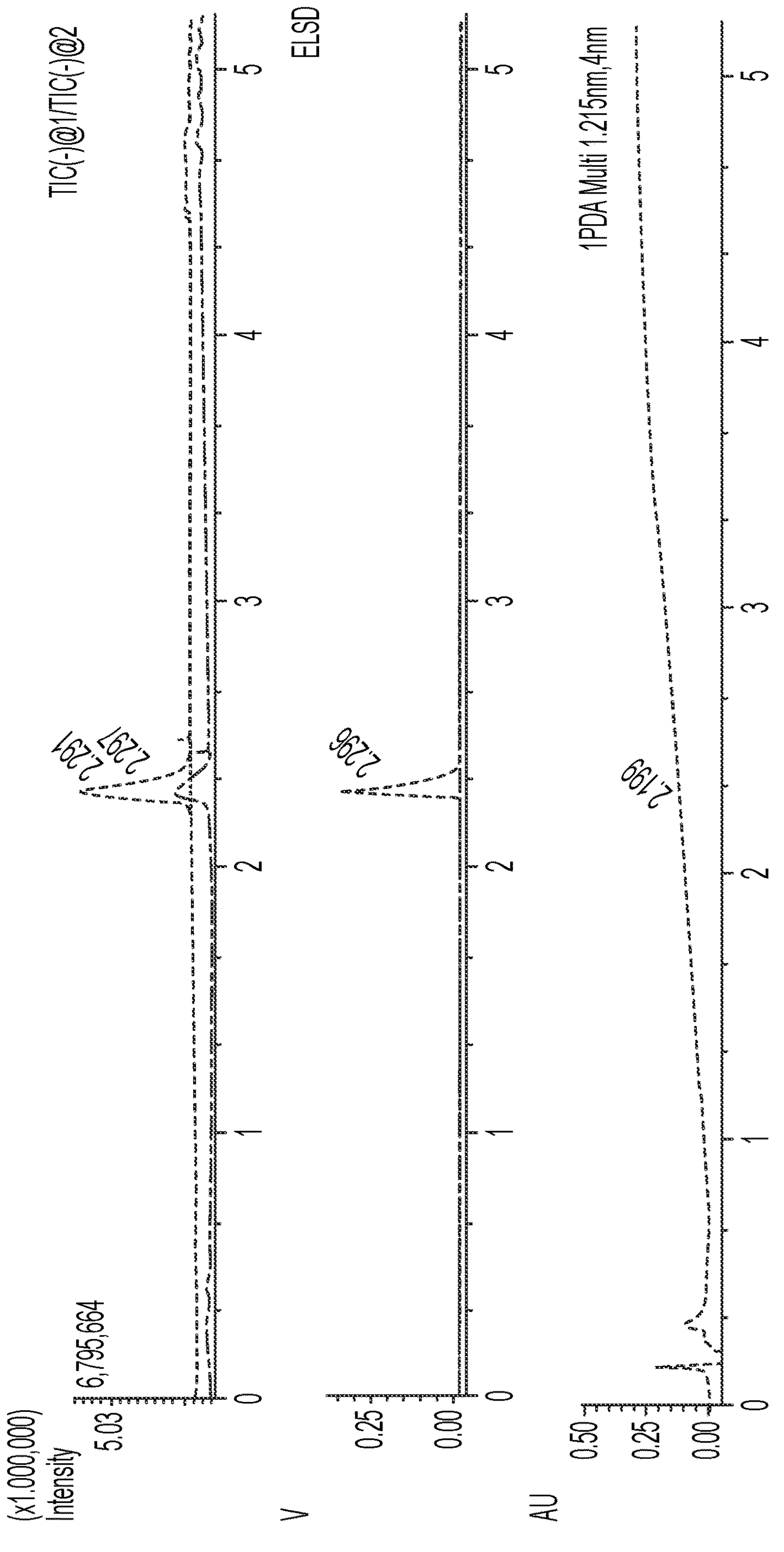
FIGS. 33A-33B: LCMS of compound 9
Figure 33B:
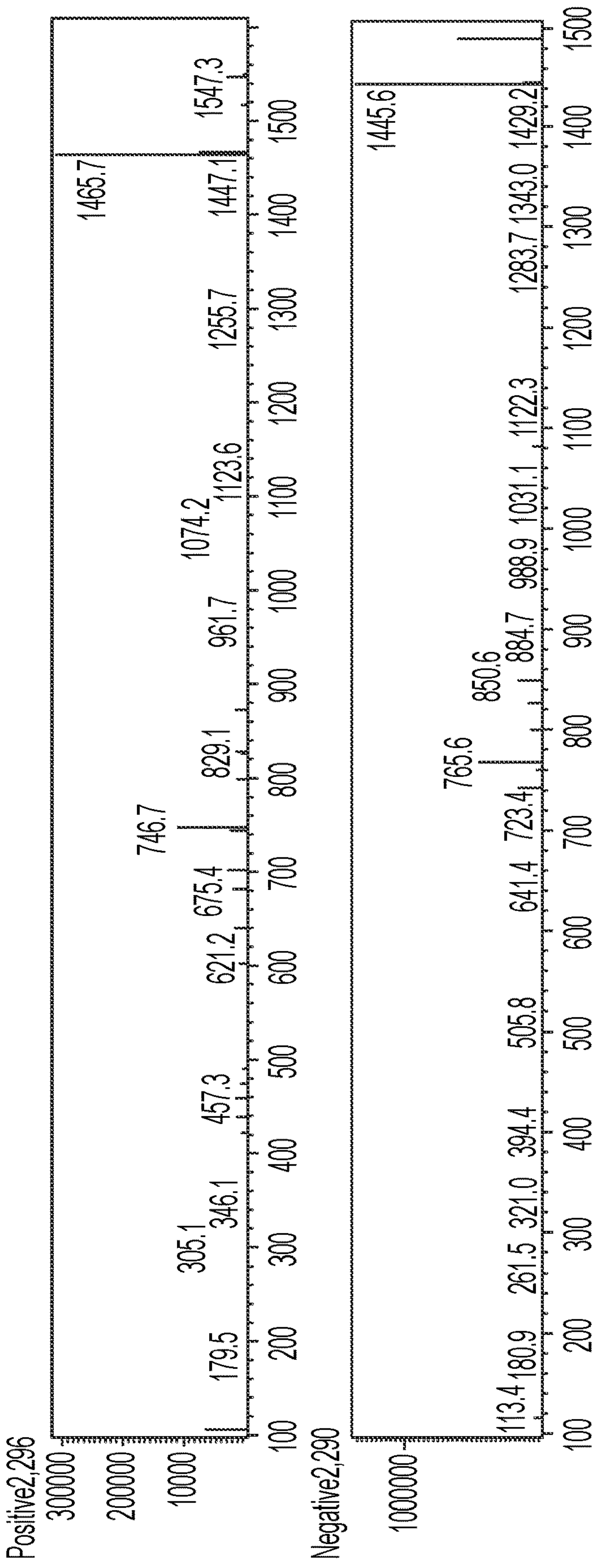
Figure 36:
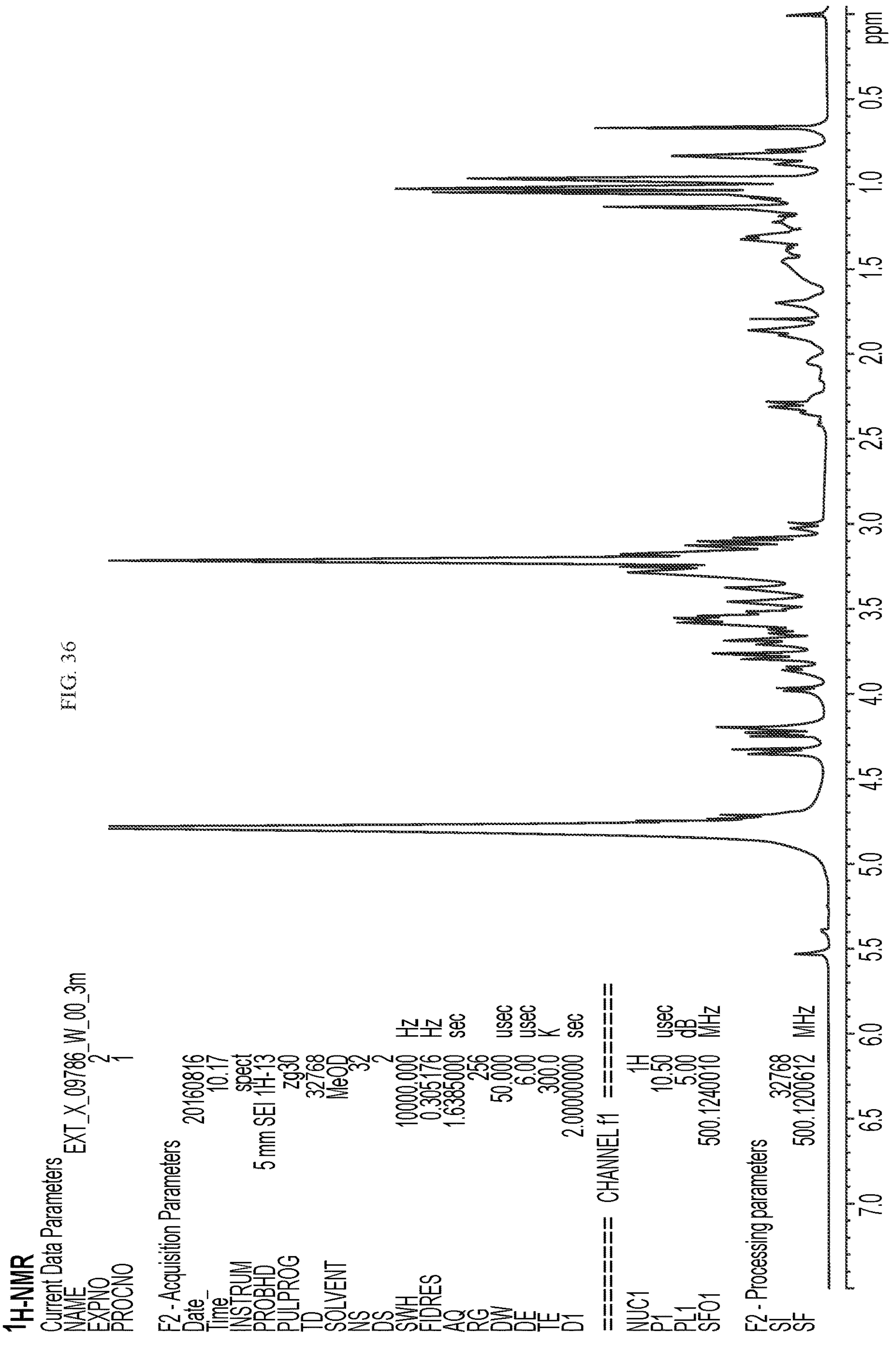
FIG. 36: 1H NMR spectrum of compound 9
Figure 37A:
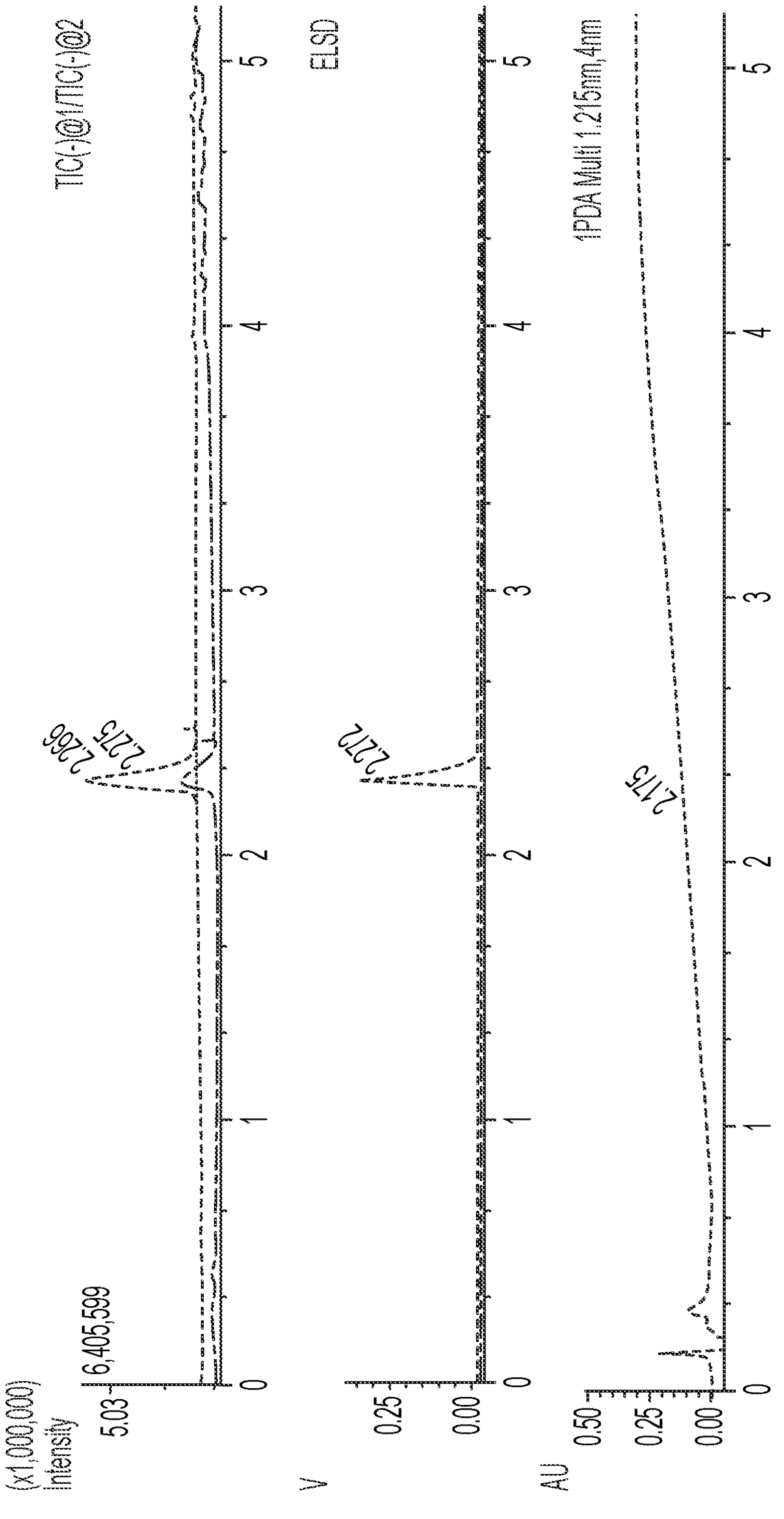
FIGS. 37A-37B: LCMS of compound 10
Figure 37B:
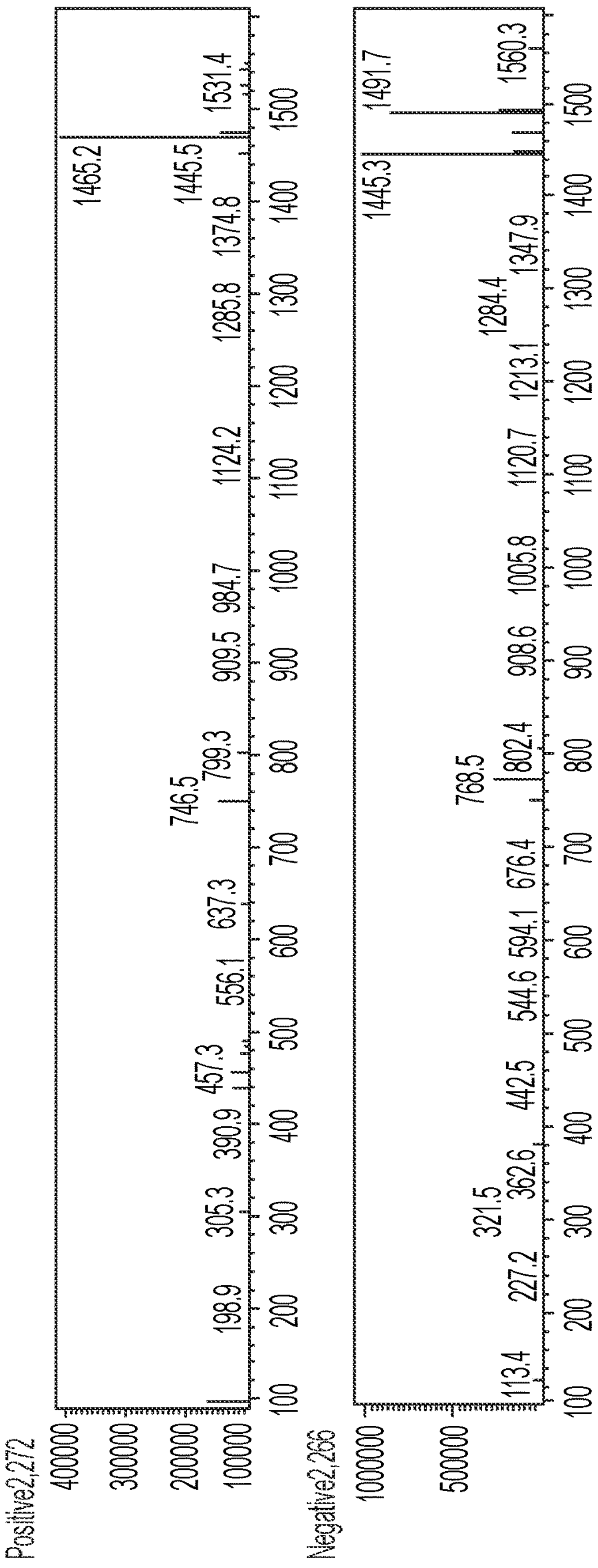
Figure 40:
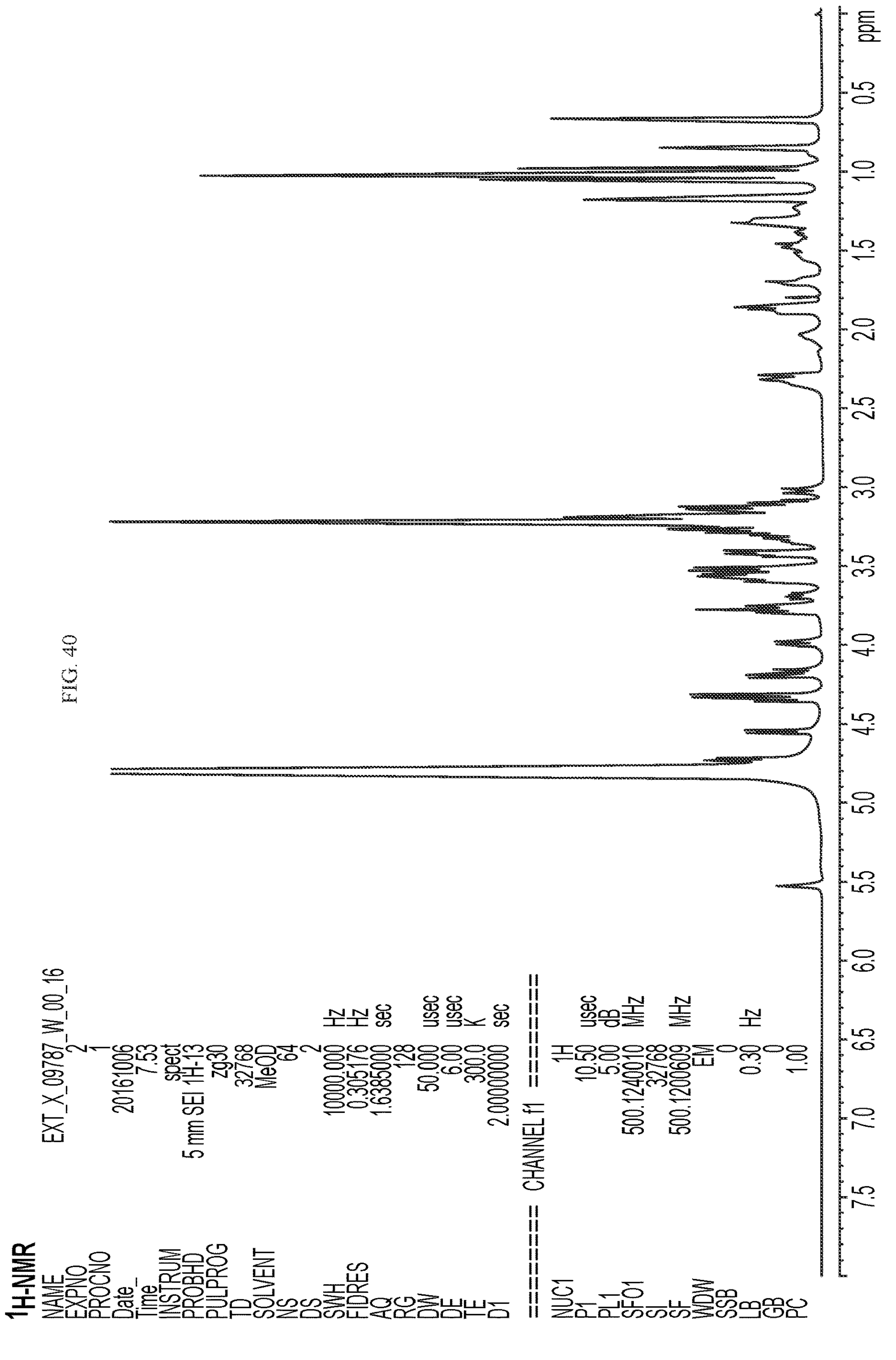
FIG. 40: 1H NMR spectrum of compound 10
Figure 41A:
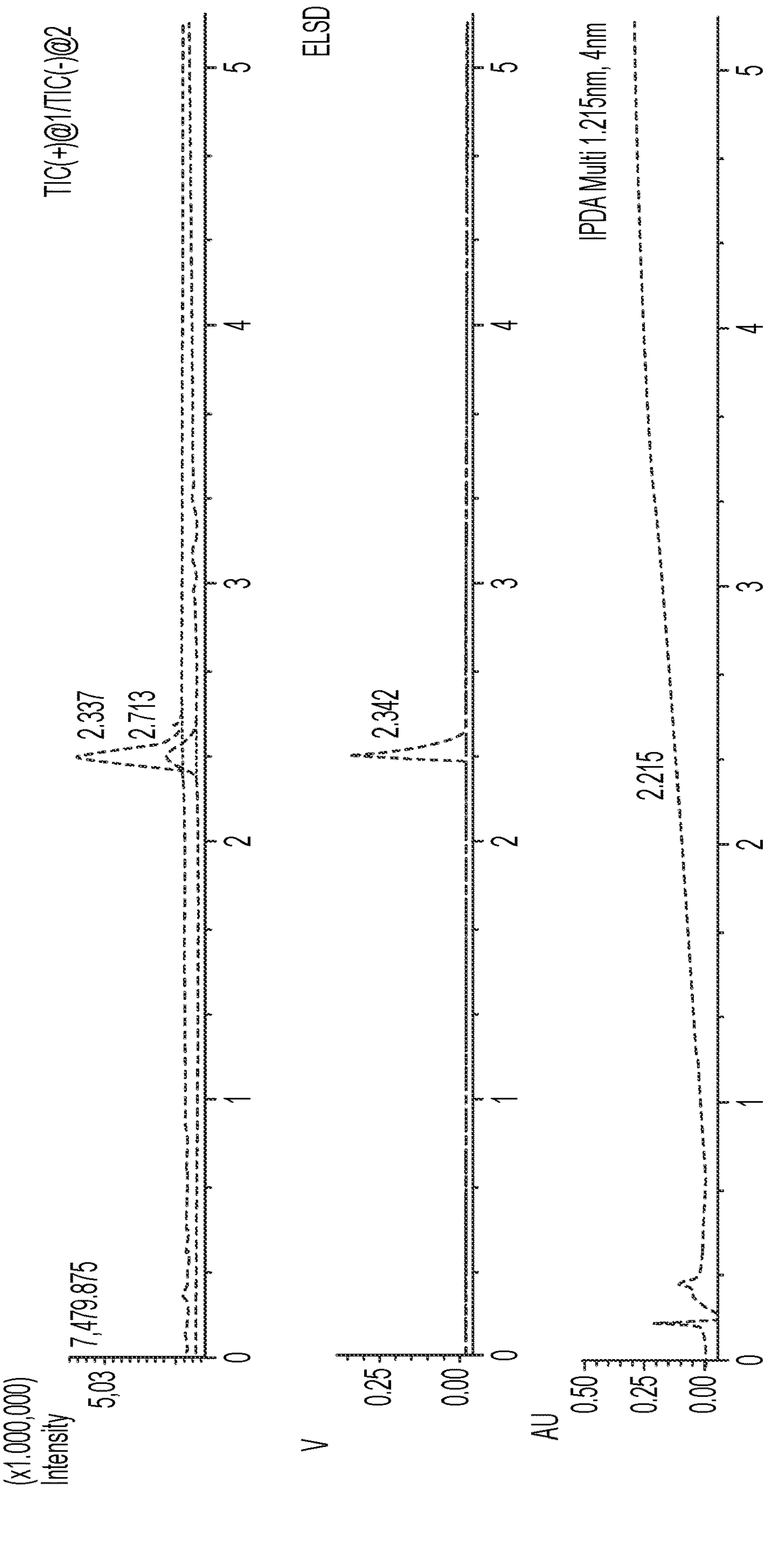
FIGS. 41A-41B: LCMS of compound 11
Figure 41B:
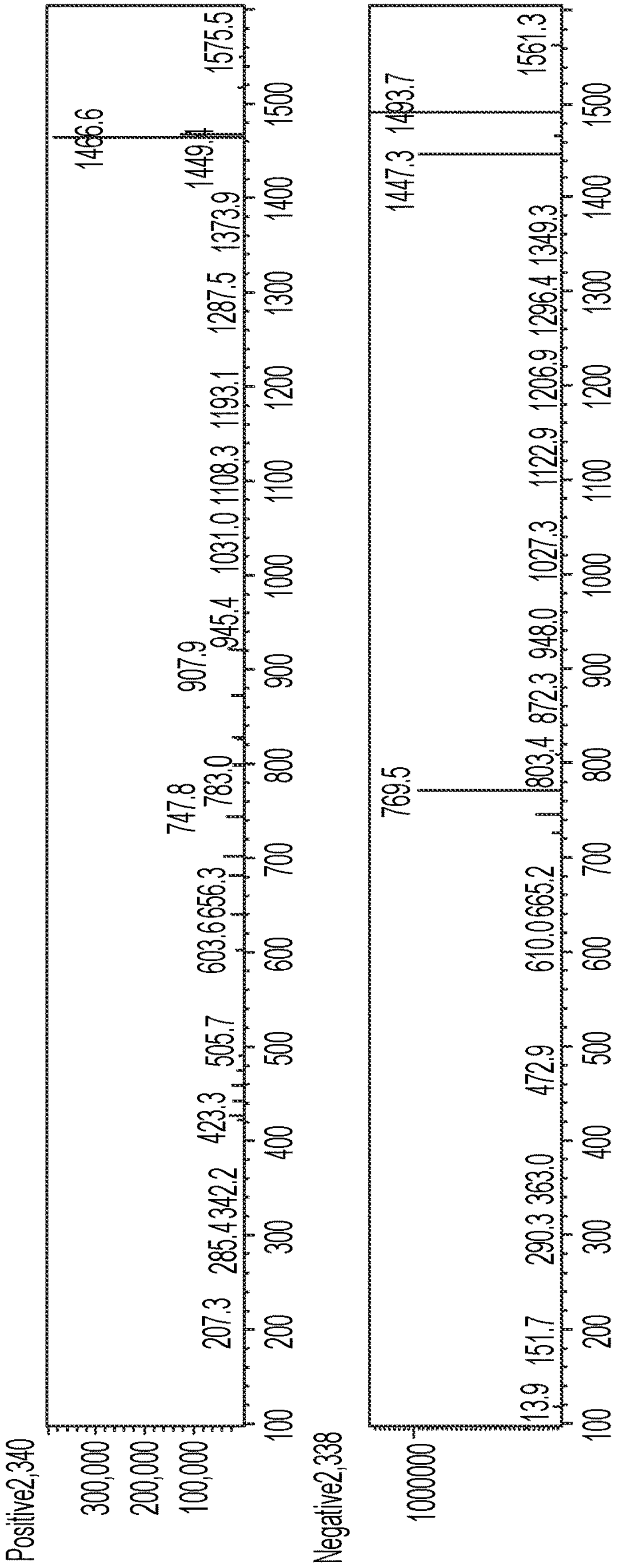
Figure 44:
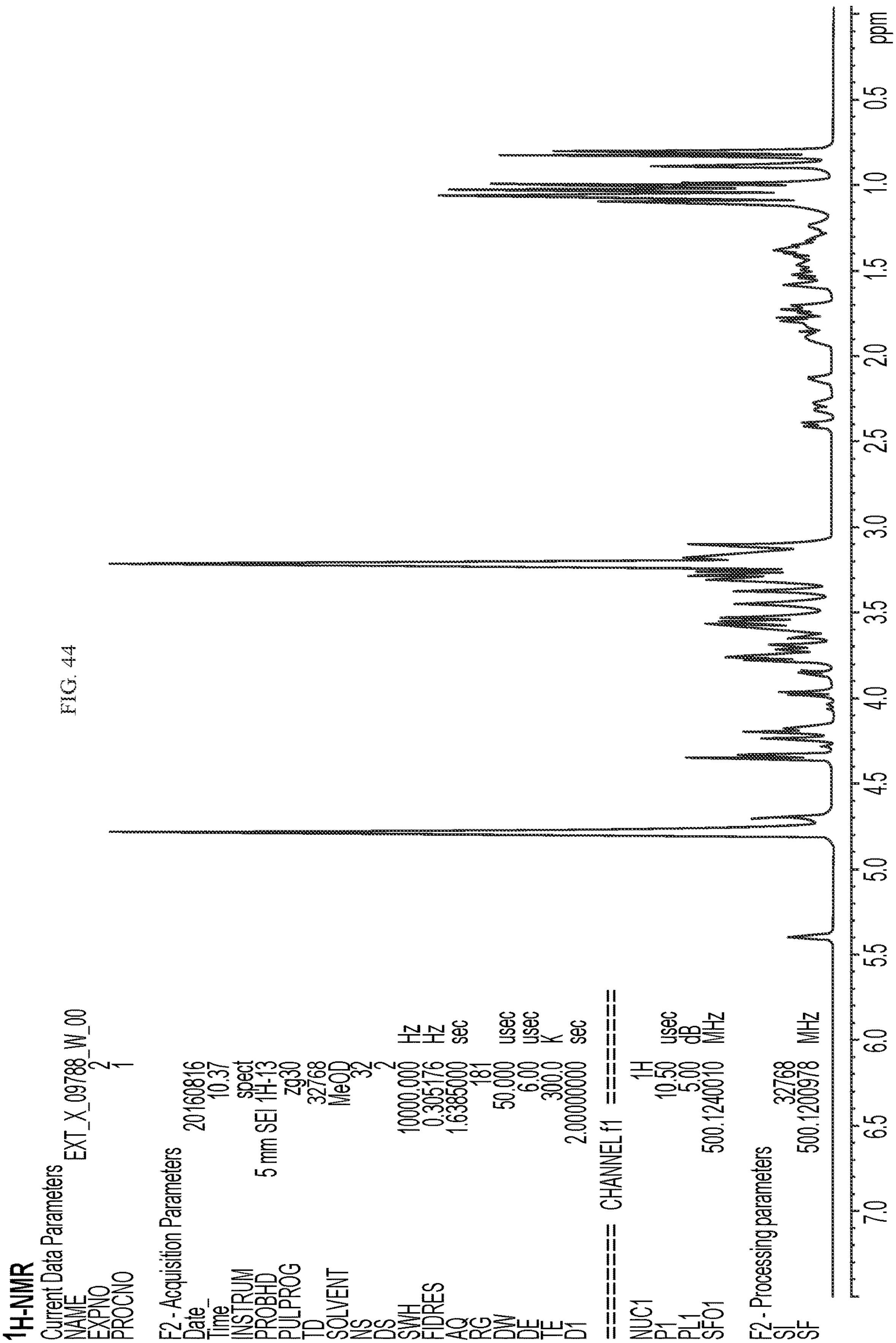
FIG. 44: 1H NMR spectrum of compound 11
Figure 45A:
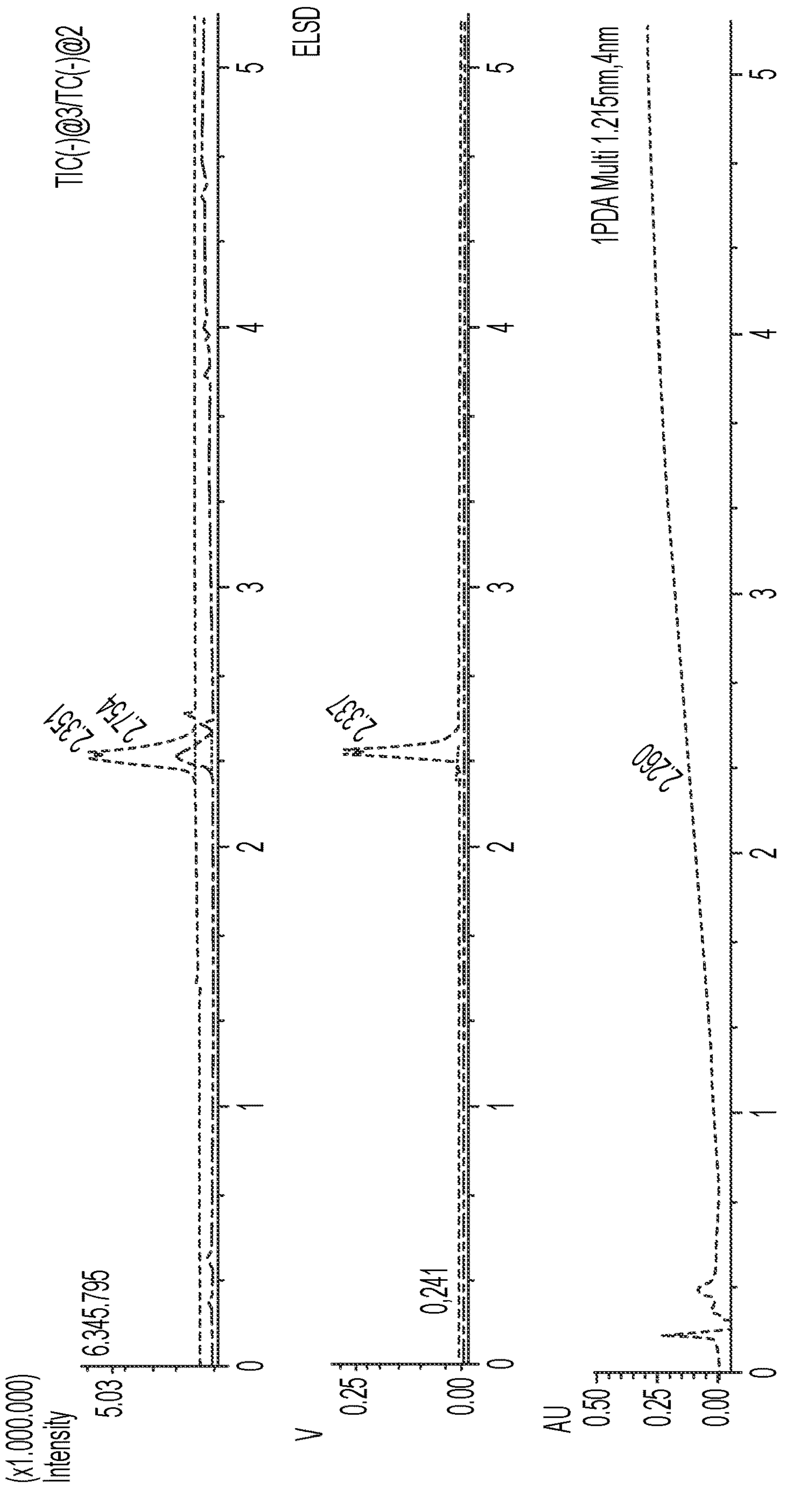
FIGS. 45A-45B: LCMS of compound 12
Figure 45B:
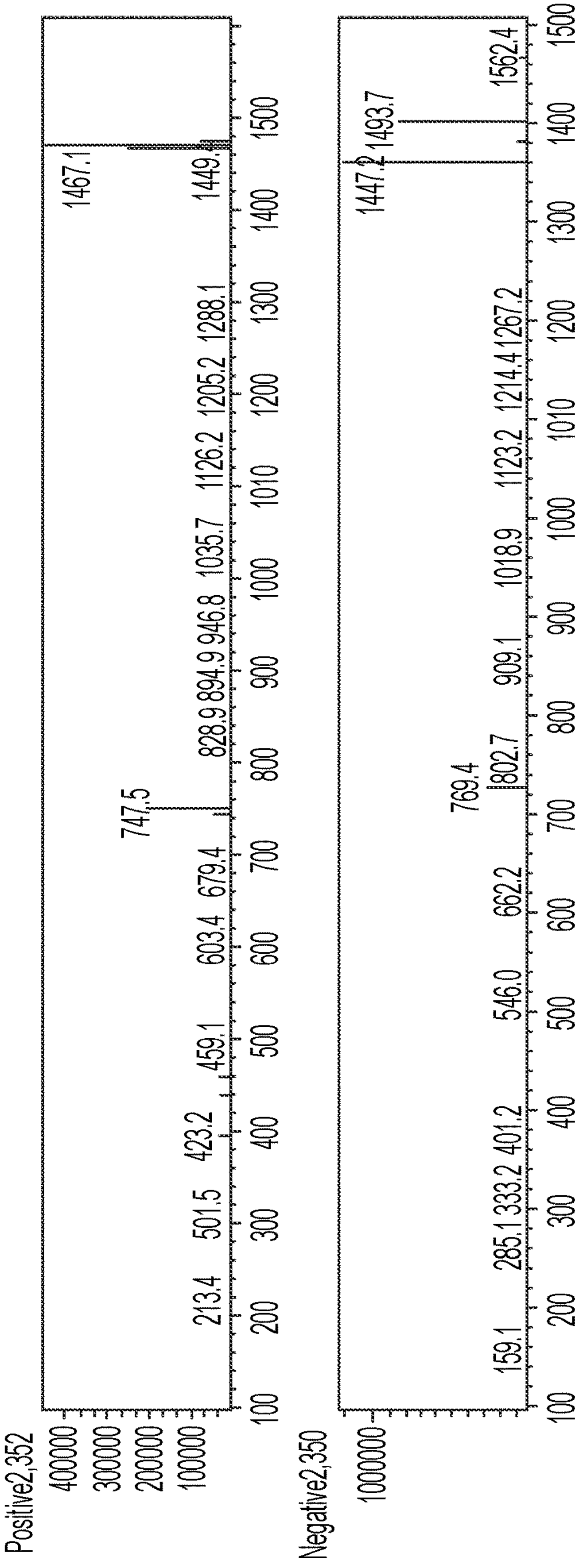
Figure 48:
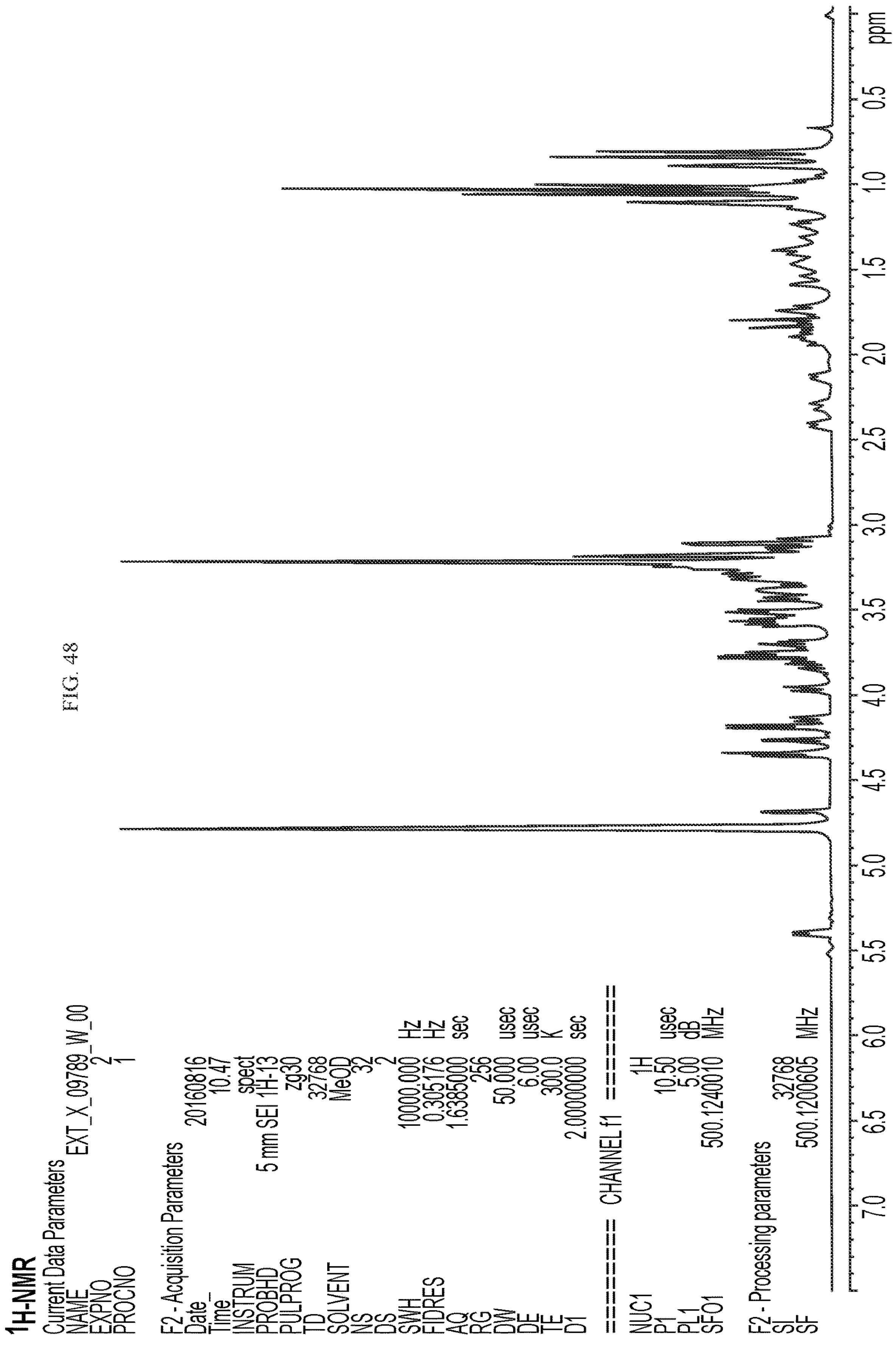
FIG. 48: 1H NMR spectrum of compound 12
Figure 49A:
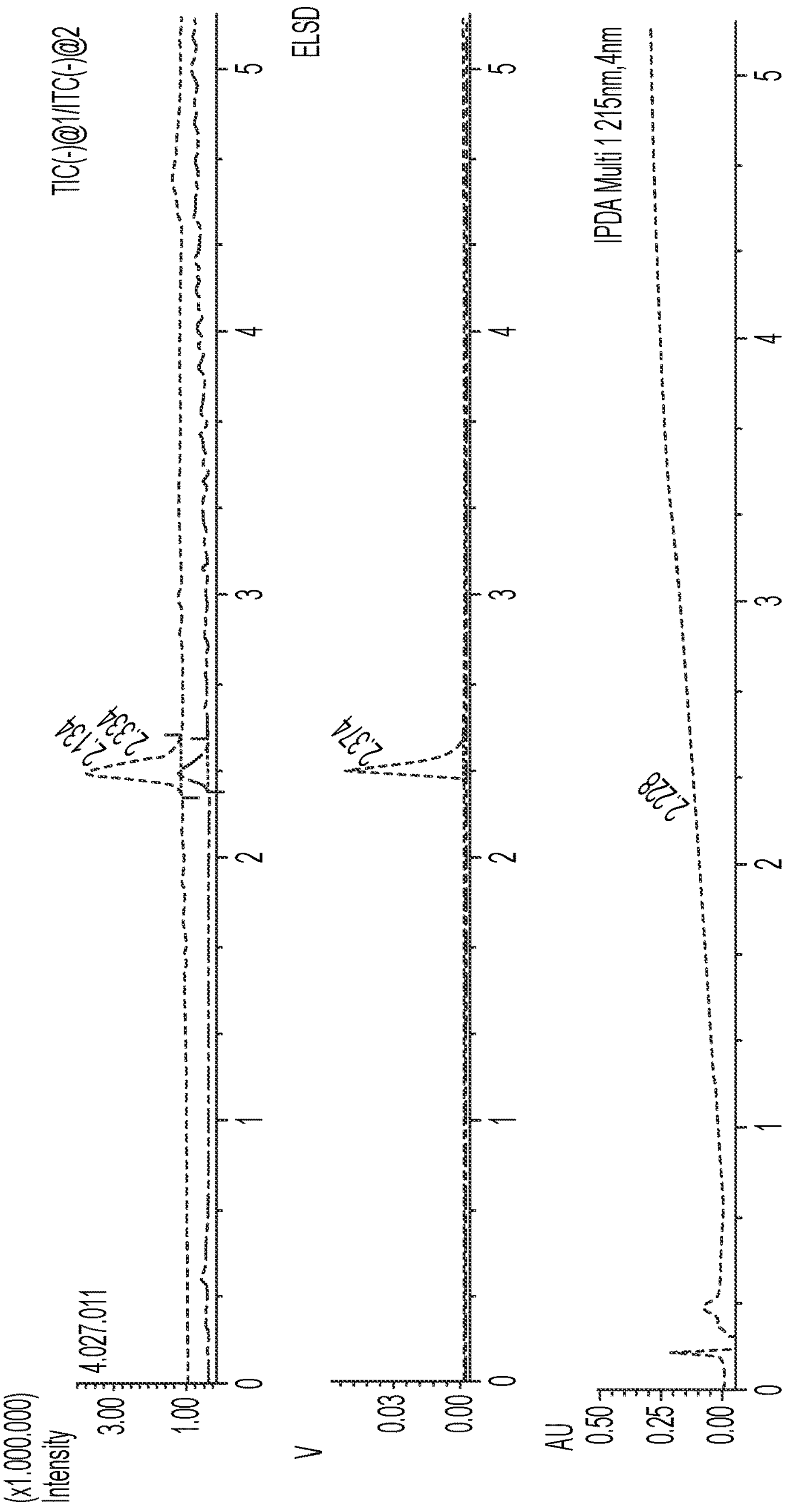
FIGS. 49A-49B: LCMS of compound 13
Figure 49B:
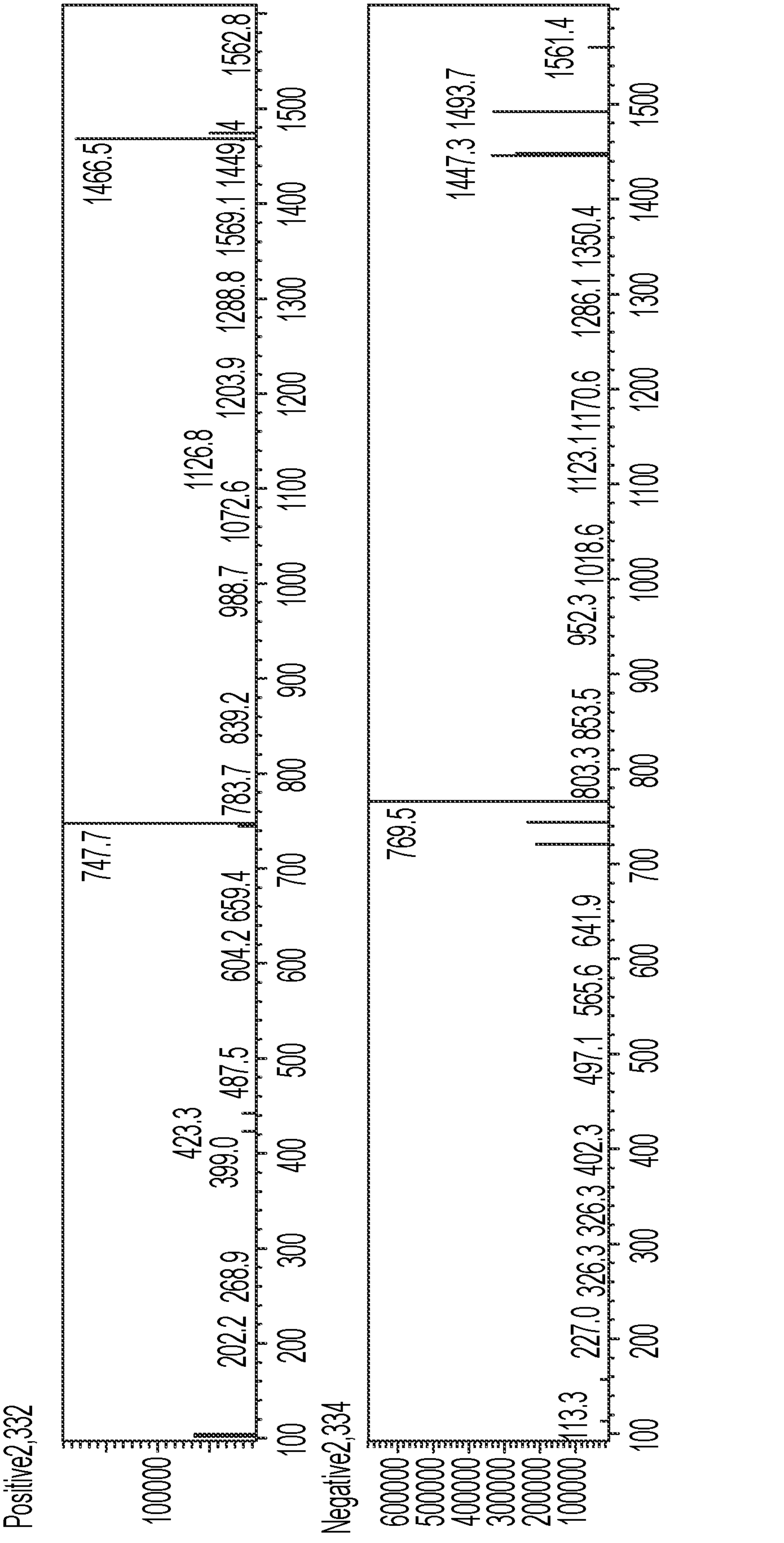
Figure 52:
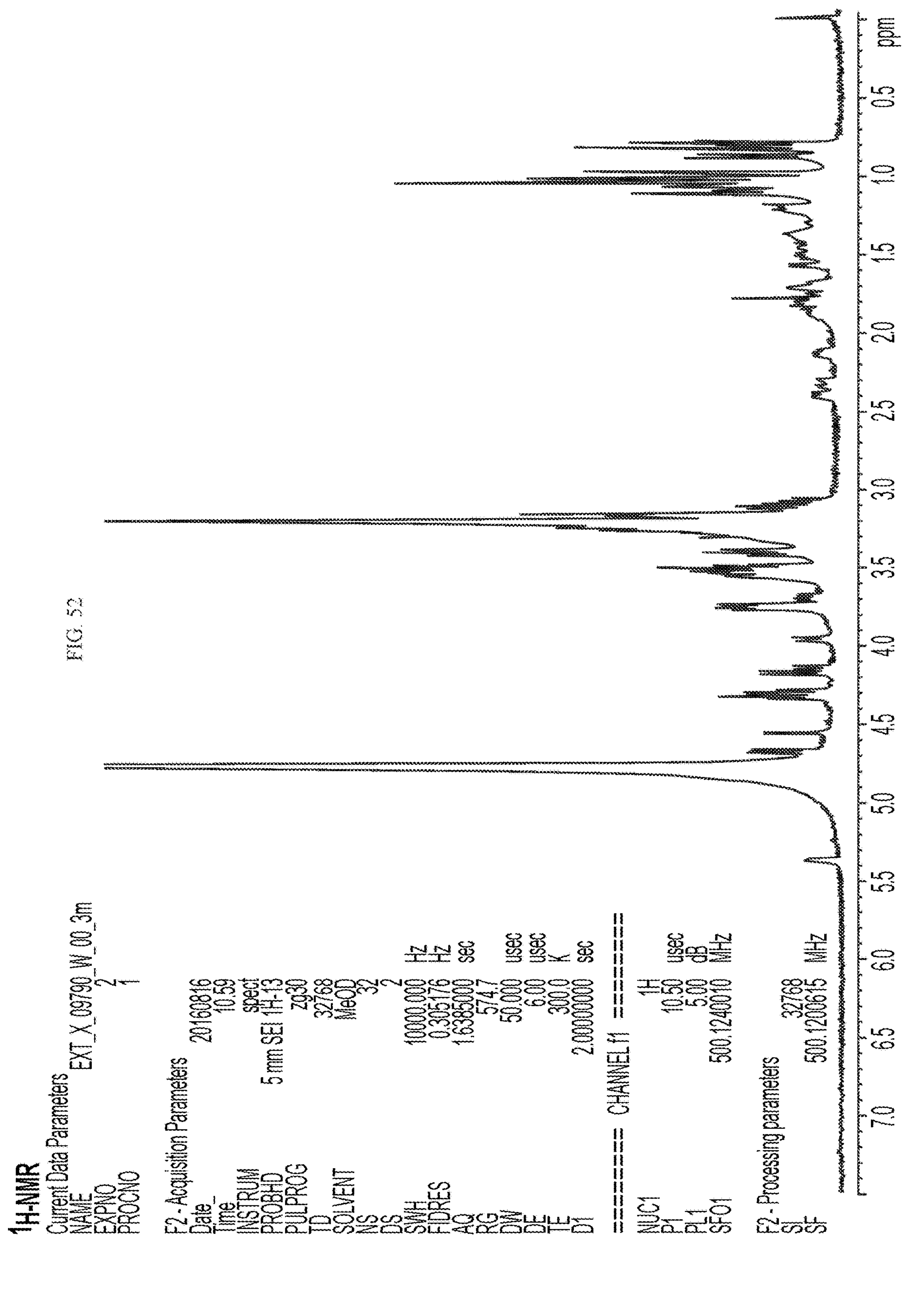
FIG. 52: 1H NMR spectrum of compound 13
Figure 53A:
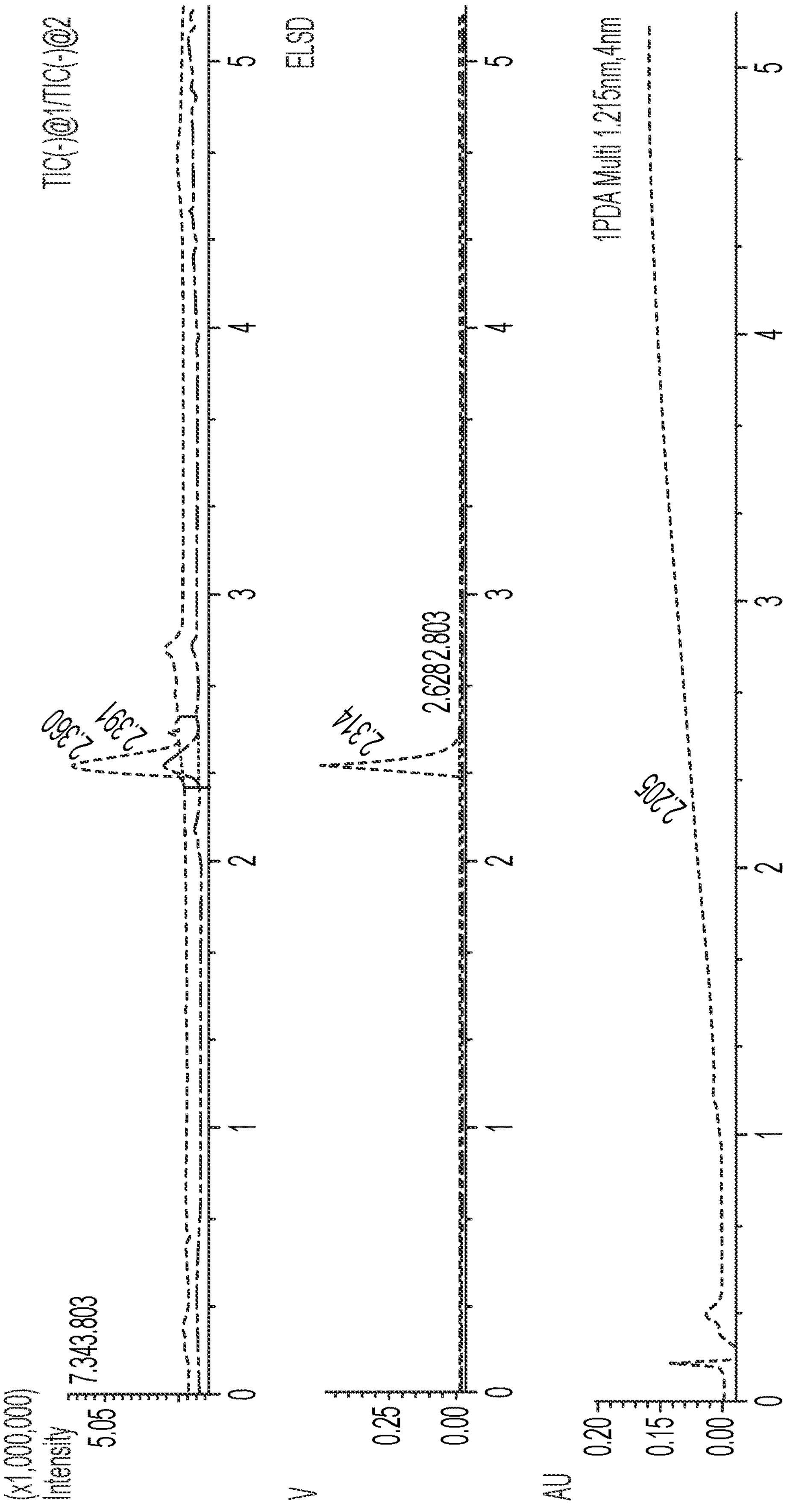
FIGS. 53A-53B: LCMS of compound 14
Figure 53B:
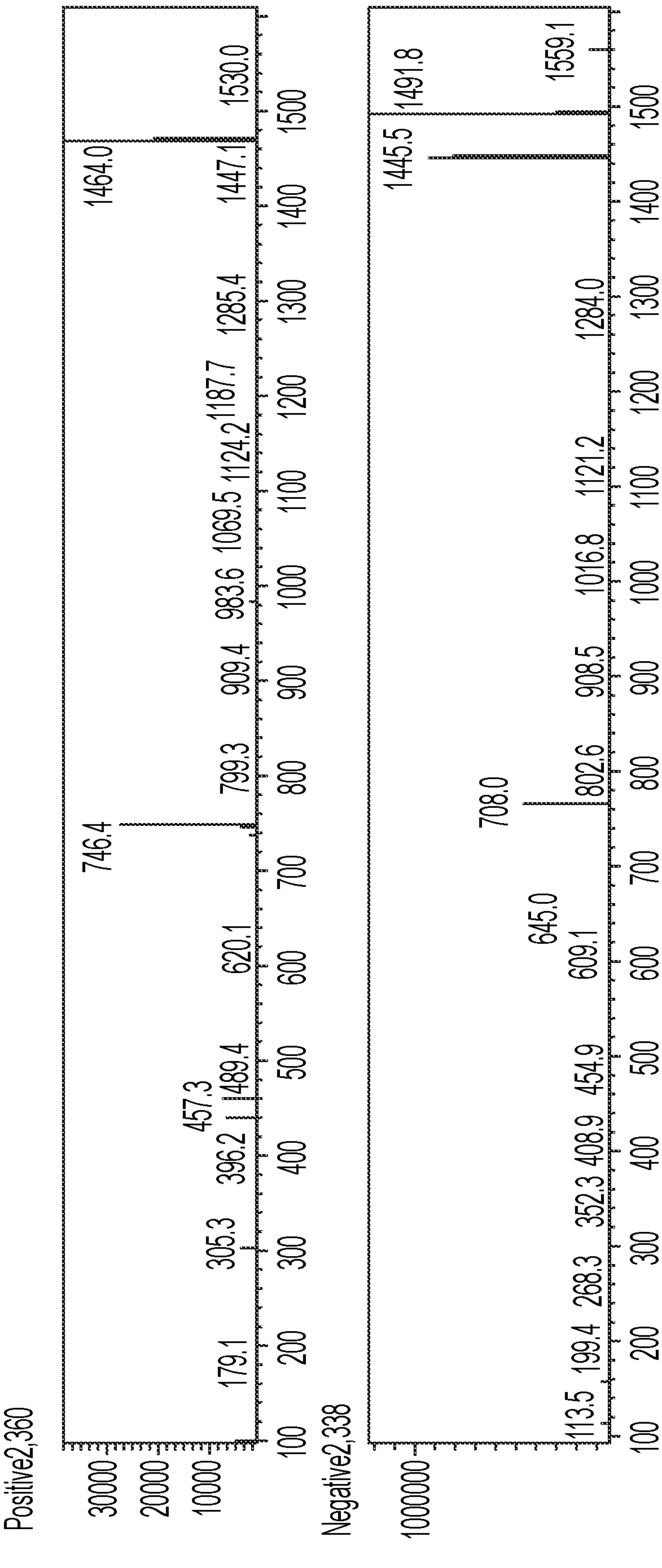
Figure 56:
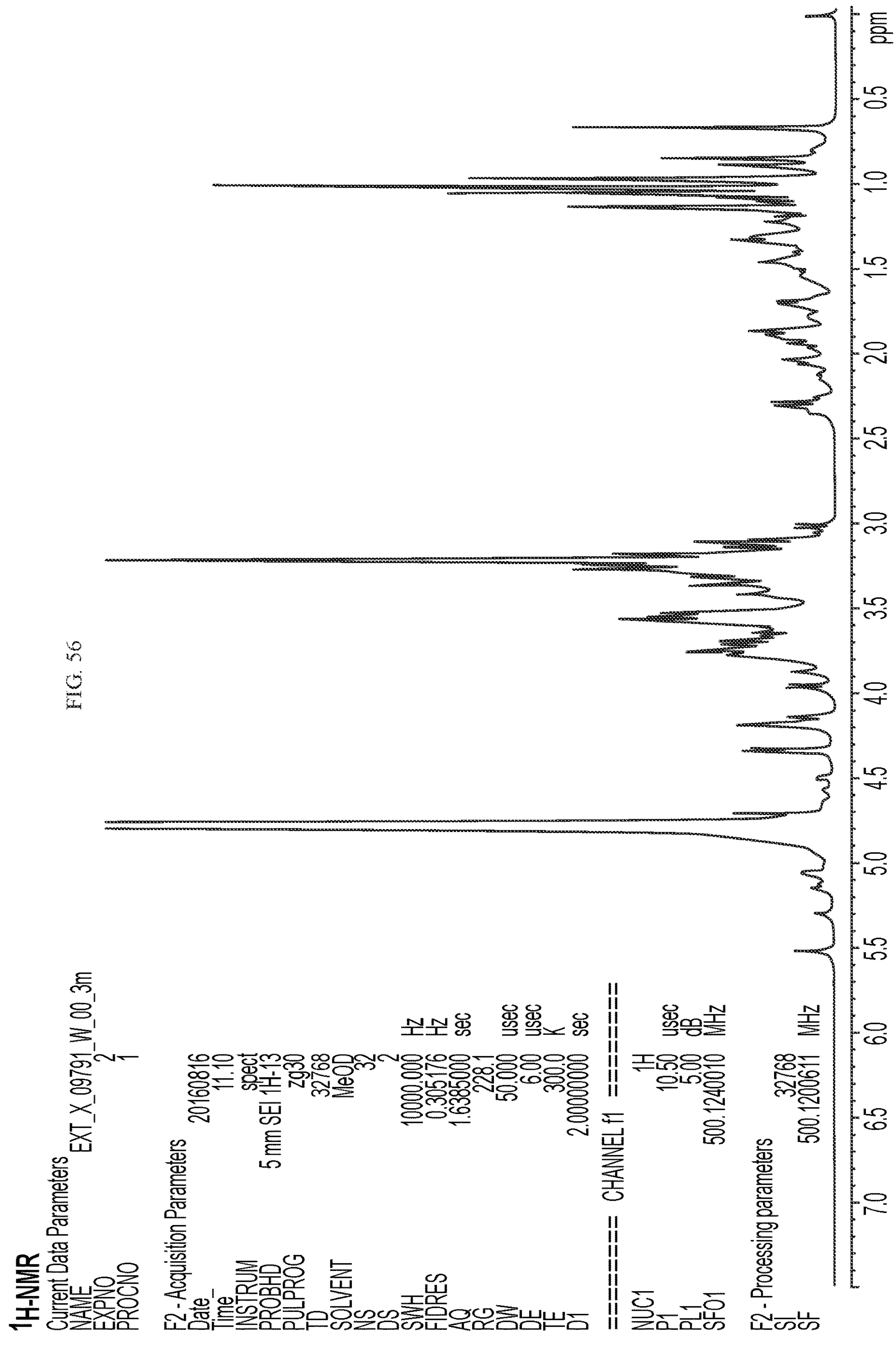
FIG. 56: 1H NMR spectrum of compound 14
Figure 57A:
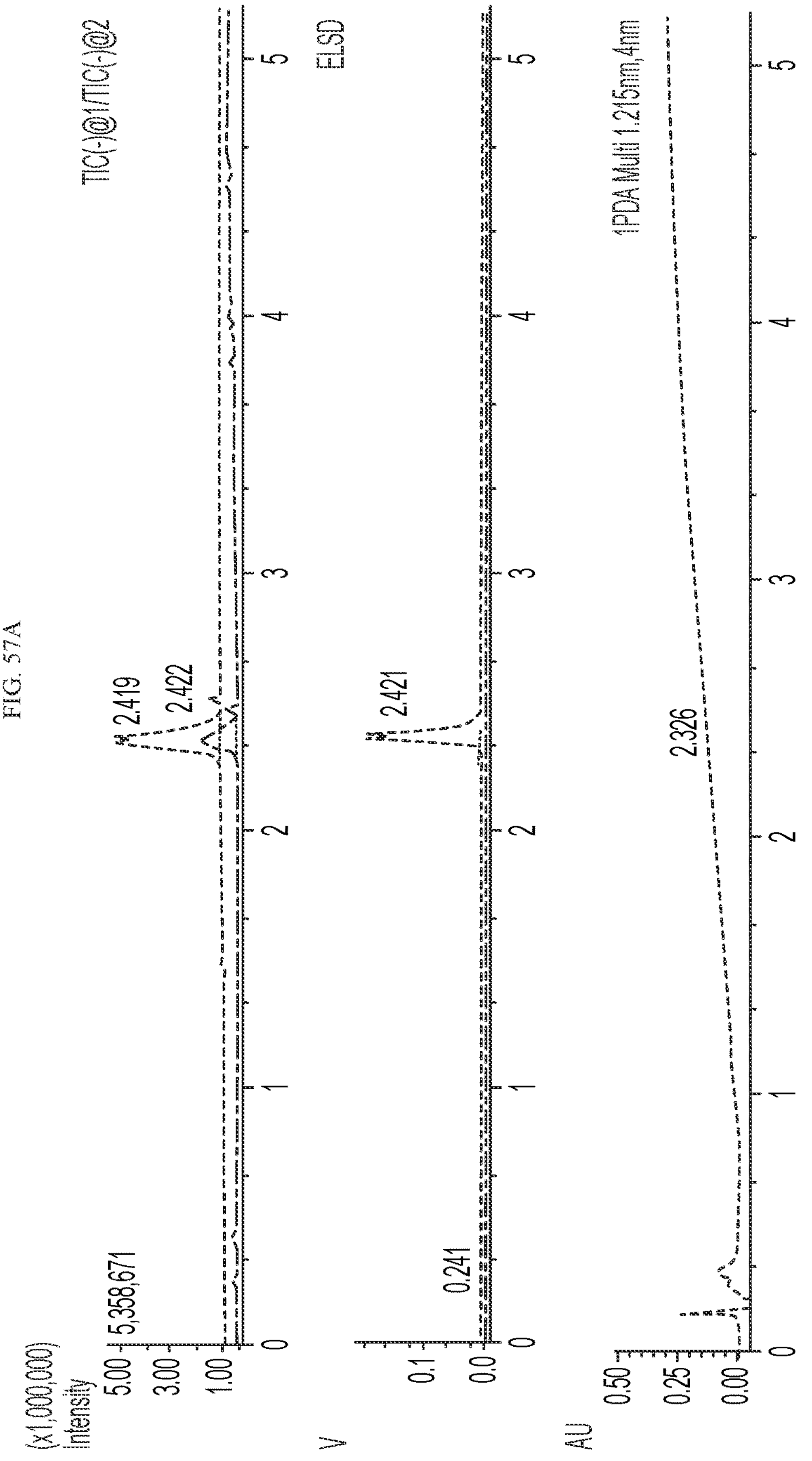
FIGS. 57A-57B: LCMS of compound 15
Figure 57B:
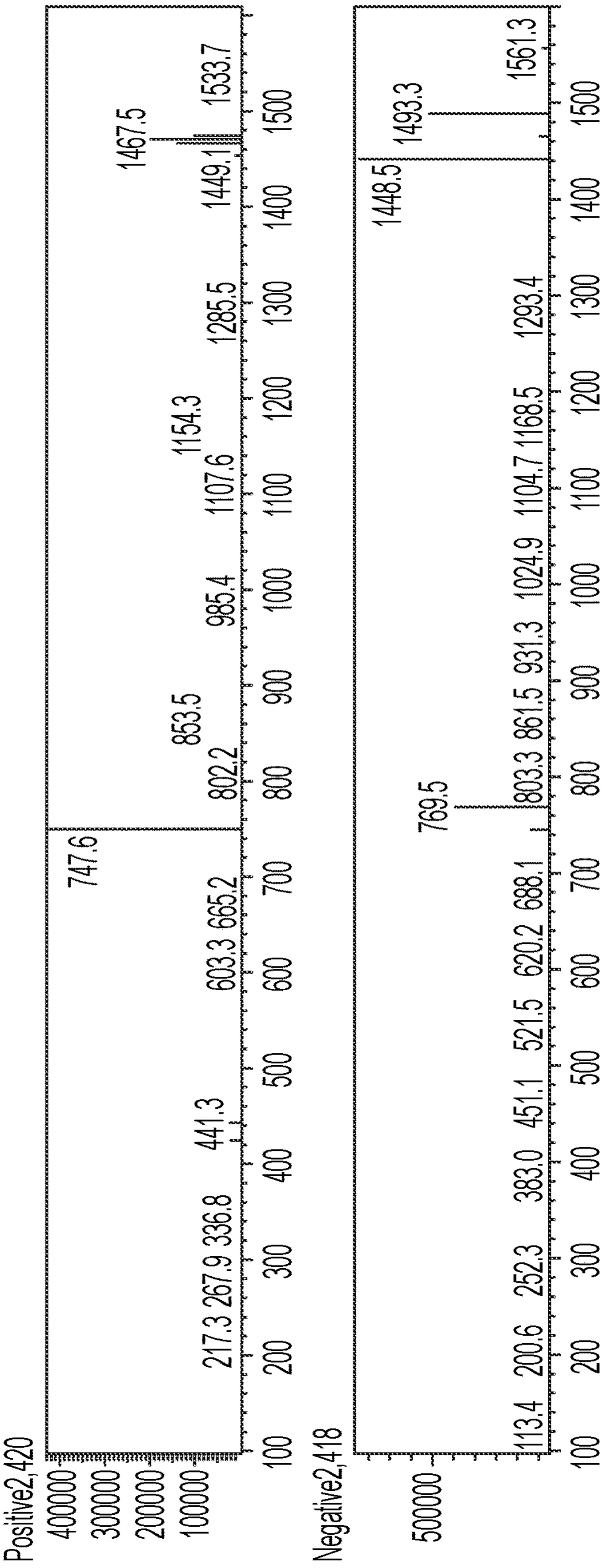
Figure 60:
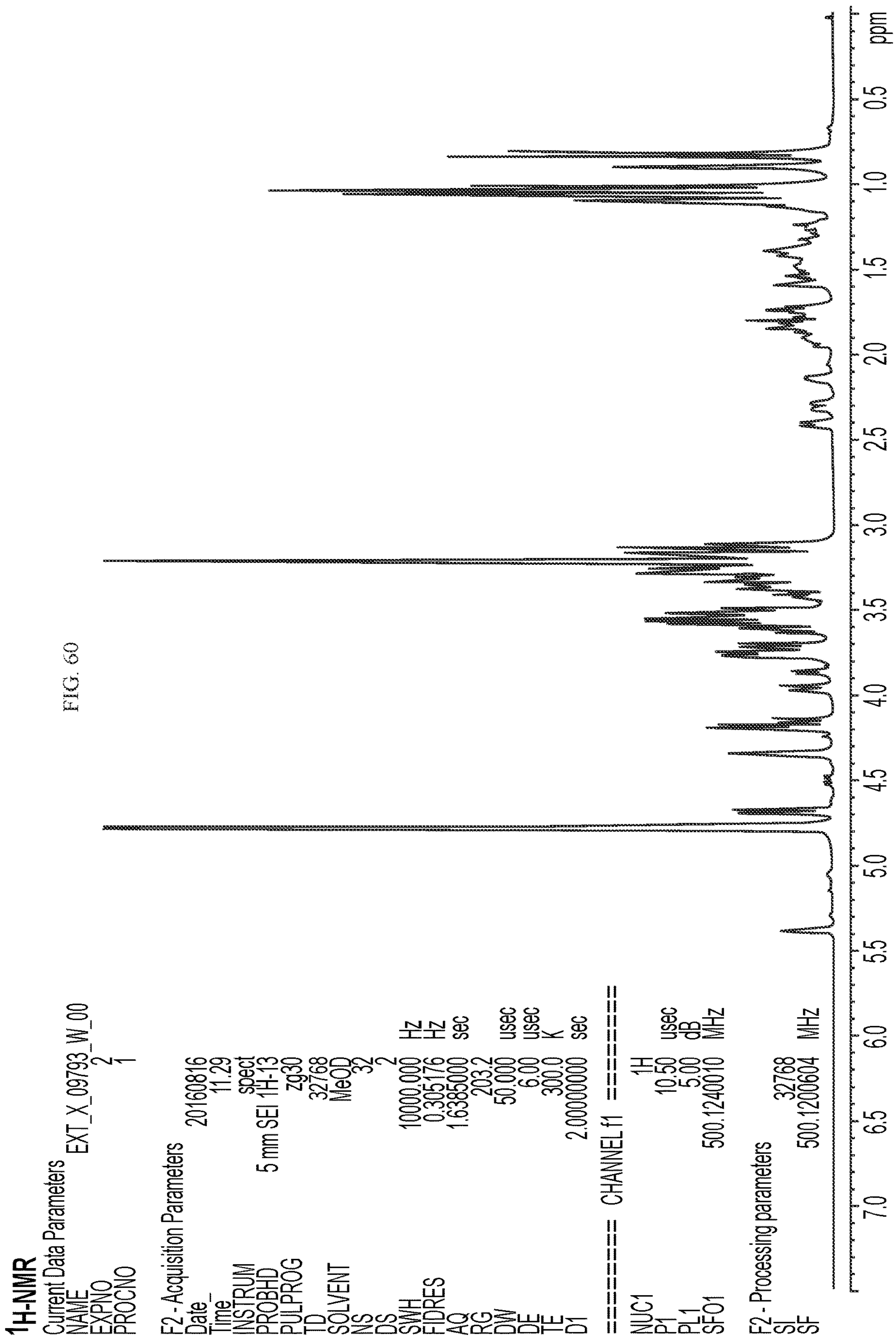
FIG. 60: 1H NMR spectrum of compound 15

Hereinafter the term "mogroside(s)" refers to compound(s) 1-15 (-FIG. 1-15 respectively).

The process of purification of mogrosides of the present invention comprises methods described in U.S. Patent Application No. 61/379,729 (filed Sep. 3, 2010), U.S. patent application Ser. No. 13/219,721 (filed Aug. 29, 2011), now patented as U.S. Pat. No. 9,101,162, and U.S. patent application Ser. No. 14/792,594 (filed Jul. 6, 2015), which was published as US Patent Application Publication No. 2015/0305381, which are incorporated by reference herein in their entirety.

The process of the present invention may further comprise isolation and purification of mogrosides using chromatography system.

In one embodiment of present invention a solution comprising at least one mogroside was passed through a HPLC column and fractions comprising mogrosides were collected. The HPLC column can be any suitable HPLC analytical or preparative scale column. The fractions may be eluted by adding an appropriate eluent. The eluent can be any suitable solvent or combination of solvents. In one embodiment, the eluent is water and/or acetonitrile. The method may optionally comprise additional steps, such as removal of solvents from the eluted solution to provide a concentrate comprising at least one mogroside.

In one embodiment, the following chromatography systems were used for isolation and purification of mogrosides. The mogrosides sample from a natural source was subjected to preparative HPLC using a commercial polyamine column, eluting with a mobile phase comprising acetonitrile and water. The mogrosides fraction from this step was further subjected to preparative HPLC using a commercial C18 column, eluting with a mobile phase comprising acetonitrile and water. Individual fractions from this step were further subjected to analytical-preparative HPLC using a commercial C18 column, eluting with a mobile phase comprising acetonitrile and water. The results of isolation and purification are summarized in Table 2. The purity of the isolated mogroside samples was suitable for NMR and HPLC-MS analysis.

TABLE 2

| Column | Loading Material | Fractions collected | Novel Mogroside compound(s) |
|---|---|---|---|
| Polyamine | Commercial Mogrosides extract | 1 combined fraction | Compounds 8-15 |
| Preparative C18 | Fraction from Polyamine column | Fraction 1 | Compounds 8 + 9 |
| | | Fraction2 | Compounds 10 + 11 |
| | | Fraction3 | Compound 12 |
| | | Fraction4 | Compounds 13 + 14 |
| | | Fraction 5 | Compound 15 |
| Analytical Preparative C18 | Fraction 1 | Individual peak | Compound 8 |
| | | Individual peak | Compound 9 |
| | Fraction2 | Individual peak | Compound 10 |
| | | Individual peak | Compound 11 |
| | Fraction4 | Individual peak | Compound 13 |
| | | Individual peak | Compound 14 |

In one embodiment, the fractions comprising mogrosides were dried to produce compositions comprising at least one mogroside.

The compositions comprising at least one mogroside can be also produced from new cultivars of *Siraita grosvenorii* plant which have increased content of mogrosides.

The compositions comprising at least one mogroside can be also produced by fermentation of recombinant microbial hosts selected from genera *Candida, Cyberlindnera, Kluyveromyces, Meyerozyma, Pischia, Rhodosporidium, Zygosaccharomyces, Saccharomyces, Aspergillus, Hansenula, Humicola, Trichosporon, Brettanomyces, Pachysolen, Yarrowia, Yamadazyma, Schizosaccharomyces, Ashbya, Cyberlindnera, Pichia, Arxula, Xanthophyllomyces* or *Escherichia*. Non-limiting examples of microbial strains include *Arthrobacter globiformis, Aspergillus niger, Aspergillus oryzae, Bacillus lichenformis, Bacillus sphaericus, Bacillus subtilis, Brevibacterium linens, Candida utilis, Candida vini, Corynebacterium glutamicum, Cyberlindnera jadinii, Cyberlindnera* sp., *Debaryomyces hansenii,*

*Fusarium semitectum, Hypomyces armeniacus, Kluyveromyces lactis, Kluyveromyces marxianus, Kocuria rhizophila, Lactobacillus brevis, Lactobacillus casei, Lactobacillus pentoses, Lactobacillus plantarum, Lactobacillus reuteri, Meyerozyma guilliermondii, Microbacterium* sp., *Micrococcus luteus, Mucor hiemalis, Mucor racemosus, Penicillium roqueforti, Pichia guilliermondii, Pichia jadinii, Pichia pastoris, Pseudomonas jluorescens, Pseudomonas stutzeri, Rhodosporidium* sp., *Rhodosporidium toruloides, Rhodotorula mucilaginosa, Rhodotorula rubra, Rhodotorula* sp., *Saccharomyces bayanus, Saccharomyces cerevisiae, Saccharomyces pastorianus, Streptomyces a/bus, Streptomyces coelicolor, Streptomyces griseus, Streptomyces lividans, Torulaspora delbrueckii, Trichosporon laibachii, Trichosporon oleaginosus, Yarrowia lipolytica, Zygosaccharomyces rouxii, Zymomonas mobilis.*

The compositions comprising at least one mogroside can be also produced by biotransformation using suitable biocatalysts.

The compositions comprising at least one mogroside can be also produced by chemical synthesis from precursor compounds.

One embodiment of present invention is a composition comprising at least one mogroside.

In some embodiments, at least one mogroside imparts sweet taste.

In one embodiment, the present invention is a sweetener composition comprising at least one mogroside.

In another embodiment, the present invention is a flavor-enhancing composition comprising at least one mogroside, wherein the mogroside is present in an amount effective to provide a concentration at or below the threshold flavor recognition level of the mogroside when the flavor-enhancing composition is added to a consumable. In a particular embodiment, the mogroside is present in an amount effective to provide a concentration below the threshold flavor recognition level of the mogroside when the flavor-enhancing composition is added to a consumable. In one embodiment, the mogroside is present in an amount effective to provide a concentration at least about 1%, at least about 5%, at least about 10%, at least about 15,% at least about 20% or at least about 25% or more below the threshold flavor recognition level of the mogroside when the flavor-enhancing composition is added to a consumable.

In yet another embodiment, the present invention is a sweetness-enhancing composition comprising at least one mogroside, wherein the mogroside is present in an amount effective to provide a concentration at or below the threshold sweetness recognition level of the mogroside when the sweetness-enhancing composition is added to a consumable. In a particular embodiment, the mogroside is present in an amount effective to provide a concentration below the threshold sweetness recognition level of the mogroside when the sweetness-enhancing composition is added to a consumable. In one embodiment, the mogroside is present in an amount effective to provide a concentration at least about 1%, at least about 5%, at least about 10%, at least about 15,% at least about 20% or at least about 25% or more below the threshold sweetness recognition level of the mogroside when the sweetness-enhancing composition is added to a consumable.

In yet another embodiment, the present invention is a consumable comprising at least one mogroside. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising a at least one mogroside. In a particular embodiment, the mogroside is present in the beverage at a concentration that is above, at or below the threshold sweetness recognition concentration of the mogroside.

In another particular embodiment, the present invention is a beverage product comprising a at least one mogroside. In a particular embodiment, the mogroside is present in the beverage product at a concentration that is above, at or below the threshold flavor recognition concentration of the mogroside.

In another aspect, the present invention is a method of preparing a consumable comprising (i) providing a consumable matrix and (ii) adding at least one mogroside to the consumable matrix to provide a consumable. In a particular embodiment, the mogroside is present in the consumable in a concentration above, at or below the threshold sweetness recognition of the mogroside. In another particular embodiment, the mogroside is present in the consumable in a concentration above, at or below the threshold flavor recognition of the mogroside.

In a particular embodiment, the present invention is a method of preparing a beverage comprising (i) providing a beverage matrix and (ii) adding at least one mogroside to the consumable matrix to provide a beverage. In a particular embodiment, the mogroside is present in the consumable in a concentration above, at or below the threshold sweetness recognition of the mogroside. In another particular embodiment, the mogroside is present in the consumable in a concentration above, at or below the threshold flavor recognition concentration of the mogroside.

In another aspect, the present invention is a method of enhancing the sweetness of a consumable comprising (i) providing a consumable comprising at least one sweet ingredient and (ii) adding at least one mogroside to the consumable to provide a consumable with enhanced sweetness, wherein the mogroside is present in the beverage with enhanced sweetness at a concentration at or below the threshold sweetness recognition concentration of the mogroside.

In a particular embodiment, the present invention is a method of enhancing the sweetness of a beverage comprising (i) providing a beverage comprising at least one sweet ingredient and (ii) adding at least one mogroside to the beverage to provide a beverage with enhanced sweetness, wherein the mogroside is present in the beverage with enhanced sweetness at a concentration below the threshold sweetness recognition concentration of the mogroside. In one embodiment, the concentration of the mogroside is present in the beverage with enhanced sweetness at a concentration that is at least about 1%, at least about 5%, at least about 10%, at least about 15%, at least about 20%, or at least about 25% or more below the threshold sweetness recognition concentration of the mogroside.

In a further aspect, the present invention is a method of enhancing the flavor of a consumable comprising (i) providing a consumable comprising at least one flavor ingredient and (ii) adding at least one mogroside to the consumable to provide a consumable with enhanced flavor, wherein the mogroside in present in the consumable with enhanced flavor at a concentration at or below the threshold flavor recognition concentration of the mogroside.

In a particular embodiment, the present invention is a method of enhancing the flavor of a beverage comprising (i) providing a beverage comprising at least one flavor ingredient and (ii) adding at least one mogroside to the beverage to provide a beverage with enhanced flavor, wherein the mogroside is present in the beverage with enhanced flavor in a concentration at or below the threshold flavor recognition concentration of the mogroside. In one embodiment, the concentration of the mogroside is present in the beverage with enhanced sweetness at a concentration that is at least about 1%, at least about 5%, at least about 10%, at least about 15%, at least about 20%, or at least about 25% or more below the threshold flavor recognition concentration of the mogroside.

In the above methods, the mogroside may be added as such, or in the form of a composition comprising the mogroside. When the mogroside is provided as a composition, the concentration of the mogroside in the composition is effective to provide a concentration above, at or below the threshold flavor or sweetener composition of the mogroside, when the composition is added to the consumable, e.g., the food or beverage.

In some embodiments, the compositions of the present invention comprise one or more additional mogrosides, where the additional mogrosides are selected from, but not limited to, the group consisting of Luo han guo extract, by-products of other mogrosides' isolation and purification processes, a commercially available Luo han guo extract, mogroside IIE, mogroside IB, mogroside III, mogroside IV, mogroside V, 11-oxo-mogroside V, mogroside VI, siamenoside I, grosmomoside I, neomogroside, and other mogrol and oxo-mogrol glycosides occurring in *Siraitia grosvenorii* fruit and combinations thereof.

In other embodiments, the compositions of the present invention comprise one or more sweeteners or additional sweeteners. In one embodiment, the additional sweetener is a natural sweetener or a synthetic sweetener. In a particular embodiment, the additional sweetener is a high intensity sweetener. In a particular embodiment, the additional sweetener is a mogroside.

In some embodiments, the compositions of the present invention comprise one or more additives. In a particular embodiment, the additive is selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

In some embodiments, the compositions of the present invention comprise one or more functional ingredients. In a particular embodiment, the functional ingredient is selected from the group consisting of caffeine, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In a particular embodiment, the present invention is a consumable comprising a mogroside and one or more additional mogrosides, sweeteners, additional sweeteners, additives or functional ingredients.

In another particular embodiment, the present invention is a beverage comprising at least one mogroside and one or more additional mogrosides, sweeteners, additional sweeteners, additives or functional ingredients.

The compositions comprising mogrosides can be used either alone or in combination with at least one other sweetener in consumables including food, beverage, pharmaceutical composition, tobacco, nutraceutical, oral hygienic composition, or cosmetic. The other sweeteners are selected from the group including sucrose, glyceraldehyde, dihydroxyacetone, erythrose, threose, erythrulose, arabinose, lyxose, ribose, xylose, ribulose, xylulose, allose, altrose, allulose, galactose, glucose, gulose, idose, mannose, talose, fructose, psicose, sorbose, tagatose, mannoheptulose, sedoheltulose, octolose, fucose, rhamnose, arabinose, turanose, sialose, inulin, inulooligosaccharides, fructooligosaccharides, high fructose corn syrup (HFCS), maltodextrin, coupling sugar, honey, stevia, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside 0, dulcoside A, dulcoside B, rubusoside, steviolbioside, stevioside, other steviol glycosides occurring in *Stevia rebaudiana* plant, biosynthetic steviol glycosides, glycosylated steviol glycosides, glucosylated steviol glycosides (GSGs), mogroside N, mogroside V, mogroside VI, Luo han guo, siamenoside, other mogrosides occurring in *Siraitia grosvenorii* fruits, monatin and its salts, curculin, glycyrrhizic acid and its salts, thaumatin, monellin, mabinlin, brazzein, hemandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I, sugar alcohols, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof.

The following examples are provided for illustrating the process and column system of the present invention.

EXAMPLE 1

Purification of Mogrosides

Luo Han Guo fruit extract, commercialized by PureCircle Sdn Bhd (Malaysia) containing 50.72% Mogroside V, 8.58% 11-oxo-Mogroside V, 5.67% Siamenoside I, 5.28% Grosmomoside I and about 3% of mogrosides was separated by a column system described in U.S. 61/379,729, U.S. Pat. No. 9,101,162 and U.S. Ser. No. 14/792,594 to obtain an enriched composition comprising about 20% of mogrosides, 31.1% Mogroside V, 2.8% 11-oxo-Mogroside V, 1.6% Siamenoside I, and 1.1% Grosmomoside I, all percentages being on w/w dried basis. The enriched composition was concentrated to approximately 50% solids content and subjected to preparative HPLC using YMC Polyamine II column (250×20 mm; 5 μm) at ambient temperature, eluting with a mobile phase consisting of acetonitrile and water with 75:25 (vol/vol) ratio (23 mL/min flowrate).

The mogrosides fraction from the preceding step was concentrated to about 7% solids content and was further subjected to preparative HPLC using Zorbax SB-C18 (9.4×50 mm; 5 m) column, eluting with a mobile phase consisting of acetonitrile and water with 14:86 vol/vol ratio (35 mL/min flowrate). Five fractions were collected (Table 2) and analysed by analytical-preparative HPLC for purity assessment. Fraction 1 contained two peaks corresponding to mogroside compounds 8 and 9, fraction 2 contained two peaks corresponding to mogroside compounds 10 and 11, fraction 3 contained one major peak corresponding to mogroside compound 12, fraction 4 contained at least two peaks corresponding to mogroside compound 13 and 14, and fraction 5 contained one major peak corresponding to mogroside compound 15. Fractions 1, 2 and 4 were further subjected to analytical-preparative separation described below, while fractions 3 and 5 were concentrated, dried and subjected to NMR and HPLCMS analyses.

Fractions 1, 2 and 4 from the preceding step were subjected to analytical-preparative HPLC, eluting with a mobile phase consisting of a mixture of acetonitrile and water with 19:81 (vol/vol) ratio for fraction 1 and 25:75 (vol/vol) ratio for fractions 2 and 4. The column was Poroshell 120 SB-C18 (4.6×150 mm; 2.7 μm), operated at 0.5 mL/min flowrate. The purified fractions containing individual peaks were concentrated, dried and subjected to NMR and HPLCMS analyses.

EXAMPLE 2

NMR Analysis of the Mogrosides

NMR samples were dissolved in methanol-d4 and analysed by ID and 2D NMR methods. Noteworthy in the NMR analysis is the assignment of oxo- or hydroxy-functional group at Cl 1—for oxo—a typical 13C chemical shift around 190-220 ppm was seen, whereas for hydroxy—a typical 13C chemical shift of around 65-85 ppm was seen. Also noteworthy is the assignment of alpha-glycosidic linkages for some mogroside compounds where a coupling constant of approximately 3.5 Hz is seen (for beta-glycosidic linkages the coupling constant is usually approximately 7-9 Hz). All mogroside compounds claimed in this application showed good purity required for structural elucidation. The acquired data was used for structure elucidation.

EXAMPLE 3

HPLCMS Analysis of the Mogrosides

HPLCMS were performed on Shimadzu MS 2020 on Cortecs UPLC C18 1.6 μm, 50×2.1 mm column, mobile phase A: 5 mM ammonium formate +0.1% formic acid, B: methanol:acetonitrile (1:1)+5 mM ammonium phosphate buffer +0.1% formic acid, injection volume 0.1-5 μl, detection ELSD (Sedex 85, pressure 4 bar, nebulizer temperature 35° C.), PDA 210-400 nm, gradient 5% B to 100% B in 4 min followed by 2 min 100% B, tlowrate 1 ml/min, scan 100-1600 amu, pos/neg switch. All mogroside compounds claimed in this application showed good purity required for HPLCMS analysis.

Based on NMR data acquired in Example 2 and the data acquired during HPLCMS analysis of mogrosides, the structures of mogroside compounds 1-15 were proposed.

EXAMPLE 4

Mogrosides Organoleptic Characteristics

The organoleptic properties of the enriched composition comprising about 20% (w/w) mogrosides (Example 1), the individual mogroside compounds, obtained from individual peak fractions of Example 1, were assessed in aqueous solutions isosweet to 5% sucrose. The assessment was conducted by 20 panelists in comparison with 5% isosweet aqueous solutions of commercial Luo Han Guo fruit extract of Example 1, highly purified (96.6% pure) Mogroside V sample (sourced from ChromaDex Inc., USA) and sucrose (5%). The results are summarized in Table 3.

TABLE 3

Novel Mogrosides (NM) Taste Properties

| Compounds | Sweetness potency (sucrose = 1) | Sweetness Lingering* | Bitterness* | Delayed sweetness onset* | Licorice taste* | Overall taste profile vs. su2ar |
|---|---|---|---|---|---|---|
| Enriched composition (20% NM) | 320 | 3 | 2 | 3 | 2 | pleasant |
| NM8 | 320 | 1 | 1 | 2 | 1 | sugar-like |
| NM9 | 300 | 2 | 1 | 2 | 1 | sugar-like |
| NM10 | 320 | 1 | 2 | 2 | 1 | sugar-like |
| NM11 | 310 | 1 | 2 | 2 | 1 | sugar-like |
| NM12 | 350 | 1 | 1 | 2 | 1 | sugar-like |
| NM13 | 310 | 2 | 1 | 3 | 1 | sugar-like |
| NM14 | 300 | 1 | 1 | 1 | 1 | sugar-like |
| NM 15 | 340 | 1 | 1 | 1 | 1 | sugar-like |
| Luo Han Guo extract | 300 | 5 | 5 | 5 | 5 | unpleasant |
| Purified Mogroside V | 360 | 5 | 4 | 5 | 4 | tolerable |
| Sucrose | 1 | 1 | 1 | 1 | 1 | NA |

*For "Sweetness Lingering", "Bitterness", "Delayed sweetness onset", and "Licorice taste" characteristics the panelists score between 1 to 5, where the lower score represents more pleasant taste sensation by panelist The sensory evaluation results show all mogrosides possess significantly better taste profile compared to commercially available mogroside samples. The data for enriched composition (containing about 20% mogrosides) also shows that mogrosides can improve the overall taste characteristics of mogrosides mixtures comprising less pleasant mogrosides such as Mogroside V.

EXAMPLES

Consumable Comprising Mogrosides.

Carbonated beverage samples were prepared according to formula presented

TABLE 4

Formula for carbonated beverages

| Ingredients | Quantity, % |
|---|---|
| Cola flavor | 0.340 |
| ortho-Phosphoric acid | 0.100 |
| Sodium citrate | 0.310 |
| Sodium benzoate | 0.018 |
| Citric acid | 0.018 |
| Mo}:!roside composition | 0.050 |
| Carbonated water | to 100 |

The following samples were used as "mogroside composition" in the formula. The enriched composition of Example 1 (comprising about 20% (w/w) mogrosides), the individual mogroside compounds, obtained from individual peak fractions of Example 1, commercial Luo Han Guo fruit extract of Example 1, highly purified (96.6% pure) Mogroside V sample (from ChromaDex Inc., USA). The sensory assessment of beverage samples was conducted by 20 panelists. The results are summarized in Table 5.

TABLE 5

Sensory evaluation of carbonated beverage samples

| "Mogroside composition" used in formula | Sweetness Lingering* | Bitterness* | Delayed sweetness onset* | Licorice taste* | Overall taste |
|---|---|---|---|---|---|
| Enriched composition (20% NM) | 2 | 2 | 2 | 2 | pleasant |
| NM8 | 1 | 1 | 2 | 1 | sugar-like |
| NM9 | 2 | 1 | 1 | 1 | sugar-like |
| NM1O | 1 | 2 | 2 | 1 | sugar-like |
| NM11 | 2 | 1 | 1 | 1 | sugar-like |
| NM 12 | 1 | 1 | 2 | 1 | sugar-like |
| NM13 | 1 | 2 | 2 | 1 | sugar-like |
| NM14 | 1 | 1 | 1 | 2 | sugar-like |
| NM 15 | 2 | 1 | 1 | 1 | sugar-like |
| Luo Han Guo extract | 5 | 5 | 5 | 5 | unpleasant |
| Purified Mogroside V | 5 | 4 | 5 | 5 | tolerable |

*For "Sweetness Lingering", "Bitterness", "Delayed sweetness onset", and "Licorice taste" characteristics the panelists score between 1 to 5, where the lower score represents more pleasant taste sensation by panelist The results showed the beverages prepared using the composition comprising mogrosides possessed the best organoleptic characteristics.

EXAMPLE 6

Consumable Comprising Mogrosides.

Chocolate samples were papered according to formula in Table 6.

TABLE 6

Formula for chocolate samples

| Ingredients | Quantity, % |
|---|---|
| Chocolate liquor | 30.0 |
| Cocoa butter | 11.5 |
| Milk powder | 14.0 |
| Sorbitol | 44.0 |
| Salt | 0.1 |
| Mogroside composition | 0.1 |
| Lecithin | 0.3 |

Chocolate liquor, cocoa butter, milk powder, sorbitol, salt, and the "mogroside composition" were kneaded sufficiently, and the mixture was then placed in a refiner to reduce its particle size for 24 hours. Thereafter, the content was transferred into a conche, the lecithin was added, and the composition was kneaded at 50° C. for 48 hours. Then, the content was placed in a shaping apparatus, and solidified.

The following samples were used as "mogroside composition" in the formula of Table 6. Enriched composition comprising about 20% (w/w) mogrosides (Example 1), the individual mogroside compounds, obtained from individual peak fractions of Example 1, commercial Luo Han Guo fruit extract of Example 1, highly purified (96.6% pure) Mogroside V sample sourced from ChromaDex Inc., (USA). The sensory assessment of chocolate samples was conducted by 20 panelists. The results are summarized in Table 7.

TABLE 7

Sensory evaluation of chocolate samples

| "Mogroside composition" used in formula | Sweetness Lin2er-in2* | Bitterness* | Licorice taste* | Overall taste |
|---|---|---|---|---|
| Enriched composition (20% NM) | 2 | 2 | 2 | pleasant |
| NM8 | 1 | 1 | 1 | sugar-like |
| NM9 | 2 | 2 | 1 | sugar-like |
| NM1O | 1 | 2 | 2 | sugar-like |
| NM11 | 1 | 1 | 1 | sugar-like |
| NM 12 | 2 | 1 | 2 | sugar-like |
| NM13 | 1 | 2 | 1 | sugar-like |
| NM14 | 1 | 1 | 2 | sugar-like |
| NM 15 | 2 | 2 | 1 | sugar-like |
| Luo Han Guo extract | 5 | 5 | 5 | unpleasant |
| Purified Mogroside V | 4 | 5 | 5 | tolerable |

*For "Sweetness Lingering", "Bitterness", and "Licorice taste" characteristics the panelists score between 1 to 5, where the lower score represents more pleasant taste sensation by panelist The results showed the chocolate samples prepared using the composition comprising mogrosides possessed the best organoleptic characteristics.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

We claim:
1. A consumable comprising at least one mogroside compound having a chemical structure selected from formulae 1, 2, 4, 5, 7, 8, 9, 11, 12, 14 and 15 as defined herein:
Formula 1
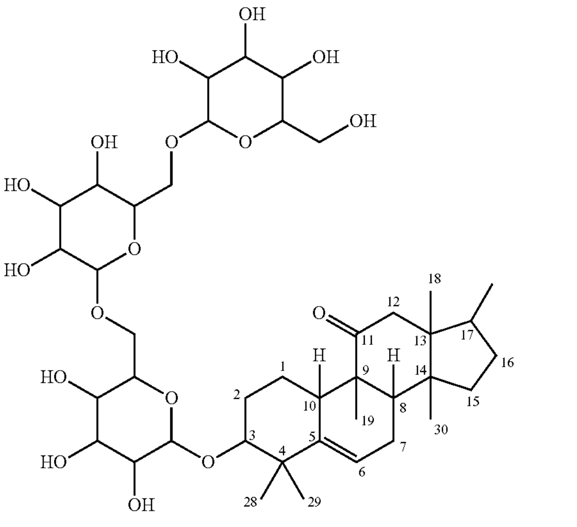
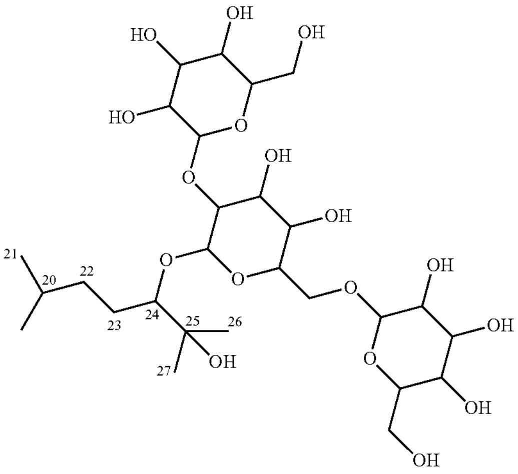
-continued
Formula 2
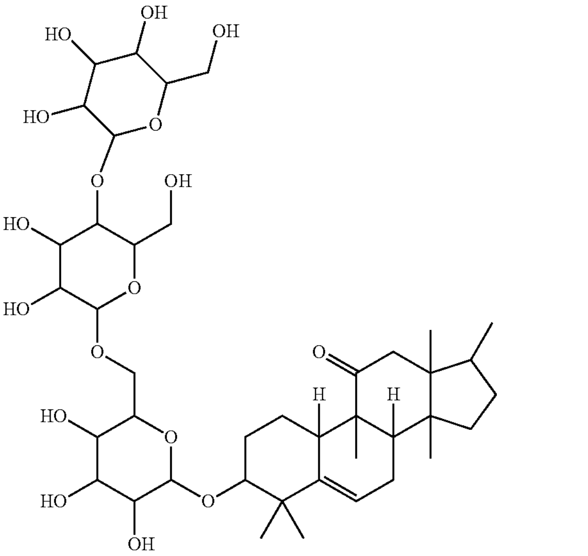
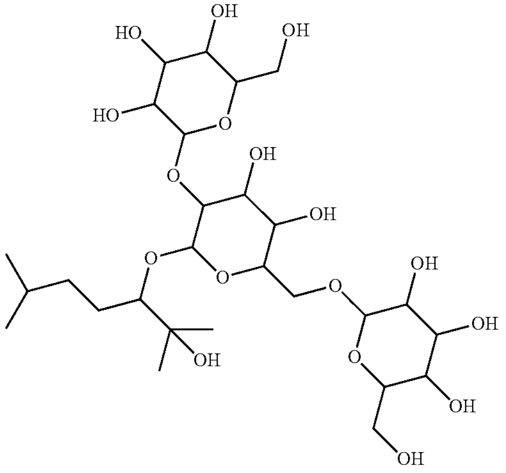
Formula 4
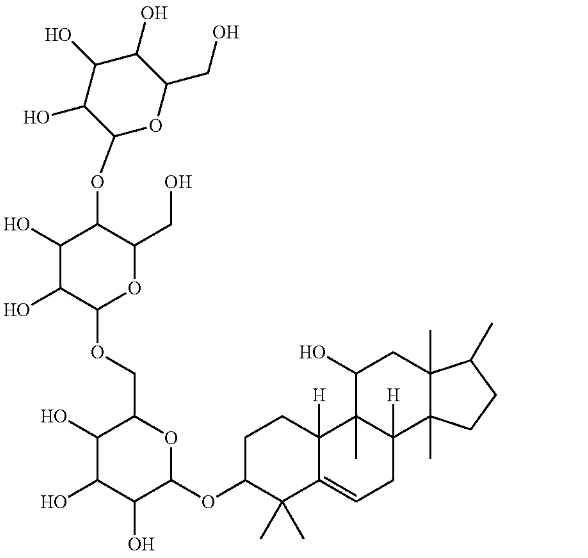

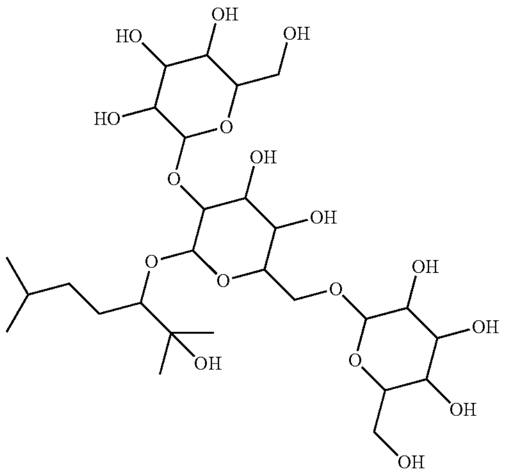
Formula 5
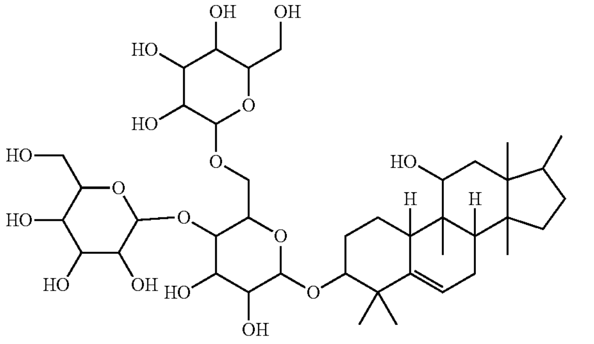
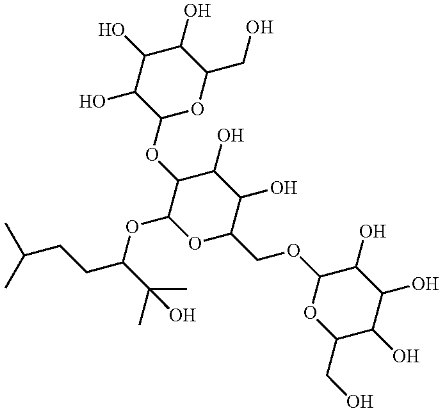
Formula 7
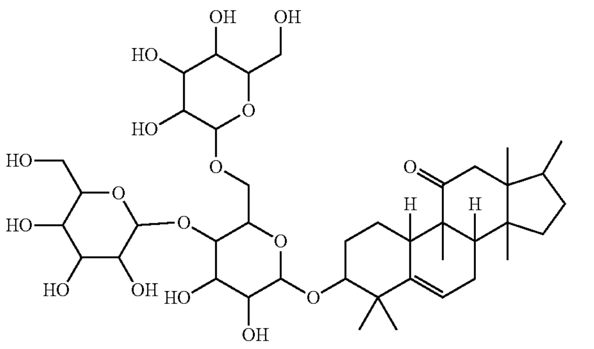
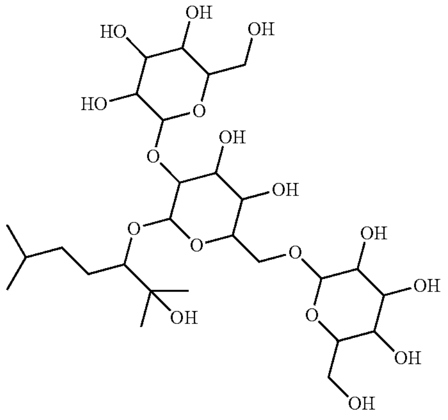
Formula 8
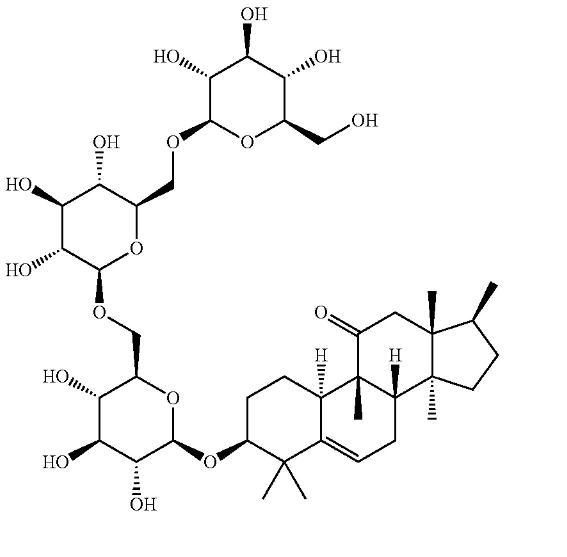
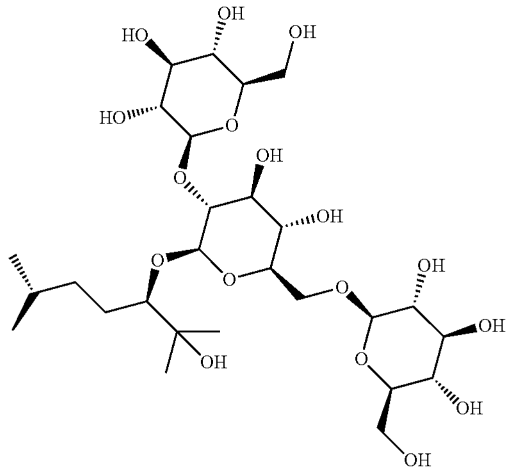

-continued
Formula 9
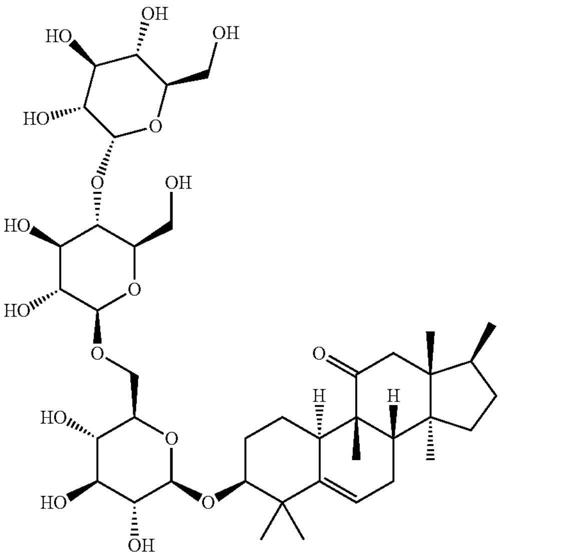
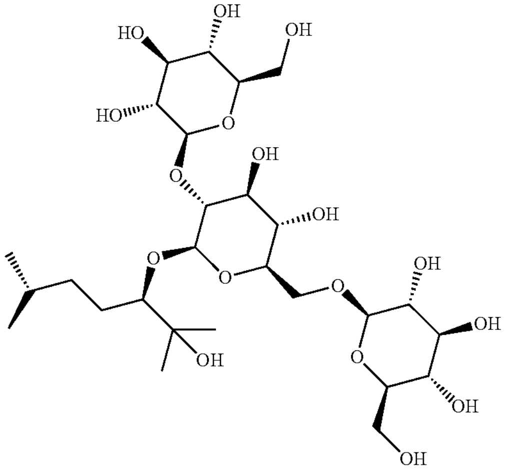
Formula 11
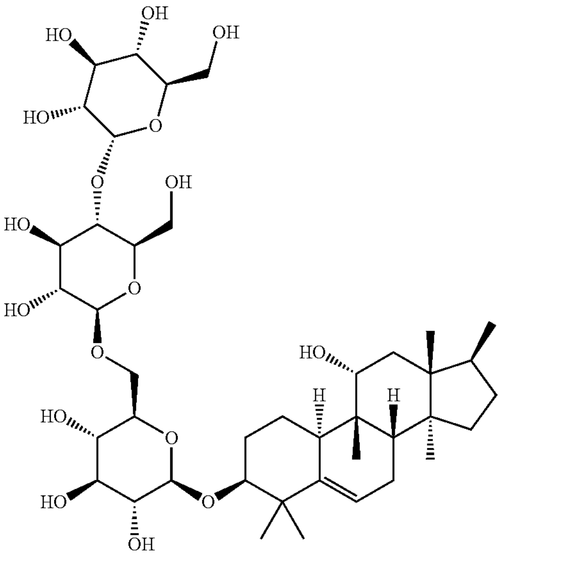
-continued
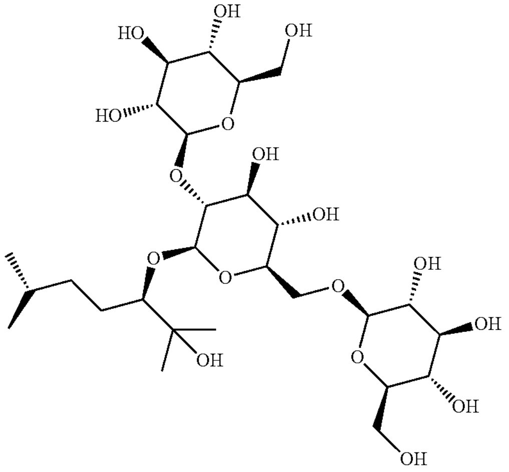
Formula 12
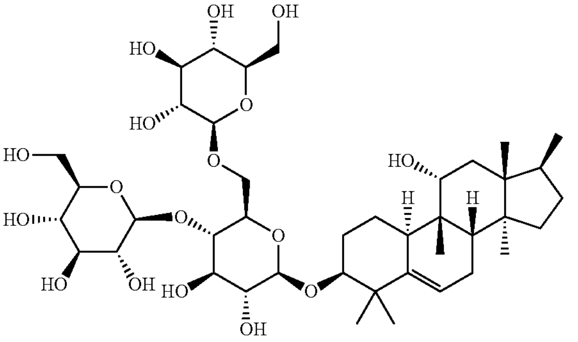
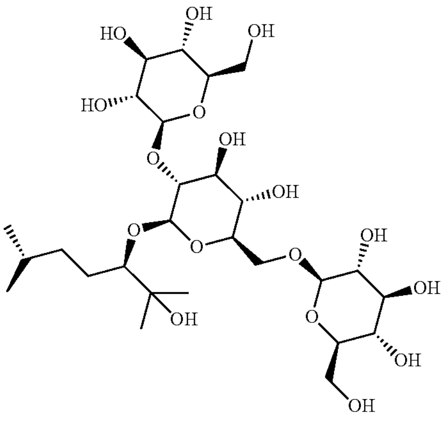
Formula 14
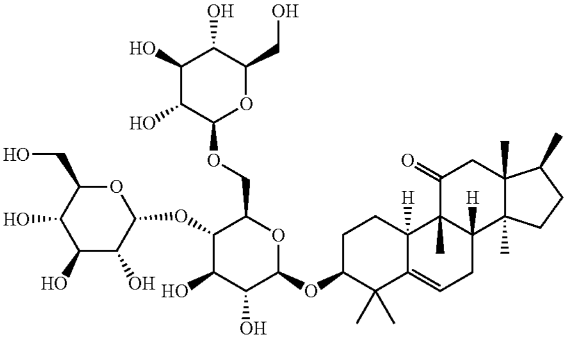

-continued

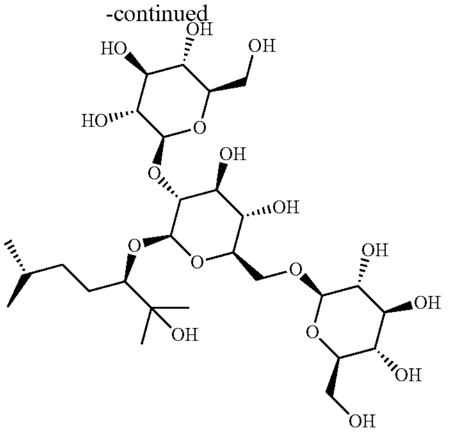

Formula 15

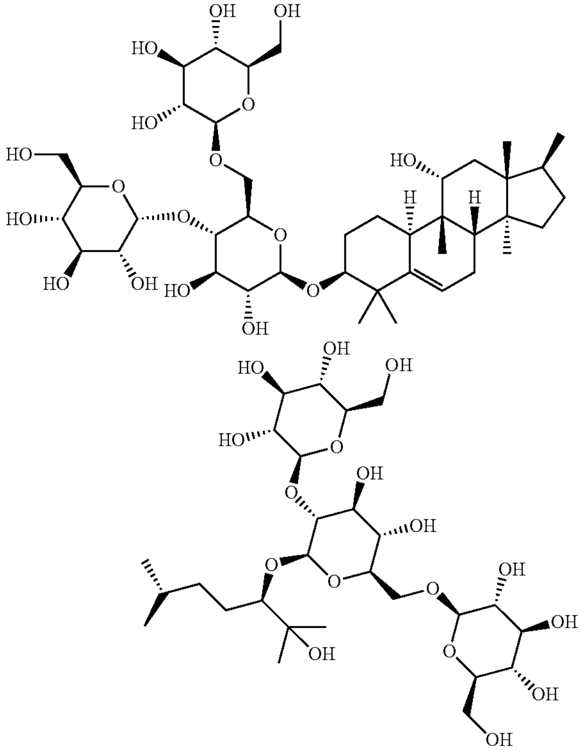

wherein the concentration of the mogroside compound is at or above the threshold sweetness recognition concentration of the compound or at or above the threshold flavor recognition concentration of the compound.

2. The consumable of claim 1, wherein the consumable is a beverage or food product.

3. The consumable of claim 1, further comprising at least one additional component selected from the group consisting of additional mogrosides, additional sweeteners, additives, functional ingredients, flavor ingredients, and combinations thereof.

4. The consumable of claim 3, wherein the additional mogrosides are selected from the group consisting of Luo han guo extract, by-products of other mogrosides' isolation and purification processes, mogroside IA, mogroside IE, 11-oxomogroside IA, mogroside II A, mogroside II B, mogroside II E, 7-oxomogroside II E, mogroside III, 11-deoxymogroside III, mogroside IV, 11-oxomogroside IV A, mogroside V, 7-oxomogroside V, 11-oxomogroside V, isomogroside V, mogroside VI, mogrol, 11-oxomogrol, isomogroside, siamenoside, siamenoside I, neomogroside, synthetic mogrosides, other mogrosides occurring in *Siraitia grosvenorii* fruits and combinations thereof.

5. The consumable of claim 3, wherein the sweetener comprises at least one is-selected from the group consisting of sucrose, glyceraldehyde, dihydroxyacetone, erythrose, threose, erythrulose, arabinose, lyxose, ribose, xylose, ribulose, xylulose, allose, altrose, allulose, galactose, glucose, gulose, idose, mannose, talose, fructose, psicose, sorbose, tagatose, mannoheptulose, sedoheltulose, octolose, fucose, rhamnose, arabinose, turanose, sialose, inulin, inulooligosaccharides, fructooligosaccharides, HFCS, maltodextrin, coupling sugar, honey, *stevia*, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, steviolbioside, stevioside, other steviol glycosides occurring in *Stevia rebaudiana* plant, biosynthetic steviol glycosides, glycosylated steviol glycosides, glucosylated steviol glycosides (GSGs), mogroside IV, mogroside V, mogroside VI, Luo han guo, siamenoside, other mogrosides occurring in *Siraitia grosvenorii* fruits, monatin and its salts, curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I, sugar alcohols, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof.

6. The consumable of claim 3, wherein the additive comprises at least one selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

7. The consumable of claim 3, wherein the functional ingredient comprises at least one selected from the group consisting of caffeine, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

* * * * *